(12) United States Patent
Chauhan et al.

(10) Patent No.: US 11,406,594 B2
(45) Date of Patent: Aug. 9, 2022

(54) OLEOGEL COMPOSITIONS FOR RETINAL DRUG DELIVERY

(71) Applicant: University of Florida Research Foundation, Inc., Gainesville, FL (US)

(72) Inventors: Anuj Chauhan, Gainesville, FL (US); Russell Macoon, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 16/761,901

(22) PCT Filed: Nov. 28, 2018

(86) PCT No.: PCT/US2018/062774
§ 371 (c)(1),
(2) Date: May 6, 2020

(87) PCT Pub. No.: WO2019/108602
PCT Pub. Date: Jun. 6, 2019

(65) Prior Publication Data
US 2021/0169796 A1 Jun. 10, 2021

Related U.S. Application Data

(60) Provisional application No. 62/591,454, filed on Nov. 28, 2017.

(51) Int. Cl.
*A61K 9/06* (2006.01)
*A61K 9/00* (2006.01)
(Continued)

(52) U.S. Cl.
CPC ............. *A61K 9/06* (2013.01); *A61K 9/0019* (2013.01); *A61K 9/0048* (2013.01);
(Continued)

(58) Field of Classification Search
CPC ....................................................... A61K 9/06
See application file for complete search history.

(56) References Cited

U.S. PATENT DOCUMENTS 5,589,177 A 12/1996 Herb et al.
2010/0291226 A1* 11/2010 Mazzone ............... A61K 47/44
424/523

(Continued)

OTHER PUBLICATIONS

Patel et al, Edible Applications of Shellac Oleogels: Spreads, Chocolate Pastes and Cakes, Food & Function, vol. 5, No. 4. (Year: 2014).*

(Continued)

*Primary Examiner* — Carlos A Azpuru
(74) *Attorney, Agent, or Firm* — Thomas | Horstemeyer LLP

(57) ABSTRACT

In one aspect, the disclosure relates to compositions for the extended release of drugs in the retina. In a further aspect, the present disclosure provides methods of preparing extended release compositions comprising a therapeutic agent for use in retinal drug delivery. In various other aspects, the present disclosure provides methods for delivery of the disclosed compositions comprising a therapeutic agent to the retina via intravitreal injection. This abstract is intended as a scanning tool for purposes of searching in the particular art and is not intended to be limiting of the present disclosure.

6 Claims, 27 Drawing Sheets

(51) Int. Cl.
*A61K 31/5377* (2006.01)
*A61K 47/10* (2017.01)
*A61K 47/12* (2006.01)
*A61K 47/38* (2006.01)
*A61K 47/44* (2017.01)

(52) U.S. Cl.
CPC .......... *A61K 31/5377* (2013.01); *A61K 47/10* (2013.01); *A61K 47/12* (2013.01); *A61K 47/38* (2013.01); *A61K 47/44* (2013.01)

(56) References Cited

U.S. PATENT DOCUMENTS

| | | | | |
|---|---|---|---|---|
| 2011/0158920 | A1* | 6/2011 | Morley | A61P 17/00 424/59 |
| 2013/0190278 | A1* | 7/2013 | Annat | A61K 9/0048 514/171 |
| 2017/0100357 | A1* | 4/2017 | Folan | A61K 8/06 |

OTHER PUBLICATIONS

International Search Report issued for PCT/US2018/062774, dated Feb. 8, 2019.
Patel et al., Edible applications of shellac oleogels: spreads, chocolate paste and cakes, Food & Function, vol. 5, No. 4, Apr. 2014.

* cited by examiner

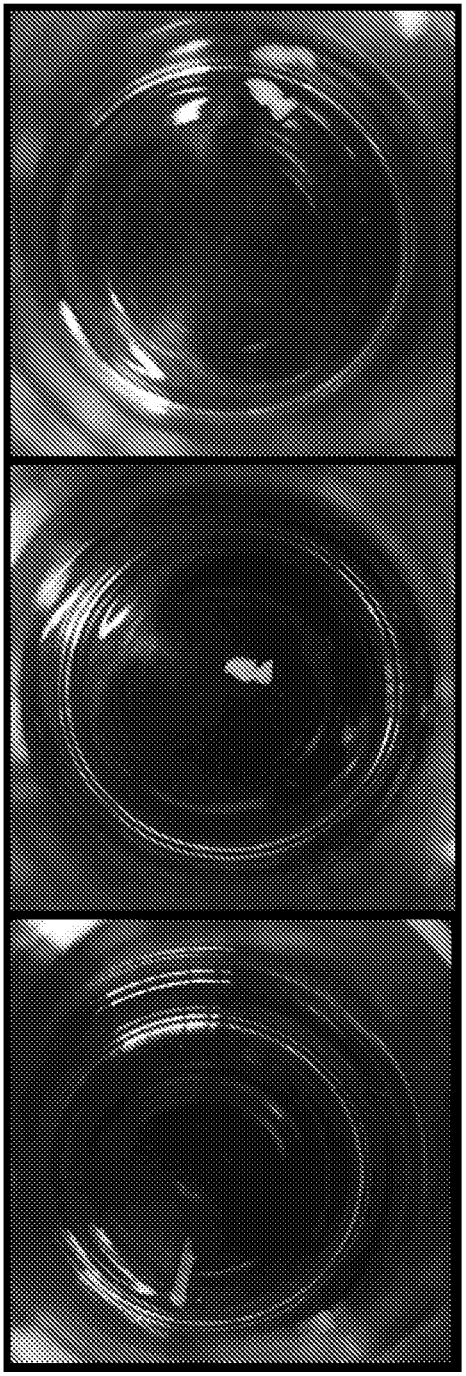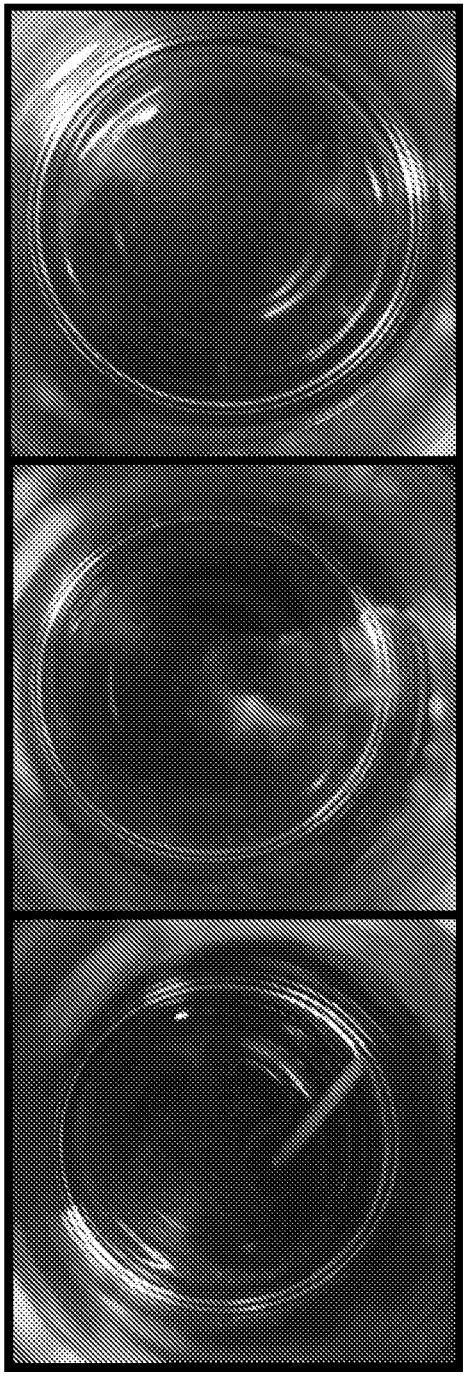

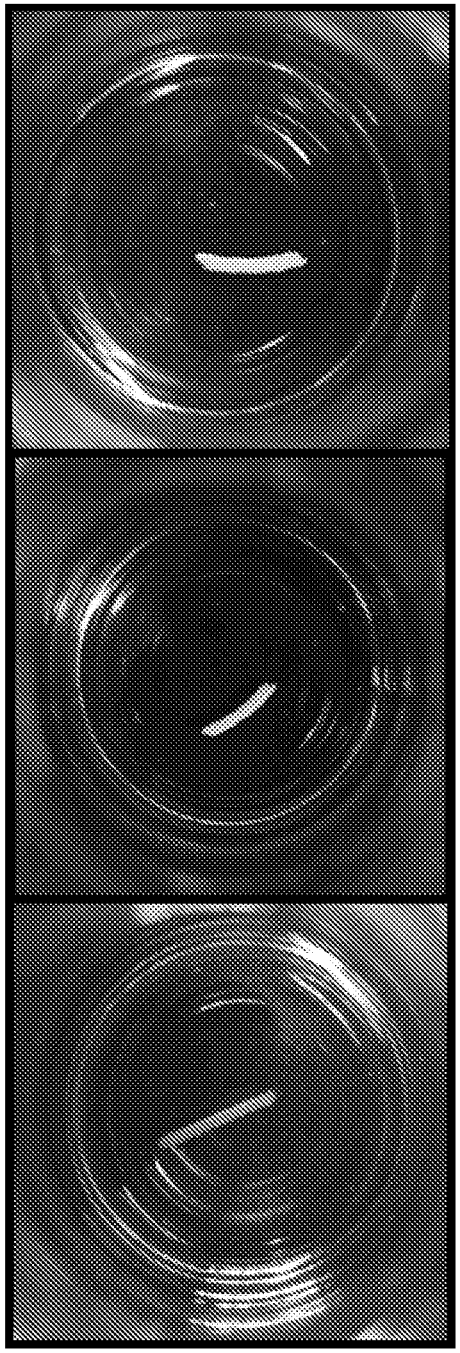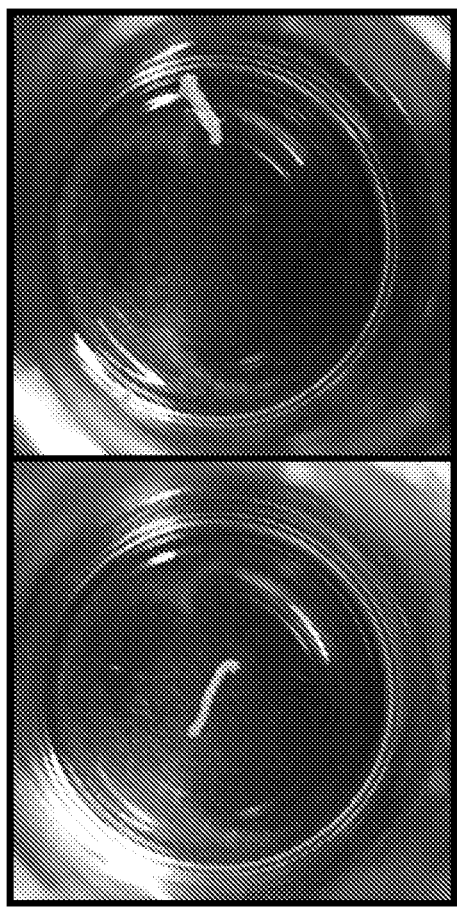

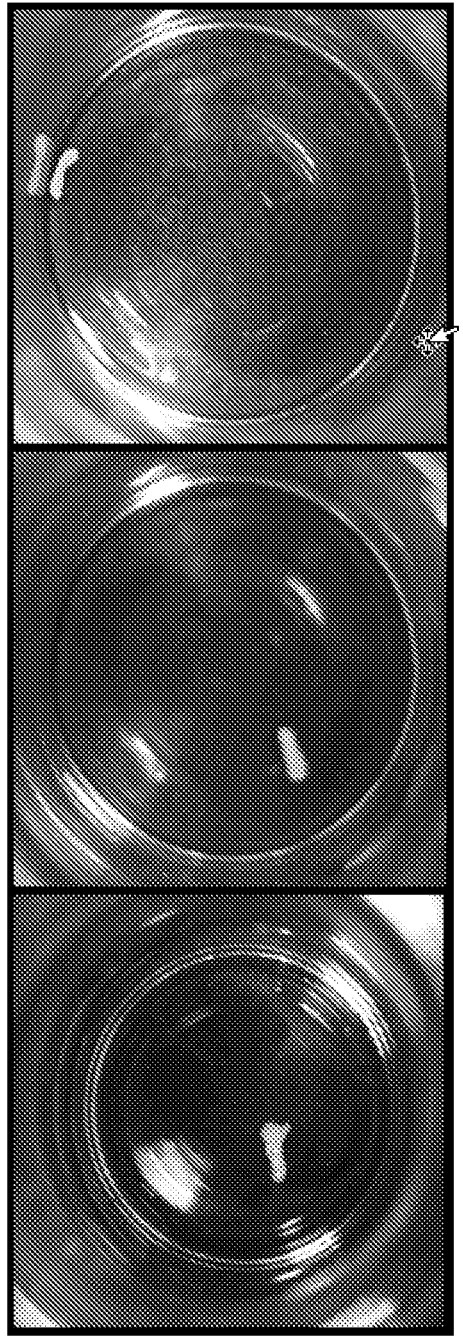
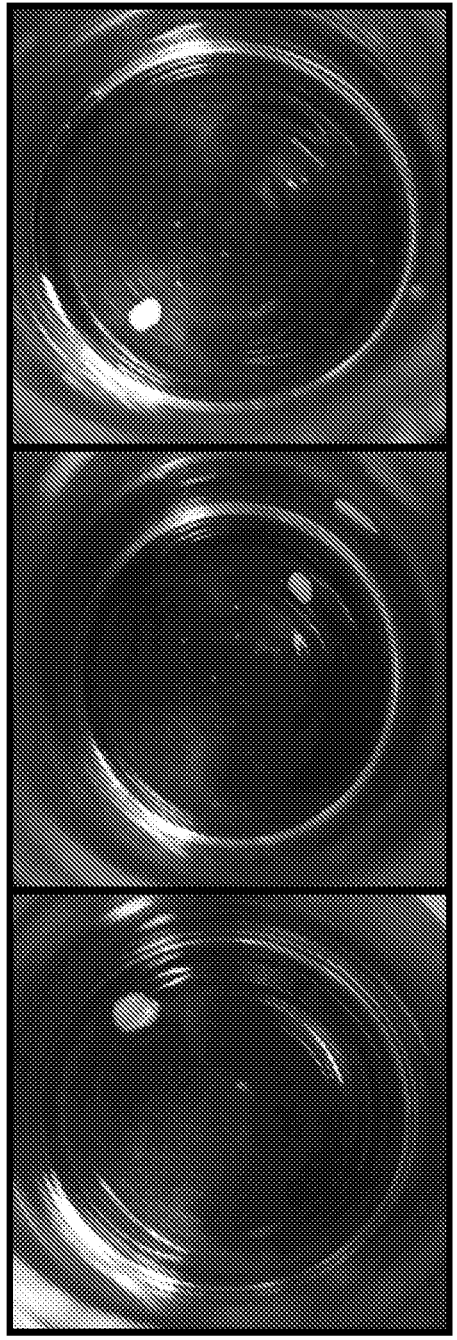

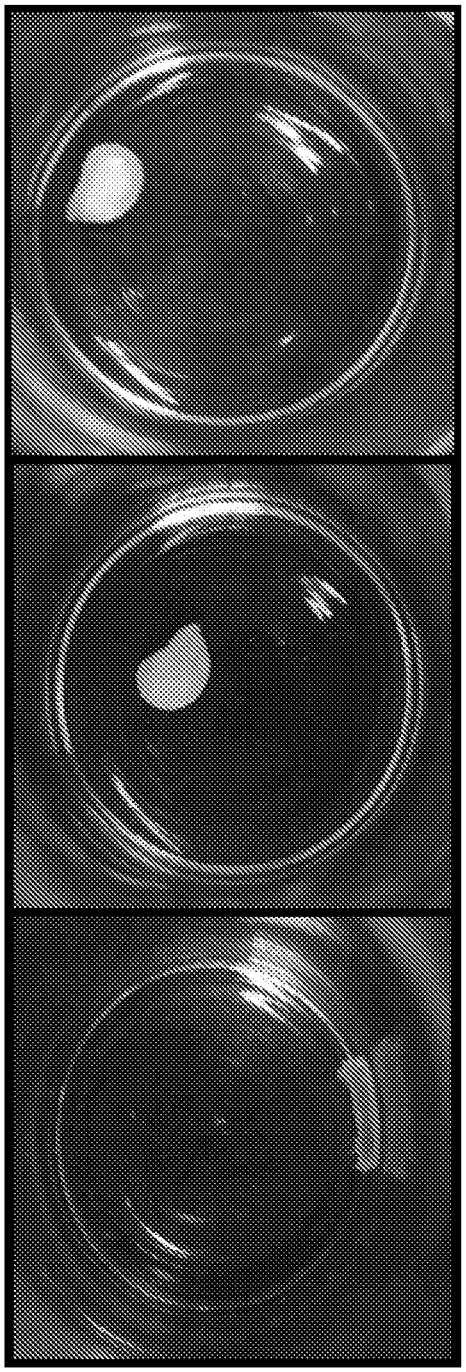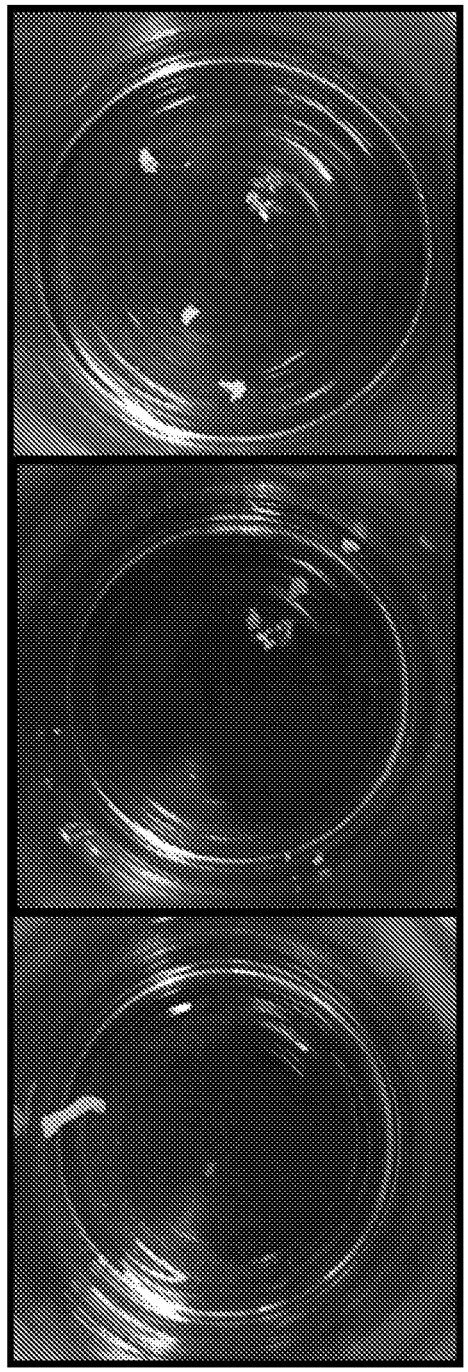

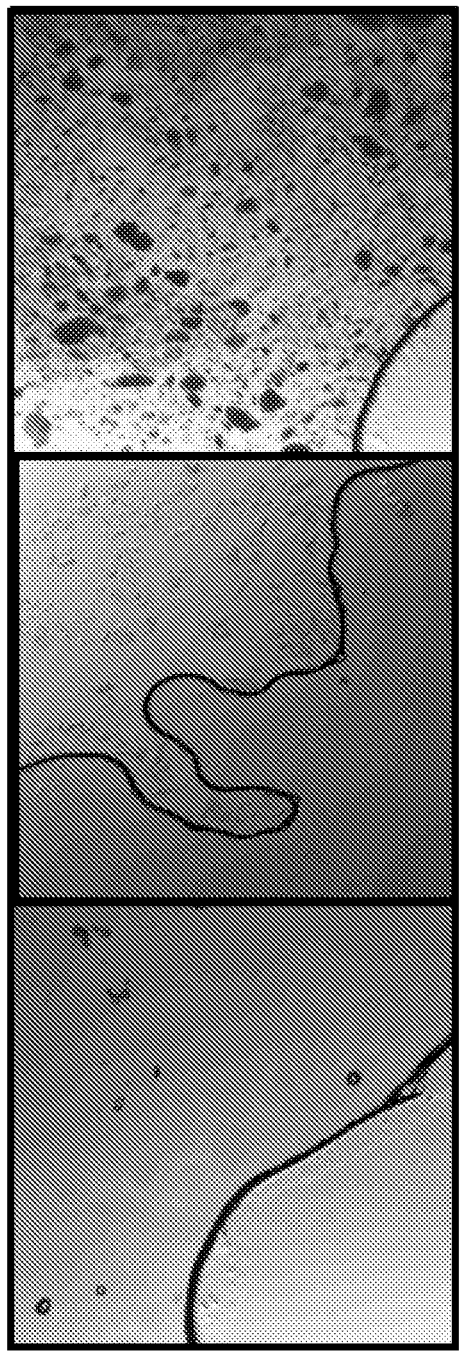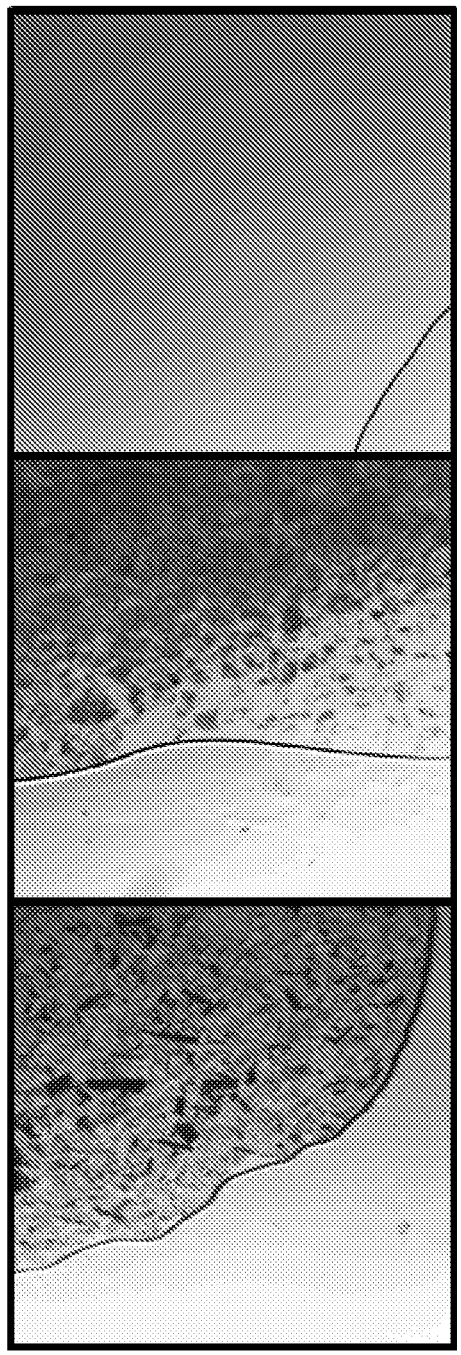

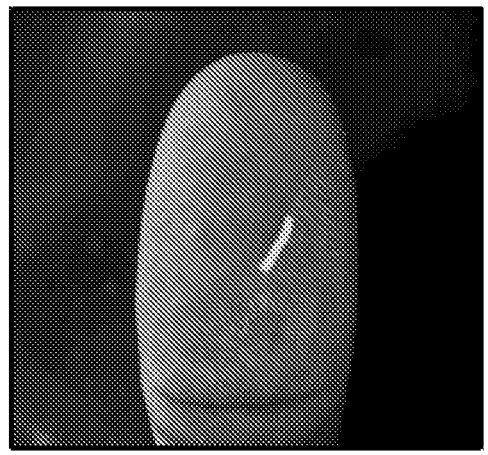
FIG. 13
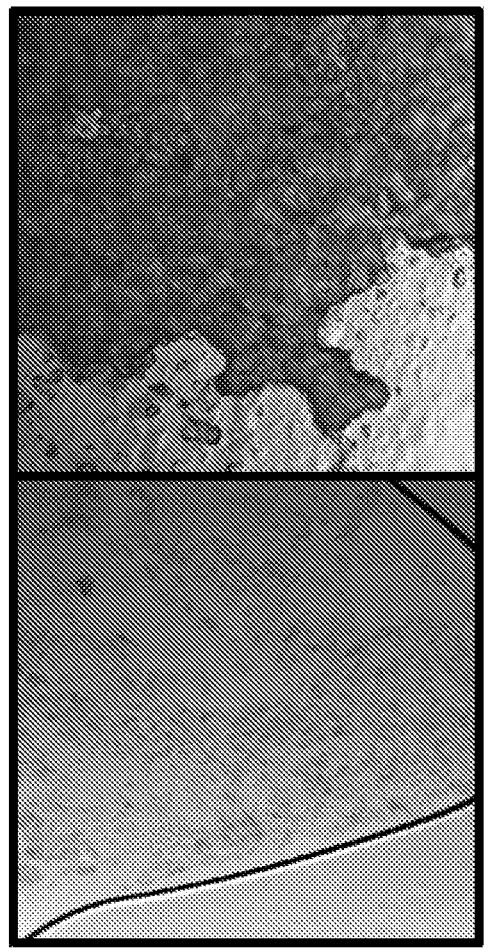
FIG. 12K
FIG. 12J

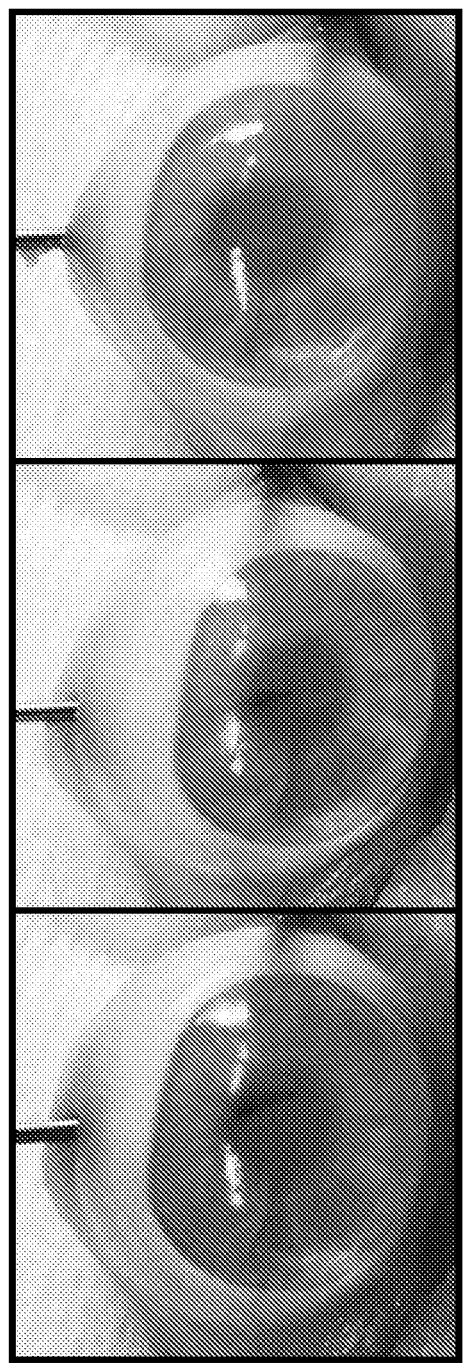

OLEOGEL COMPOSITIONS FOR RETINAL DRUG DELIVERY

CROSS-REFERENCE TO RELATED APPLICATIONS

This Application is a National Stage of International Application No. PCT/US2018/062774, filed Nov. 28, 2018, which claims the benefit of U.S. Provisional Application No. 62/591,454, filed on Nov. 28, 2017, which is incorporated herein by reference in its entirety.

BACKGROUND

Delivery of ophthalmic drugs to the back of the eye for treatment of retinal diseases remains a significant challenge for effective treatment of eye associated disorders and diseases. For the systemic delivery of drugs, there is the hurdle of the blood-retina barrier along with physico-chemical dynamics associated with effective diffusion of a therapeutic agent across the blood capillaries in the retina. Among the non-systemic delivery options there is drug delivery via eye drops administered to the eye. However, this approach is associated with a relatively large physical distance between the tears and the retina which leads to not only transport barriers, but also difficulty of clearance for elimination of the drug both from tears and ocular tissue.

In view of the foregoing, invasive drug administration methods remain the current state of the art. These invasive drug administration methods include intravitreal injections through the eye ball for delivery of retinal drugs. However, even though the currently preferred method of delivery for retinal drugs, there remain significant issues associated with intravitreal injections. Foremost, the currently available technologies require repeated monthly injections which result in reduced patient compliance, potential serious complications, including infections, and the risk of retinal detachment. There is clearly a need in the art for methods and compositions which provide a reduction in the frequency of the injection compared to currently available methods. The availability of methods and compositions that would provide extended release of the drugs in the retina could have very significant clinical benefits.

Despite advances in retinal drug delivery research, there is still a scarcity of viable methods and compositions that provide safe, effective, and low frequency for delivery of therapeutic agents to the eye, in particular, the retina. These needs and other needs are satisfied by the present disclosure.

SUMMARY

In accordance with the purpose(s) of the disclosure, as embodied and broadly described herein, the disclosure, in one aspect, relates to compositions for the extended release of drugs in the retina. In a further aspect, the present disclosure provides methods of preparing extended release compositions comprising a therapeutic agent for use in retinal drug delivery. In various other aspects, the present disclosure provides methods for delivery of the disclosed compositions comprising a therapeutic agent to the retina via intravitreal injection.

In an aspect, the disclosure pertains to a drug delivery composition that is an oleogel composition. In a further aspect, the disclosed oleogel composition further comprises one or more therapeutic agents. In a still further aspect, the disclosed drug delivery compositions are an oleogel comprising an oil phase and a gelator.

In an aspect, the disclosure pertains to a drug delivery composition in which a water in oil emulsion is prepared such that the oil phase gels resulting in a composition comprising of water drops dispersed in gelled oil. In a further aspect, drug delivery composition in which a water in oil emulsion is prepared further comprises one or more therapeutic agents. In a still further aspect, the one or more therapeutic agents comprise a water soluble therapeutic agent.

Also disclosed herein are methods of treating a clinical condition comprising injecting a disclosed drug delivery composition comprising a therapeutic agent.

Also disclosed herein are drug delivery devices for delivery a disclosed drug delivery composition comprising a therapeutic agent to a portion of the eye.

While aspects of the present disclosure can be described and claimed in a particular statutory class, such as the system statutory class, this is for convenience only and one of skill in the art will understand that each aspect of the present disclosure can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the disclosure.

FIG. 1A shows the drug delivery composition shortly after expunging into phosphate-buffered saline. FIGS. 1B and 1C show the same drug delivery composition at 79 days and 124 days, respectively, following initial expunging into phosphate-buffered saline.

FIG. 2A shows the drug delivery composition shortly after expunging into phosphate-buffered saline. FIGS. 2B and 2C show the same drug delivery composition at 51 days and 96 days, respectively, following initial expunging into phosphate-buffered saline.

FIGS. 3A-3C show a representative disclosed drug delivery composition comprising the test formulation described in Table 1, test formulation C. The disclosed drug delivery composition in FIGS. 3A-3C was expunged through a 22 gauge needle into phosphate-buffered saline. FIG. 3A shows the drug delivery composition shortly after expunging into phosphate-buffered saline. FIGS. 3B and 3C show the same drug delivery composition at 52 days and 97 days, respectively, following initial expunging into phosphate-buffered saline.

FIGS. 4A-4C show a representative disclosed drug delivery composition comprising the test formulation described in Table 1, test formulation D. The disclosed drug delivery composition in FIGS. 4A-4C was expunged through a 22 gauge needle into phosphate-buffered saline. FIG. 4A shows the drug delivery composition shortly after expunging into phosphate-buffered saline. FIGS. 4B and 4C show the same drug delivery composition at 34 days and 79 days, respectively, following initial expunging into phosphate-buffered saline.

FIGS. 5A-5C show a representative disclosed drug delivery composition comprising the test formulation described in Table 1, test formulation E. The disclosed drug delivery composition in FIGS. 5A-5C was expunged through a 22 gauge needle into phosphate-buffered saline. FIG. 5A shows the drug delivery composition shortly after expunging into phosphate-buffered saline. FIGS. 5B and 5C show the same drug delivery composition at 67 days and 112 days, respectively, following initial expunging into phosphate-buffered saline.

FIGS. 6A-6B show a representative disclosed drug delivery composition comprising the test formulation described in Table 1, test formulation F. The disclosed drug delivery composition in FIGS. 6A-6B was expunged through a 22 gauge needle into phosphate-buffered saline. FIG. 6A shows the drug delivery composition shortly after expunging into phosphate-buffered saline. FIG. 6B shows the same drug delivery composition at 18 days following initial expunging into phosphate-buffered saline.

FIGS. 7A-7C show a representative disclosed drug delivery composition comprising the test formulation described in Table 1, test formulation G. The disclosed drug delivery composition in FIGS. 7A-7C was expunged through a 22 gauge needle into phosphate-buffered saline. FIG. 7A shows the drug delivery composition shortly after expunging into phosphate-buffered saline. FIGS. 7B and 7C show the same drug delivery composition at 23 days and 68 days, respectively, following initial expunging into phosphate-buffered saline.

FIGS. 8A-8C show a representative disclosed drug delivery composition comprising the test formulation described in Table 1, test formulation H. The disclosed drug delivery composition in FIGS. 8A-8C was expunged through a 22 gauge needle into phosphate-buffered saline. FIG. 8A shows the drug delivery composition shortly after expunging into phosphate-buffered saline. FIGS. 8B and 8C show the same drug delivery composition at 17 days and 62 days, respectively, following initial expunging into phosphate-buffered saline.

FIGS. 9A-9C show a representative disclosed drug delivery composition comprising the test formulation described in Table 1, test formulation I. The disclosed drug delivery composition in FIGS. 9A-9C was expunged through a 14 gauge needle into phosphate-buffered saline. FIG. 9A shows the drug delivery composition shortly after expunging into phosphate-buffered saline. FIGS. 9B and 9C show the same drug delivery composition at 99 days and 144 days, respectively, following initial expunging into phosphate-buffered saline.

FIGS. 10A-10C show a representative disclosed drug delivery composition comprising the test formulation described in Table 1, test formulation J. The disclosed drug delivery composition in FIGS. 10A-10C was expunged through a 22 gauge needle into phosphate-buffered saline. FIG. 10A shows the drug delivery composition shortly after expunging into phosphate-buffered saline. FIGS. 10B and 10C show the same drug delivery composition at 45 days and 90 days, respectively, following initial expunging into phosphate-buffered saline.

FIG. 11A shows the drug delivery composition shortly after expunging into phosphate-buffered saline. FIGS. 11B and 11C show the same drug delivery composition at 37 days and 82 days, respectively, following initial expunging into phosphate-buffered saline.

FIGS. 12A-12K show representative photomicrographic images of the representative disclosed drug delivery compositions. The images were captured at 2× magnification immediately following being expunged from a needle into phosphate-buffered saline. FIGS. 12A-K show images from disclosed drug delivery composition corresponding to the test formulation described in Table 1, test formulations A-K, respectively.

FIG. 13 shows a representative image of a representative disclosed drug delivery composition comprising a representative oleogel further comprising dexamethasone. In some aspects, the figure shows that the overall size of a delivered drug delivery composition can be determined by the needle gauge used for delivery and the target mass of the delivered composition.

FIG. 14A shows a composition that has been expunged through a 14 gauge needle into phosphate-buffered saline at 141 days post-delivery into the phosphate-buffered saline. FIG. 14B shows a composition that has been expunged through a 25 gauge needle into phosphate-buffered saline at 120 days post-delivery into the phosphate-buffered saline.

FIGS. 28A-28C show representative images of different aspects of a disclosed method of using the disclosed drug delivery compositions using a model of the human eye. Briefly, the disclosed drug delivery composition was prepared and injected using a 19 gauge hypodermic needle. FIG. 28A shows insertion of the needle through the lateral side of the model eye such that the tip of the needle is localized within a central portion of the vitreous.

FIG. 28B shows ejection or expunging of the drug delivery composition into the vitreous, with the image showing a portion of the drug delivery composition extending from the tip of the needle into the vitreous. FIG. 28C shows removal of the needle from the model eye such that the ejected drug delivery composition adheres to the needle as it is being removed until the drug delivery composition dislodges from the needle tip and remains in the vitreous.

FIG. 29A shows a representative side view aspect of the disclosed needle, 10, wherein the tip, 11, has an essentially blunt configuration. FIG. 29B shows a representative side view aspect of the disclosed needle, 10, wherein the tip, 11, has an essentially angled or pointed configuration.

FIG. 29C shows a representative cross-sectional view of area, 14, show in FIG. 29A. In the cross-sectional view it is shown that in some aspects, individual exit openings, e.g., 15' and 15", of the plurality of exit openings, 15, are characterized by an angle, $\theta$, such as $\theta_1$ and $\theta_2$, respectively, of the exit opening relative to the surface of the needle wall, 18. The angled exit opening in multiple directions and at multiple angles, thereby forming a network matrix comprising the drug delivery compostions.

FIG. 30A shows the drug delivery composition in the initial phase of being ejected through the plurality of exit openings in the plastic tube. FIG. 30B shows an exemplary gel-like network formed by the ejected drug delivery composition after complete ejection from the plastic tube comprising the plurality of exit openings.

FIG. 31A shows a representative cross-sectional view of a drug deliver device, 20. FIG. 31B shows a close-up cross-sectional side view, 27, of the plurality of drug delivery compositions, 28, position on a porous structure, 29. In the figure, each letter represents a distinct drug delivery composition of the plurality of drug delivery compositions, 28, each independently comprising a drug, with the ensemble of three drug delivery compositions shown positioned on the porous structure, 29. A cross-sectional top view is shown in 27a.

FIG. 35A shows the drug delivery composition comprising the fluorescent dye immediately after injection. The image shows that the drug delivery composition following injection into the vitreous has a physical structure of a rod or cylinder. The fluorescent spot near the lateral side of the model eye is the injection site showing residual amounts of the drug delivery composition comprising the fluorescent dye adhering near the injection entry site. FIG. 35B shows the same drug delivery composition comprising the fluorescent dye at two days following injection. The image shows that the drug delivery composition comprising the fluorescent dye remains clearly visible and apparently intact near the front of the eye. FIG. 35C shows the same drug delivery composition comprising the fluorescent dye at four days following injection. The image shows that the model eye tissue is beginning to degrade, thus coloring the model eye lens. However, the drug delivery composition comprising the fluorescent dye remains clearly visible and apparently intact. FIG. 35D shows the same drug delivery composition comprising the fluorescent dye at five days following injection. The image shows that the drug delivery composition comprising the fluorescent dye remains clearly visible and apparently intact near the front of the eye at five days post-injection into the vitreous.

Figures 1A, 1B, 1C:
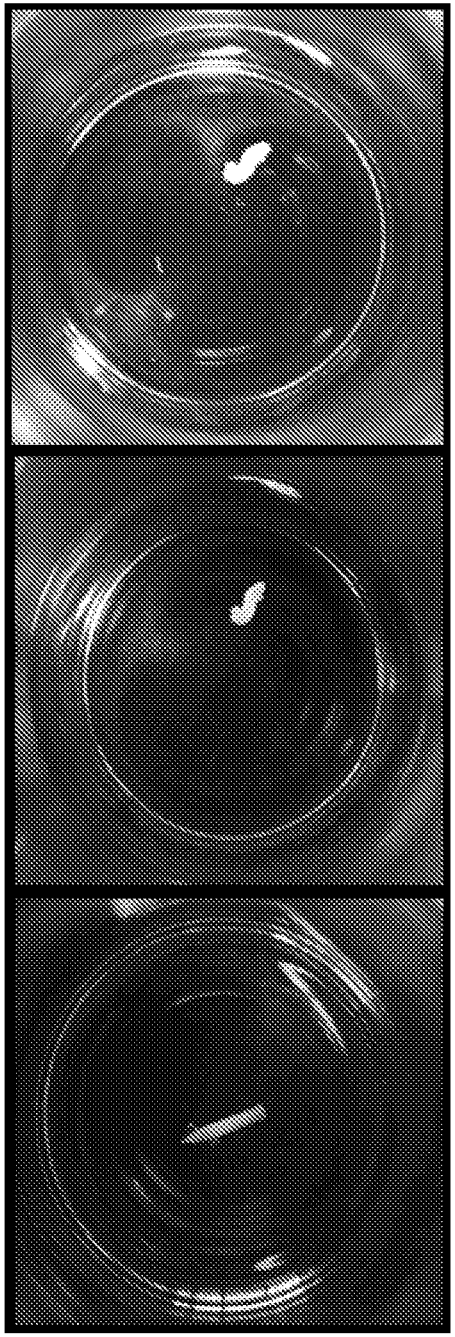
FIGS. 1A-1C show a representative disclosed drug delivery composition comprising the test formulation described in Table 1, test formulation A. The disclosed drug delivery composition in FIGS. 1A-1C was expunged through a 22 gauge needle into phosphate-buffered saline.

Additional advantages of the disclosure will be set forth in part in the description which follows, and in part will be obvious from the description, or can be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

DETAILED DESCRIPTION

The present disclosure can be understood more readily by reference to the following detailed description of the disclosure and the Examples included therein.

A. Definitions

As used in the specification and the appended claims, the singular forms "a," "an" and "the" include plural referents unless the context clearly dictates otherwise. Thus, for example, reference to "a therapeutic agent," "a drug delivery composition," or "a gelator" includes mixtures of two or more such therapeutic agents, drug delivery compositions, or gelators, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "about," "approximate," "at or about," and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

Unless stated otherwise, a weight percent (wt %) of a component is a wt/wt % value based on the total weight of the formulation or composition in which the component is included.

As used herein, the terms "optional" or "optionally" means that the subsequently described event or circumstance can or can not occur, and that the description includes instances where said event or circumstance occurs and instances where it does not.

As used herein, the term "subject" can be a vertebrate, such as a mammal, a fish, a bird, a reptile, or an amphibian. Thus, the term "subject" also includes domesticated animals (e.g., cats, dogs, rabbits, guinea pigs, etc.), livestock (e.g., cattle, horses, pigs, sheep, goats, horse, etc.), and laboratory animals (e.g., mouse, rabbit, rat, guinea pig, fruit fly, etc.). The term "subject" is also understood to include, as appropriate, a mammal such as a primate, and, in a further aspects, the subject is a human. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment of one or more oncological disorders or cancers prior to the administering step. In some aspects of the disclosed method, the subject has been diagnosed with a need for inhibition or negative modulation of STAT3 prior to the administering step. In some aspects of the disclosed method, the subject has been diagnosed with a need for treatment of one or more oncological disorders or cancers associated with STAT3 dysfunction prior to the administering step.

As used herein, the term "treatment" refers to the medical management of a patient with the intent to cure, ameliorate, stabilize, or prevent a disease, pathological condition, or disorder. This term includes active treatment, that is, treatment directed specifically toward the improvement or amelioration of a disease, pathological condition, or disorder, and also includes causal treatment, that is, treatment directed toward removal of the cause of the associated disease, pathological condition, or disorder. As used herein, and as well-understood in the art, "treatment" is an approach for obtaining beneficial or desired results, including clinical results. For purposes of the present disclosure, beneficial or desired clinical results include, but are not limited to, alleviation or amelioration of one or more symptoms, diminishment of extent of disease, stabilized (i.e., not worsening) state of disease, delay or slowing of disease progression, and/or amelioration or palliation of the disease state. "Treatment" can also mean prolonging survival as compared to expected survival if not receiving treatment.

In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; (iii) relieving the disease, i.e., causing regression of the disease; and/or (iv) reduction in the severity of one or more symptoms associated with the disease, disorder or condition. In some aspects of the present disclosure, reduction in the severity of one or more symptoms associated with the disease, disorder or condition can refer to amelioration of one or more of the following: pain, swelling, redness or inflammation associated with an inflammatory condition or an autoimmune disease.

As used herein, the terms "effective amount" and "amount effective" refer to an amount that is sufficient to achieve the desired result or to have an effect on an undesired condition.

As used herein, the term "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition. A "therapeutically effective amount" as used herein, is intended to mean an amount sufficient to reduce by at least 10%, preferably at least 25%, more preferably at least 50%, and most preferably an amount that is sufficient to cause an improvement in one or more clinically significant symptoms in the patient.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

B. Drug Delivery Compositions

In one aspect, the disclosure relates to a drug delivery composition or drug delivery device comprising an oleogel composition. In a further aspect, the disclosed oleogel composition further comprises one or more therapeutic agents. The disclosed oleogel compositions are relatively cheap and easy to prepare, offer stability to emulsions and other liquid based drug systems, can be thermoreversible, can be resistant to microbial contaminates, and can be formulated with both hydrophilic and hydrophobic drugs. The disclosed oleogel compositions controlled release of ophthalmic formulations, both for the front and the back of the eye. In some aspects, the disclosed oleogel compositions can be used for delivery of a therapeutic agent to the back eye via injection of a drug-loaded composition into the vitreous. The disclosed oleogel compositions can retain a given shape or geometry, such as a cylindrical or spherical geometry, after injection into the vitreous. In some aspects, the disclosed oleogel compositions have a high viscosity. In some instances, the high viscosity of the oleogel facilitates maintenance of the initial shape or geometry following injection. In a further aspect, the slow dissolution of an oil in the oleogel will eventually lead to degradation of the injected oleogel composition.

In an aspect, the disclosed drug delivery compositions are an oleogel comprising an oil phase and a gelator. The term "oleogel" herein refers to a gel having a continuous oil phase having a gelator uniformly dispersed in the gel phase and functioning as the gelling agent. The oleogels are suitably clear and translucent, generally transparent materials having the physical properties of a true gel. The oleogels optionally comprise a surfactant, which when present is likewise homogeneously distributed through the oleogel. Thus, the surfactant is not concentrated at the surface of oil or water micelles as in an emulsion. The oleogel may consist essentially of one or more oils or fats, the gelator, and optionally, the surfactant. The oleogel composition has characteristics of a gel. The term "gel" herein is used in its usual sense of a material having a continuous structure with macroscopic dimensions that is permanent on the time scale of an analytical experiment and is solid-like in its rheological properties. Gels bounce rather than flow, and exhibit substantially linear viscoelastic characteristics, at stresses below their yield stress. Gels have a melting point. Gels are conveniently defined by their rheological properties, in particular their yield stress and the ratio of their elastic modulus to their viscous modulus (G'/G") as measured at 20° C. and 1 Hz in a conventional viscoelastic analyzer as described below. Gel-like behaviour is characterized by G'/G" greater than about 1 under these conditions.

In a further aspect, a disclosed oleogel comprises an oil phase comprising one or more oils; and a gelator. In a still further aspect, a disclosed oleogel comprises an oil phase comprising one or more oils; and a gelator; wherein the oil phase is present in an amount of about 10 wt % to about 30 wt %; wherein the gelator is present in an amount of about 5 wt % to about 20 wt %; and wherein the wt % values are based on the weight of the one or more oils and of the gelator.

In a further aspect, a disclosed oleogel comprises one or more oils present in an amount, based on the weight of the one or more oils and of the gelator, of about 10 wt %, 10.5 wt %, 11 wt %, 11.5 wt %, 12 wt %, 12.5 wt %, 13 wt %, 13.5 wt %, 14 wt %, 14.5 wt %, 15 wt %, 15.5 wt %, 16 wt %, 16.5 wt %, 17 wt %, 17.5 wt %, 18 wt %, 18.5 wt %, 19 wt %, 19.5 wt %, 20 wt %, 20.5 wt %, 21 wt %, 21.5 wt %, 22 wt %, 22.5 wt %, 23 wt %, 23.5 wt %, 24 wt %, 24.5 wt %, 25 wt %, 25.5 wt %, 26 wt %, 26.5 wt %, 27 wt %, 27.5 wt %, 28 wt %, 28.5 wt %, 29 wt %, 29.5 wt %, 30 wt %; a range encompassed by any of the foregoing values; or a set of any of the foregoing values.

In a further aspect, a disclosed oleogel comprises soybean oil present in an amount, based on the weight of the one or more oils and of the gelator, of about 10 wt %, 10.5 wt %, 11 wt %, 11.5 wt %, 12 wt %, 12.5 wt %, 13 wt %, 13.5 wt %, 14 wt %, 14.5 wt %, 15 wt %, 15.5 wt %, 16 wt %, 16.5 wt %, 17 wt %, 17.5 wt %, 18 wt %, 18.5 wt %, 19 wt %, 19.5 wt %, 20 wt %, 20.5 wt %, 21 wt %, 21.5 wt %, 22 wt %, 22.5 wt %, 23 wt %, 23.5 wt %, 24 wt %, 24.5 wt %, 25 wt %, 25.5 wt %, 26 wt %, 26.5 wt %, 27 wt %, 27.5 wt %, 28 wt %, 28.5 wt %, 29 wt %, 29.5 wt %, 30 wt %; a range encompassed by any of the foregoing values; or a set of any of the foregoing values.

In a further aspect, a disclosed oleogel comprises a gelator present in an amount, based on the weight of the one or more oils and of the gelator, of about 5 wt %, 5.5 wt %, 6 wt %, 6.5 wt %, 7 wt %, 7.5 wt %, 8 wt %, 8.5 wt %, 9 wt %, 9.5 wt %, 10 wt %, 10.5 wt %, 11 wt %, 11.5 wt %, 12 wt %, 12.5 wt %, 13 wt %, 13.5 wt %, 14 wt %, 14.5 wt %, 15 wt %, 15.5 wt %, 16 wt %, 16.5 wt %, 17 wt %, 17.5 wt %, 18 wt %, 18.5 wt %, 19 wt %, 19.5 wt %, 20 wt %; a range encompassed by any of the foregoing values; or a set of any of the foregoing values.

In a further aspect, a disclosed oleogel comprises ethyl cellulose as the gelator, and wherein the ethyl cellulose is present in an amount, based on the weight of the one or more oils and of the gelator, of about 5 wt %, 5.5 wt %, 6 wt %, 6.5 wt %, 7 wt %, 7.5 wt %, 8 wt %, 8.5 wt %, 9 wt %, 9.5 wt %, 10 wt %, 10.5 wt %, 11 wt %, 11.5 wt %, 12 wt %, 12.5 wt %, 13 wt %, 13.5 wt %, 14 wt %, 14.5 wt %, 15 wt %, 15.5 wt %, 16 wt %, 16.5 wt %, 17 wt %, 17.5 wt %, 18 wt %, 18.5 wt %, 19 wt %, 19.5 wt %, 20 wt %; a range encompassed by any of the foregoing values; or a set of any of the foregoing values.

In a further aspect, a disclosed oleogel further comprises octanoic acid, wherein the octanoic acid is present in an amount of from about 10 wt % to about 30 wt % based on the weight of the one or more oils, the gelator, and the octanoic acid. In a still further aspect, a disclosed oleogel further comprises octanoic acid, wherein the octanoic acid is present in an amount, based on the weight of the one or more oils, the gelator, and the octanoic acid, of about 10 wt %, 10.5 wt %, 11 wt %, 11.5 wt %, 12 wt %, 12.5 wt %, 13 wt %, 13.5 wt %, 14 wt %, 14.5 wt %, 15 wt %, 15.5 wt %, 16 wt %, 16.5 wt %, 17 wt %, 17.5 wt %, 18 wt %, 18.5 wt %, 19 wt %, 19.5 wt %, 20 wt %, 20.5 wt %, 21 wt %, 21.5 wt %, 22 wt %, 22.5 wt %, 23 wt %, 23.5 wt %, 24 wt %, 24.5 wt %, 25 wt %, 25.5 wt %, 26 wt %, 26.5 wt %, 27 wt %, 27.5 wt %, 28 wt %, 28.5 wt %, 29 wt %, 29.5 wt %, 30 wt %; a range encompassed by any of the foregoing values; or a set of any of the foregoing values.

In a further aspect, the oil phase comprises a triacylglycerol oil. In a still further aspect, oil phase comprises a mono-, di-, and triglycerides of synthetic, semisynthetic and natural origin, and mixtures thereof.

In a further aspect, the oil phase comprises an oil such as soybean oil, castor oil coconut oil, canola oil, corn oil, cottonseed oil, flaxseed oil, olive oil, palm oil, rapeseed oil, rice bran oil, saffron oil, sesame oil, sunflower oil, peanut oil, almond oil, linseed oil, hazelnut oil, poppy seed oil, mustard seed oil, avocado oil, cashew nut oil, cocoa butter, grapeseed oil, shea butter, and combinations thereof. In a further aspect, the oil phase comprises a synthetic oil such as a silicone oil. The foreogoing are plant-derived oils. In a yet further aspect, the oil phase comprises an animal derived oil such as a fish oil, including, but not limited to, salmon oil, halibut oil, and combinations thereof, or in combination with one or more of the disclosed plant-derived oils.

In a further aspect, the gelator comprises a non-lipid based components such as ethyl cellulose, candelilla wax, chitin, and colloidal silicon dioxide, saturated fatty acid chains such as kokum fat, trilaurin, trimyristin, tripalmitin, tristearin, dodecanoic acid, tetradecanoic acid, hexadecanoic acid, octadecanoic acid, 12-hydroxyoctadecanoic acid, 12-methyloctadecanoic acid, adipic acid, suberic acid, sebacic acid, and hexacosanoic acid, saturated wax esters including but not limited to stearoyl behenate, and combinations of the foregoing. In a still further aspect, the gelator component comprises a combination of components, such as stearic acid and stearyl alcohol, lecithin and sorbitan tristearate, and β-sitosterol and γ-oryzanol. In a still further aspect, the gelator is ethyl cellulose.

In a further aspect, the gelator comprises one or more peptide, polypeptide or protein. In a yet further aspect, the gelator comprises one or more peptide. In a yet further aspect, the gelator comprises one or more polypeptide. In an even further aspect, the gelator comprises one or more protein.

In a further aspect, the oil phase comprises of an oil or a mixture of oils with melting point higher than the temperature in the vitreous humor. In some case, an oil phase comprising an oil or a mixture of oils with melting point higher than the temperature in the vitreous humor may not require a gelator in order to retain the cylindrical structure of the drug delivery composition following administration. In some aspects, an oil phase comprising an oil or a mixture of oils with melting point higher than the temperature in the vitreous humor does not comprise a gelator. In an alternative aspect, an oil phase comprising an oil or a mixture of oils with melting point higher than the temperature in the vitreous humor comprises a gelator.

Exemplary ethylcelluloses that can be used in the process of the present invention include ETHOCEL™ Std. 4, ETHOCEL™ Std. 7, ETHOCEL™ Std. 10, ETHOCEL™ Std. 14, ETHOCEL™ Std. 20, and ETHOCEL™ Std. 45 (which are all commercially available from Dow Chemical Company, Midland, Mich.). Combinations of the exemplary ethylcelluloses can also be used. The level of gelling provided by the ethylcellulose in the oleogel is a function of the proportion of ethylcellulose employed as well as the grade of the ethylcellulose, as is known to those skilled in the art.

Although a surfactant is not necessary to prepare the disclosed oleogels, it can be optionally added in certain aspects to modify the properties of the oleogel, such as to increase its firmness and/or alter dissolution rates, and/or stabilize the water drops in the oleogel. Examples of surfactant that can be used in the disclosed oleogels are pharmaceutically acceptable surfactants and emulsifiers such as polyoxyethylene sorbitan monooleate (Tween 80 or Polysorbate 80); polyoxyethylene sorbitan tristearate (Tween 65 or Polysorbate 65); polyoxyethylene sorbitan monostearate (Tween 60 or Polysorbate 60); sorbitan monooleate (SMO or Span 80); sorbitan monostearate (SMS or Span 60); glyceryl monooleate (GMO); glyceryl monostearate (GMS); glyceryl monopalmitate (GMP); polyglycerol esters such as polyglyceryl ester of lauric acid-polyglyceryl polylaurate (PGPL), polyglyceryl ester of stearic acid-polyglyeryl polystearate (PGPS), polyglyceryl ester of oleic acid-polyglyceryl polyoleate (PGPO) and polyglyceryl ester of ricinoleic acid-polyglyceryl polyricinoleate (PGPR); diglycerides; monoglycerides, such as succinylated monoglyceride, lactylated monoglyceride, acetylated monoglyceride, monoglyceride citrate, monoglyceride phosphate, stearyl monoglyceride citrate, and diacetyl-tartrate ester of monoglyceride; calcium stearoyl lactylate; sodium stearoyl lactylate; sucrose esters; lecithin; and triethyl citrate. In some aspects, the disclosed oleogel does not contain any emulsifier or surfactant, i.e., no emulsifier or surfactant is added during preparation.

In various aspects, an optional surfactant or emulsifier can be an anionic surfactants including, but not limited to, sodium and potassium salts of straight-chain fatty acids, polyoxyethylenated fatty alcohol carboxylates, linear alkyl benzene sulfonates, alpha olefin sulfonates, sulfonated fatty acid methyl ester, arylalkanesulfonates, sulfosuccinate esters, alkyldiphenylether(di)sulfonates, alkylnaphthalenesulfonates, isoethionates, alkylether sulfates, sulfonated oils, fatty acid monoethanolamide sulfates, polyoxyethylene fatty acid monoethanolamide sulfates, aliphatic phosphate esters, nonylphenolphosphate esters, sarcosinates, fluorinated anionics, anionic surfactants derived from oleochemicals, and combinations of any thereof.

In various aspects, an optional surfactant or emulsifier can be an non-anionic surfactants including, but not limited to, sorbitan monostearate, polyoxyethylene ester of rosin, polyoxyethylene dodecyl mono ether, polyoxyethylene-polyoxypropylene block copolymer, polyoxyethylene monolaurate, polyoxyethylene monohexadecyl ether, polyoxyethylene monooleate, polyoxyethylene mono(cis-9-octadecenyl) ether, polyoxyethylene monostearate, polyoxyethylene monooctadecyl ether, polyoxyethylene dioleate, polyoxyethylene distearate, polyoxyethylene sorbitan monolaurate polyoxyethylene sorbitan monooleate, polyoxyethylene sorbitan monopalmitate, polyoxyethylene sorbitan monostearate, polyoxyethylene sorbitan trioleate, polyoxyethylene sorbitan tristearate, polyglycerol ester of oleic acid, polyoxyethylene sorbitol hexastearate, polyoxyethylene monotetradecyl ether, polyoxyethylene sorbitol hexaoleate, fatty acids, tall-oil, sorbitol hexaesters, ethoxylated castor oil, ethoxylated soybean oil, rapeseed oil ethoxylate, ethoxylated fatty acids, ethoxylated fatty alcohols, ethoxylated polyoxyethylene sorbitol tetraoleate, glycerol and polyethylene glycol mixed esters, alcohols, polyglycerol esters, monoglycerides, sucrose esters, alkyl polyglycosides, polysorbates, fatty alkanolamides, polyglycol ethers, derivatives of any thereof, and combinations of any thereof.

In some aspects, the disclosed drug delivery composition is formulated with a first therapeutic agent and a second therapeutic agent, wherein each of the first therapeutic agent and second therapeutic agent are independently selected from a comprise multiple therapeutic agents that can target different aspects of a single clinical condition and/or multiple therapeutic agents that each target a distinct clinical condition. In a further aspect, the second drug ameliorates a side effect or the deleterious effect of the first drug. For example, a glaucoma drug could be included to eliminate an intraocular pressure increase that can follow an intravitreal injection.

In various aspects, the oil phase can be a drug or a nutraceutical such as vitamin E. In a further aspect, the oil phase contains a plurality of oil types. In a still further aspect, the oil phase comprises a first oil and a second oil, wherein each oil is independently selected from a disclosed oil. For example, a first oil can be selected to minimize the solubility of a given drug in the oil mixture such that the given drug is present as particles, and the second oil chosen to improve the gelling properties of the composition.

In various aspects, a disclosed drug delivery composition, i.e., an oleogel, is at an elevated temperature, then cooled to a suitable temperature sufficient to mitigate or avoid degradation of the therapeutic agent that is added, but still sufficiently elevated to allow good mixing of the drug particles. In another aspect, the oleogel prepared drug is allowed to cool and then, in a second step, is melted just above a melting temperature of the oleogel to allow incorporation of a therapeutic agent. In a still further aspect, the oil phase and gelator are selected to achieve a melting point slightly above the physiological temperature.

In some aspects, the oil in the oil phase has a limited solubility in vitreous humor. In a further aspect, the solubility of an oil in the vitreous humor is attenuated in order to provide modulate time durations for a drug delivery composition in the vitreous. Alternatively, the residence time or duration in the vitreous humor can be modulated by varying the concentration of gelator and/or drug concentration.

The drug loading levels achieved in the example described herein below for dexamethasone are comparable to that for currently commercialized drug delivery compositions for retinal delivery. The data suggest that the solubility limit of a drug in the oil phase is an important parameter in the overall kinetics of drug release from the disclosed drug delivery compositions. Accordingly, choice of a specific oil in a disclosed drug delivery composition can be used to modulate the rate of drug release and the period of extend release. In some aspects, if an oil with low solubility is not a good choice for gelation, then a mixture of oils can be used wherein a first oil can be chosen based on solubility criterion associated with the particular drug desired for the composition and a second oil chosen to maximize gelation of the drug delivery composition. The choice of oil(s) used in the drug delivery composition can be important to achieve the desired dissolution profile of a drug delivery composition in situ in the vitreous of an eye following injection. In some aspects, it may be useful for a drug delivery composition comprising a drug to degrade or dissolve via a process that involves gradual dissolution of the oil phase into the vitreous, followed by clearance of the solvated oil phase from the vitreous. Accordingly, in such instances, it may be useful to utilize a drug delivery composition comprising an oil with a low, but finite solubility, in the vitreous environment.

In various aspects, the choice and concentration of the gelator can be important to ensure biocompatibility and also maintain the integrity of an injected gel after injection into the eye. It was observed that drugs that dissolve into the oil phase tend to have an unfavorable effect on the gelation. This effect can be considered in when choosing the concentration of the gelator. It may be useful, in some instances, to inject a drug delivery composition comprising a drug that can change shape slowly after injection into a sphere. Without wishing to be bound by a particular theory, it is possible that an increase in diameter associated with a spherical geometry would provide an extended release of drug compared to the initial cylindrical geometry (with a smaller overall diameter).

In a further aspect, the injected drug delivery composition can be drug in oil without a gelator. Injection of such a drug delivery composition could provide from the outset a drug loaded sphere, which would provide a slower release of drug compared to a cylindrical geometry, which is associated with a composition comprising a gelator.

In other aspects, the density of a drug delivery composition can be an important factor differences in the relative motion of the drug delivery compositions after injection. For example, a lower density drug delivery composition could result in greater movement in the vitreous and lead to greater interference with the vision. In some aspects, the optimized drug delivery composition would have minimal movement in the vitreous after injection. In a further aspect, incorporation of a surfactant, drug and gelators can increase the oil density in the drug delivery composition, thereby reducing or eliminating rising or buoyancy of the drug delivery composition. In various aspects, the density of an injected drug delivery composition is sufficiently high to provide slow settling of the composition in the vitreous following injection.

Release profiles shown may differ from the expected theoretical values due to other factors as well. The differences in diffusivity of the drug in the oleogel after the particles have dissolved may cause a shift in release times. The particle dissolution will create voids that could be filled either by deformation of the gel or by diffusion of the oil into the voids, which would reduce the effective diffusivity. Alternatively, particle dissolution will cause shrinking of the gel, which would also lead to faster release.

In one aspect, the disclosure relates to a drug delivery composition or drug delivery device comprising an emulsified oleogel composition, wherein the continuous phase oleogel comprises one or more oils and gelator, and the dispersed phase comprises water drops stabilized by a surfactant. In a further aspect, the disclosed emulsified oleogel composition further comprises one or more therapeutic agents. The disclosed emulsified oleogel compositions are relatively cheap and easy to prepare, offer stability to emulsions and other liquid based drug systems, can be thermoreversible, can be resistant to microbial contaminates, and can be formulated with both hydrophilic and hydrophobic drugs. The disclosed emulsified oleogel compositions provide for controlled release of ophthalmic formulations, both for the front and the back of the eye. In some aspects, the disclosed emulsified oleogel compositions can be used for delivery of a therapeutic agent to the back eye via injection of a drug-loaded composition into the vitreous.

The disclosed emulsified oleogel compositions can retain a given shape or geometry, such as a cylindrical or spherical geometry, after injection into the vitreous. In some aspects, the disclosed emulsified oleogel compositions have a high viscosity. In some instances, the high viscosity of the emulsified oleogel facilitates maintenance of the initial shape or geometry following injection. In a further aspect, the slow dissolution of an oil in the oleogel will eventually lead to degradation of the injected emulsified oleogel composition.

In a further aspect, an emulsified oleogel composition comprises a dispersed water phase present in an amount from about 0.1 wt % to about 25 wt % based on the weight of the one or more oils and the gelator.

In a further aspect, a disclosed emulsified oleogel composition comprises a dispersed water phase, based on the weight of the one or more oils and the gelator, of about 0.1 wt %, 0.2 wt %, 0.3 wt %, 0.4 wt %, 0.5 wt %, 0.6 wt %, 0.7 wt %, 0.8 wt %, 0.9 wt %, 1.0 wt %, about 1.1 wt %, 1.2 wt %, 1.3 wt %, 1.4 wt %, 1.5 wt %, 1.6 wt %, 1.7 wt %, 1.8 wt %, 1.9 wt %, 2.0 wt %, about 2.1 wt %, 2.2 wt %, 2.3 wt %, 2.4 wt %, 2.5 wt %, 2.6 wt %, 2.7 wt %, 2.8 wt %, 2.9 wt %, 3.0 wt %, about 3.1 wt %, 3.2 wt %, 3.3 wt %, 3.4 wt %, 3.5 wt %, 3.6 wt %, 3.7 wt %, 3.8 wt %, 3.9 wt %, 4.0 wt %, about 4.1 wt %, 4.2 wt %, 4.3 wt %, 4.4 wt %, 4.5 wt %, 4.6 wt %, 4.7 wt %, 4.8 wt %, 4.9 wt %, 5.0 wt %, about 5.1 wt %, 5.2 wt %, 5.3 wt %, 5.4 wt %, 5.5 wt %, 5.6 wt %, 5.7 wt %, 5.8 wt %, 5.9 wt %, 6.0 wt %, about 6.1 wt %, 6.2 wt %, 6.3 wt %, 6.4 wt %, 6.5 wt %, 6.6 wt %, 6.7 wt %, 6.8 wt %, 6.9 wt %, 7.0 wt %, about 7.1 wt %, 7.2 wt %, 7.3 wt %, 7.4 wt %, 7.5 wt %, 7.6 wt %, 7.7 wt %, 7.8 wt %, 7.9 wt %, 8.0 wt %, about 8.1 wt %, 8.2 wt %, 8.3 wt %, 8.4 wt %, 8.5 wt %, 8.6 wt %, 8.7 wt %, 8.8 wt %, 8.9 wt %, 9.0 wt %, about 9.1 wt %, 9.2 wt %, 9.3 wt %, 9.4 wt %, 9.5 wt %, 9.6 wt %, 9.7 wt %, 9.8 wt %, 9.9 wt %, 10 wt %, 10.5 wt %, 11 wt %, 11.5 wt %, 12 wt %, 12.5 wt %, 13 wt %, 13.5 wt %, 14 wt %, 14.5 wt %, 15 wt %, 15.5 wt %, 16 wt %, 16.5 wt %, 17 wt %, 17.5 wt %, 18 wt %, 18.5 wt %, 19 wt %, 19.5 wt %, 20 wt %, 20.5 wt %, 21 wt %, 21.5 wt %, 22 wt %, 22.5 wt %, 23 wt %, 23.5 wt %, 24 wt %, 24.5 wt %, 25 wt %; a range encompassed by any of the foregoing values; or a set of any of the foregoing values.

In a further aspect, the surfactant in a disclosed emulsified oleogel composition can comprise a suitable surfact, such as, but not limited to, a poloxamer. Poloxamers are sometimes referred to as a Pluronic® polymer or material, e.g., Pluronic F-127 ($PEO_{100}PPO_{64}PEO_{100}$, MW 12,450 Da. 70 wt % PEO), also known as Poloxamer 407, or Pluronic P123 ($PEO_{20}PPO_{70}PEO_{20}$, MW 5750 Da, 30 wt % PEO). Exemplary poloxamers include tri-block copolymers of hydrophilic poly(ethylene oxide) blocks and hydrophobic poly(propylene oxide)-blocks giving a tri-block polymer of PEO-PPO-PEO structure.

In a further aspect, the surfactant in a disclosed emulsified oleogel composition is present in an amount from about 0.1 wt %, 0.2 wt %, 0.3 wt %, 0.4 wt %, 0.5 wt %, 0.6 wt %, 0.7 wt %, 0.8 wt %, 0.9 wt %, 1.0 wt %, about 1.1 wt %, 1.2 wt %, 1.3 wt %, 1.4 wt %, 1.5 wt %, 1.6 wt %, 1.7 wt %, 1.8 wt %, 1.9 wt %, 2.0 wt %, about 2.1 wt %, 2.2 wt %, 2.3 wt %, 2.4 wt %, 2.5 wt %, 2.6 wt %, 2.7 wt %, 2.8 wt %, 2.9 wt %, 3.0 wt %, about 3.1 wt %, 3.2 wt %, 3.3 wt %, 3.4 wt %, 3.5 wt %, 3.6 wt %, 3.7 wt %, 3.8 wt %, 3.9 wt %, 4.0 wt %, about 4.1 wt %, 4.2 wt %, 4.3 wt %, 4.4 wt %, 4.5 wt %, 4.6 wt %, 4.7 wt %, 4.8 wt %, 4.9 wt %, 5.0 wt %, about 5.1 wt %, 5.2 wt %, 5.3 wt %, 5.4 wt %, 5.5 wt %, 5.6 wt %, 5.7 wt %, 5.8 wt %, 5.9 wt %, 6.0 wt %, about 6.1 wt %, 6.2 wt %, 6.3 wt %, 6.4 wt %, 6.5 wt %, 6.6 wt %, 6.7 wt %, 6.8 wt %, 6.9 wt %, 7.0 wt %, about 7.1 wt %, 7.2 wt %, 7.3 wt %, 7.4 wt %, 7.5 wt %, 7.6 wt %, 7.7 wt %, 7.8 wt %, 7.9 wt %, 8.0 wt %, about 8.1 wt %, 8.2 wt %, 8.3 wt %, 8.4 wt %, 8.5 wt %, 8.6 wt %, 8.7 wt %, 8.8 wt %, 8.9 wt %, 9.0 wt %, about 9.1 wt %, 9.2 wt %, 9.3 wt %, 9.4 wt %, 9.5 wt %, 9.6 wt %, 9.7 wt %, 9.8 wt %, 9.9 wt %, 10 wt %, 10.5 wt %, 11 wt %, 11.5 wt %, 12 wt %, 12.5 wt %, 13 wt %, 13.5 wt %, 14 wt %, 14.5 wt %, 15 wt %; a range encompassed by any of the foregoing values; or a set of any of the foregoing values.

It is understand herein throughout, an oleogel composition and an emulsified oleogel composition can be used interchangeably in most aspects, e.g., with regard to further comprising of one or more therapeutic agents, the one or more oils therein, the gelator therein, or in a method of using a disclosed oleogel. It is understood that although an oleogel composition and an emulsified oleogel composition can be used interchangeably in most aspects, they may differ in particular aspects of the method of preparing an oleogel comprising an oil phase and a gelator versus preparing an emulsified oleogel.

C. Devices for the Disclosed Drug Delivery Compositions

Figure 29A:
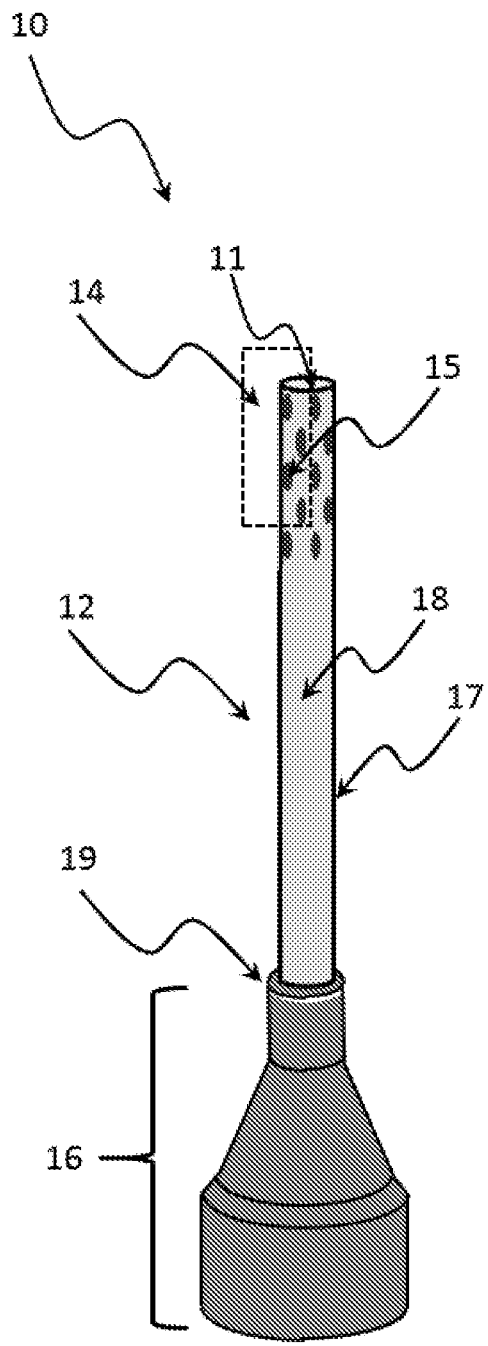
FIGS. 29A-29C shows a cross-sectional schematic diagram of a representative disclosed needle, 10, comprising a plurality of exit openings, 15.
Figure 29B:
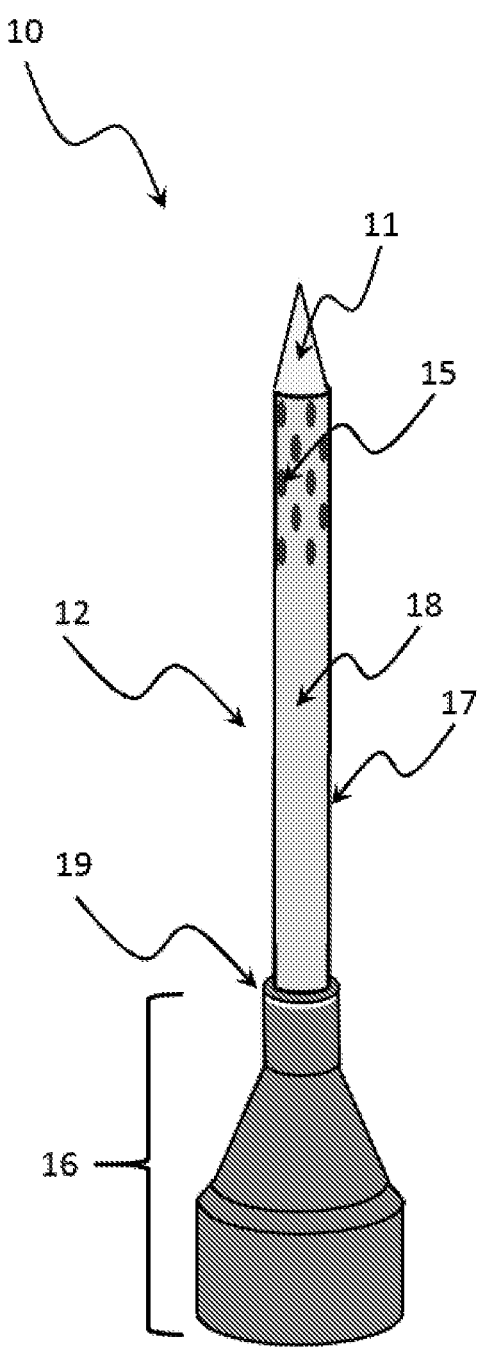
Figure 29C:
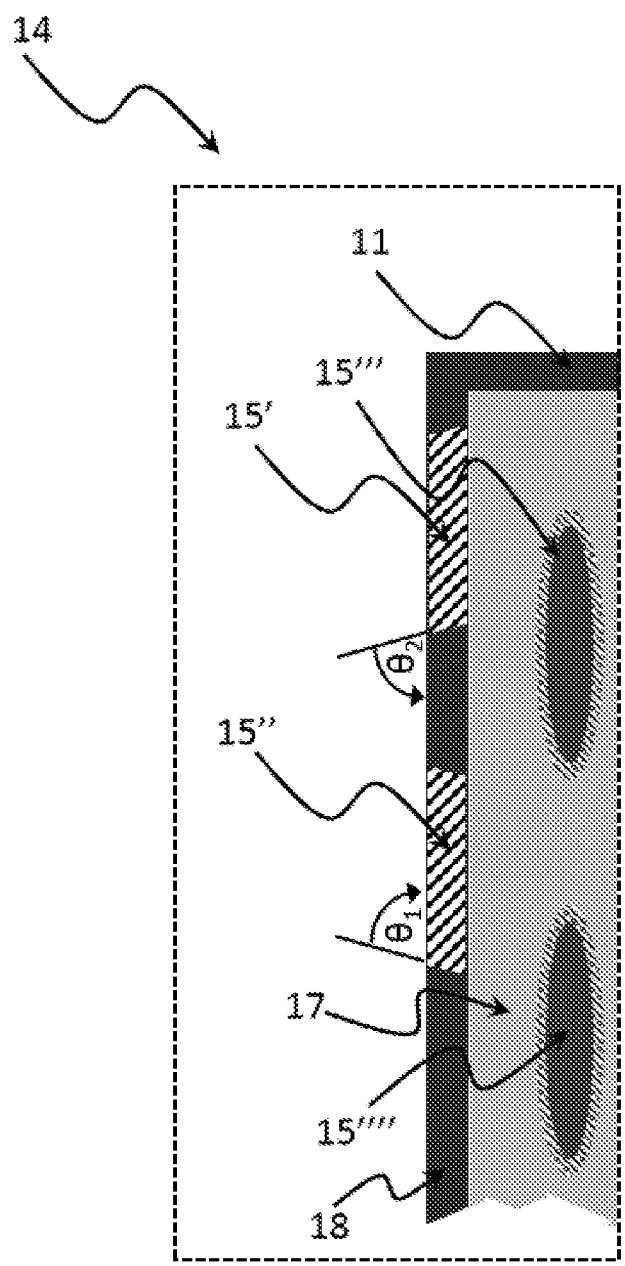

In an aspect, it may be useful to provide a disclosed drug delivery composition via device that comprises a needle 10 that comprises a plurality of openings 15 as shown in FIGS. 29A and 29B. FIG. 29C shows a detail of a portion of the needle 14, showing that the openings can be independently oriented with regarding to the angle of the opening, such as $\theta_1$ and $\theta_2$, relative the normal of the surface of the needle 18. A needle comprising a plurality of openings may have a blunt surface as shown in FIG. 29A, or alternatively, an angled surface narrowing to a point, as shown in FIG. 29B.

Figure 31A:
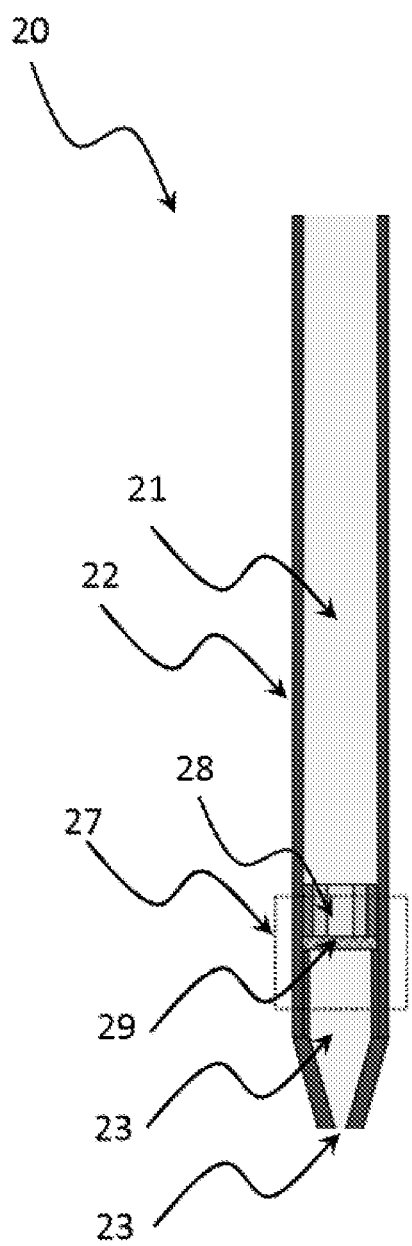
FIGS. 31A-31B shows a cross-sectional schematic diagram of a representative disclosed drug delivery device, 20, that is configured with a plurality of drug delivery compositions, 28, to provide pulsatile drug release.
Figure 31B:
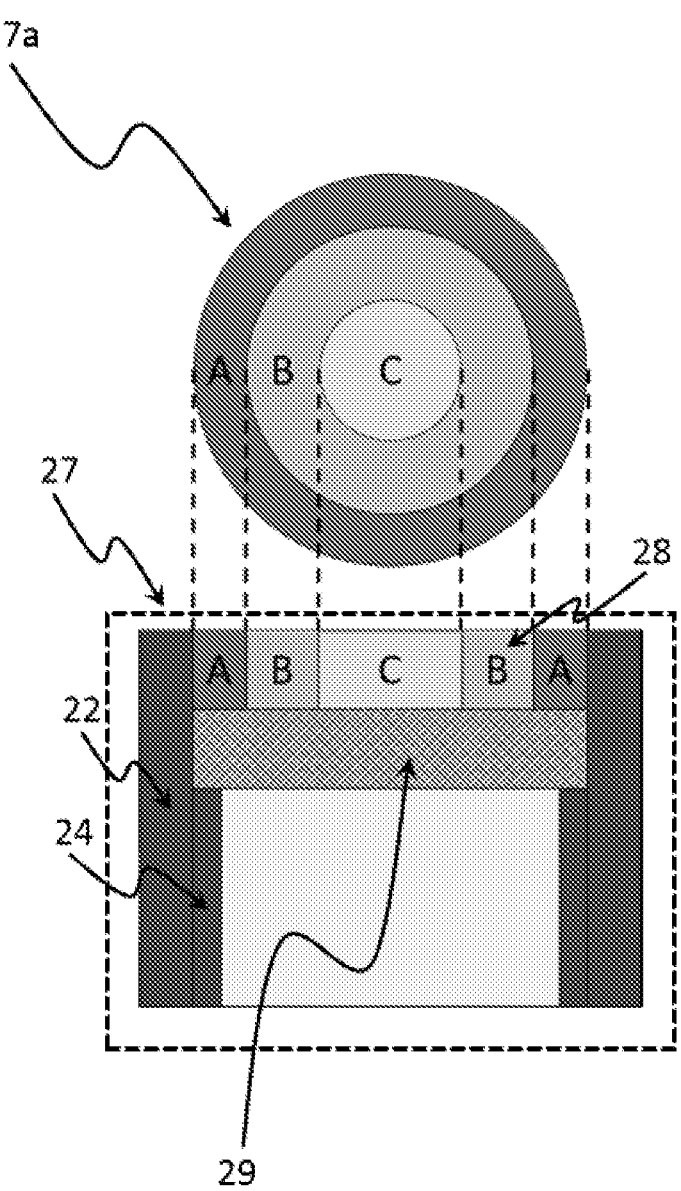
Figure 32:
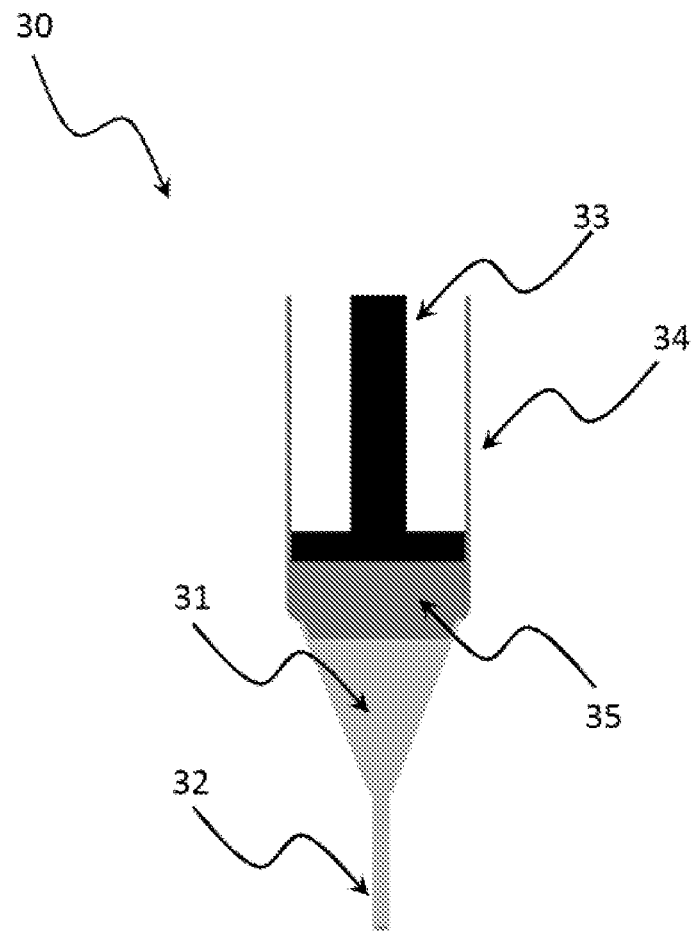
FIG. 32 shows a cross-sectional schematic diagram of a representative disclosed drug delivery device, 30, that comprises an inner needle plunger component, 34, configured to comprise a portion that is capable of entering the inner portion of a needle as shown. The inner needle plunger component facilitates maximum utilization of a drug delivery composition comprising a therapeutic agent by minimizing the amount of the drug delivery composition comprising a therapeutic agent that remains in the needle tip.

In an aspect, it may be useful to provide a disclosed drug delivery composition via device that can provide offer pulsatile drug release profile. That is, a device that instead of continuous release provides a first period of drug release during which a certain amount of drug is released, followed by a latency period of time during which significantly decreased amounts of drug are released, and then release of additional drug during a second period of drug release. Clearly, multiple cycles of drug release and latency periods are contemplated by the present disclosure. In some aspects, disclosed are devices for pulsatile release from an injected oleogel based device. This approach could also be used to combine different types of drugs as well. FIGS. 31A and 31B provide schematic representations of a disclosed pulsatile drug release device. In the aspect shown in FIGS. 31A and 31B, there are three different hypothetical therapeutic agents (shown as A, B, and C therein) utilized that are configured in three different layers of an oleogel composition.

The disclosed device works by releasing drug from the outside to the inside. That is, when the multi-layer composition is ejected via the syringe opening, Drug A would release first which would cause that layer to break down, and then drug B would release, followed by the core layer made up of C. The disclosed device is merely one simplified aspect of a pulsatile delivery device. In various aspects, the different oleogel layers could be changed such that there are more layers, or to include a layer of no drug release at all. As shown in the figure, there is a porous structure which allows for the different layers to be gelled into place without mixing. This porous structure can be held in place by supports on the walls of the syringe. The device can then be pushed through the porous layer using pressure induced by the syringe plunger. This approach can also be used to further increase the drug release duration by choosing the outer layer that has very low permeability for the drug of interest.

Figure 33:
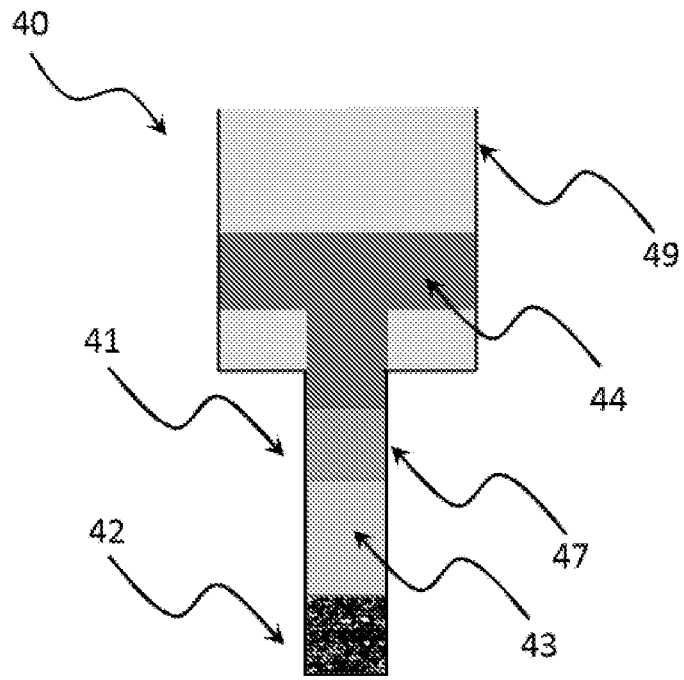
FIG. 33 shows a cross-sectional schematic diagram of a representative disclosed drug delivery device, 40, that comprises a plurality of layers such that one layer, 41, comprises a drug delivery composition comprising a therapeutic agent is overlaid with a layer, 47, comprising a drug delivery composition without the therapeutic agent. The drug delivery device optimizes delivery of therapeutic agent to the target region of the eye with minimal wastage of the drug delivery composition comprising therapeutic agent left unused and remaining in the needle tip.

In various aspects, the present disclosure pertains to a drug delivery device that maximizes delivery of an oleogel from a device. FIG. 31 shows an exemplary aspect of a drug delivery device, 30, that comprises a syringe comprising a disclosed oleogel comprising a drug formulation gel, 31, with an additional oleogel without drug, 35, overlaying the oleogel comprising a drug formulation. Alternatively, a disclosed drug delivery device that maximizes delivery of an oleogel from a device is show in FIG. 33 in a cross-sectional view of a portion of a device comprising a syringe and needle, 40. The device, 40, comprises a syringe and needle system, in which the plunger proceeds through the syringe body all the way into the needle. The device, 40, can deliver a disclosed oleogel comprising a therapeutic agent in a manner that minimizes the amount of residual oleogel with therapeutic agent in the syringe barrel. That is, the plunger, 44, is configure to enter the hollow cavity of a needle and contact an oleogel in the needle, thereby pushing the oleogel from the needle. Accordingly, the injection can comprise essentially only the amount of oleogel with drug that is minimally required for the desired injection. Also shown in FIG. 33 are a plunger seal, 47; a porous needle tip, 42; an oleogel comprising at least one therapeutic agent, 43; and a wall of the syringe, 49.

In some instances, an intravitreal injection is associated with a rapid increase in intraocular pressure (1OP) due to procedures. In some aspects, in order to mitigate the increase in 1OP, disclosed are drug delivery devices comprising a syringe and needle mechanism which simultaneously draws in an equivalent amount of fluid as the amount of gel which is injected into the vitreous. For example, this can be accomplished using a needle comprising a porous needle tip, 42, as shown in FIG. 33. The porous needle tip, 42, provides absorption of aqueous fluid as the needle plunger is pushed down during ejection of the oleogel comprising a therapeutic agent.

In various aspects, a disclosed drug delivery device provides reduced friction during ejection of a disclosed oleogel comprising a therapeutic agent. The disclosed oleogels are semisolid, and thuys the amount of force needed to eject the oleogel through a needle is higher than that of a fluid based drug formulation. In various aspects, a disclosed drug delivery device comprises a needle with a coating of a lubricious material on the interior surface of the needle that will be in contact with oleogel composition as it pushed through the needle during ejection. The lubricity would allow the gel to glide on the surface, and reduce the amount of force required to expunge the device. The lubricious layer can be coated such that thickness is from about 10 nm to about 10 μm.

In various aspects, a disclosed drug delivery device injected into the vitreous can be preferably degraded naturally after release of the one or more therapeutic agents. The disclosed drug delivery device disclosed here can degrade through multiple mechanisms including the following: (a) dissolution of the oil and the geltor into vitreous; (b) degradation of gelator leading to conversion of the oileogel to oil, followed by dissolution of the oil; and/or (c) degradation of the oil into more soluble components. Without wishing to be bound by a particular theory, in the instance wherein the disclosed drug delivery device comprises a gelator that is ethyl cellulose, it is believed that ethyl cellulose would not degrade, and according, the disclosed drug delivery device will likely degrade via slow dissolution of the oil. Further, without wishing to be bound by a particular theory, it is believed that dissolution of oil can be accelerated by incorporation of surfactants into the formulation that form micelles after dissolving in vitreous, thus allowing dissolution of the oil into the core of the micelles. In various aspects, in order to accelerate degradation of a disclosed drug delivery device, it may be preferable to formulate the oleogel such that the melting point of the gel is only slightly higher than the temperature in the vitreous. Drug, surfactant, and gelator types and loadings, as well as the oil type can be adjusted to obtain the desired degradation rates.

D. Therapeutic Agents

In various aspects, a disclosed drug delivery composition can comprise a therapeutic agent, such as a drug or a biological, including an antibody therapeutic or therapeutic protein. The therapeutic agent can be any therapeutic agent useful to treat a disease or disorder of the eye. In a further aspect, the therapeutic agent is a tyrosine kinase inhibitor, an antihistamine, an antibiotic, a beta blocker, a steroid, an antineoplastic agent, an antiviral, an immunosuppressive agent, an antioxidant, and combinations thereof. The disclosed drug delivery compositions, e.g., a disclosed oleogel, can be loaded with a variety of agents, including hydrophobic and hydrophilic drugs, at high drug loading concentrations.

In various aspects, a disclosed drug delivery composition can comprise a therapeutic agent, such that the therapeutic agent is present in an amount from about 5 wt % to about 50 wt % based on the weight of the one or more oils, the gelator, and the therapeutic agent. In a further aspect, the therapeutic agent is present in an amount of about 5 wt %, 5.5 wt %, 6 wt %, 6.5 wt %, 7 wt %, 7.5 wt %, 8 wt %, 8.5 wt %, 9 wt %, 9.5 wt %, 10 wt %, 10.5 wt %, 11 wt %, 11.5 wt %, 12 wt %, 12.5 wt %, 13 wt %, 13.5 wt %, 14 wt %, 14.5 wt %, 15 wt %, 15.5 wt %, 16 wt %, 16.5 wt %, 17 wt %, 17.5 wt %, 18 wt %, 18.5 wt %, 19 wt %, 19.5 wt %, 20 wt %, 20.5 wt %, 21 wt %, 21.5 wt %, 22 wt %, 22.5 wt %, 23 wt %, 23.5 wt %, 24 wt %, 24.5 wt %, 25 wt %, 25.5 wt %, 26 wt %, 26.5 wt %, 27 wt %, 27.5 wt %, 28 wt %, 28.5 wt %, 29 wt %, 29.5 wt %, 30 wt %, 30.5 wt %, 31 wt %, 31.5 wt %, 32 wt %, 32.5 wt %, 33 wt %, 33.5 wt %, 34 wt %, 34.5 wt %, 35 wt %, 35.5 wt %, 36 wt %, 36.5 wt %, 37 wt %, 37.5 wt %, 38 wt %, 38.5 wt %, 39 wt %, 39.5 wt %, 40 wt %, 40.5 wt %, 41 wt %, 41.5 wt %, 42 wt %, 42.5 wt %, 43 wt %, 43.5 wt %, 44 wt %, 44.5 wt %, 45 wt %, 45.5 wt %, 46 wt %, 46.5 wt %, 47 wt %, 47.5 wt %, 48 wt %, 48.5 wt %, 49 wt %, 49.5 wt %, 50 wt %; a range encompassed by any of the foregoing values; or a set of any of the foregoing values.

In a further aspect, a disclosed drug delivery composition can comprise a therapeutic agent, such that the therapeutic agent is selected from one or more of cyclosporine A, dexamethasone, metformin, timolol, triamcinolone, vancomycin, and pharmaceutically acceptable salts thereof In a further aspect, a disclosed drug delivery composition comprises an tyrosine kinase inhibitor selected from axitinib, cabozantinib, foretinib, regorafenib, pazopanib, ponatinib, motesanib, cediranib, tivozanib, sorafenib, LY2457546, MGCD-265, MGCD-510, pharmaceutically acceptable salts thereof, and any combination of the foregoing. In other aspects, the tyrosine kinase inhibitor is a derivator of the foregoing tyrosine kinase inhibitors.

In a further aspect, a disclosed drug delivery composition comprises an antihistamine selected from loradatine, hydroxyzine, diphenhydramine, chlorpheniramine, brompheniramine, cyproheptadine, terfenadine, clemastine, triprolidine, carbinoxamine, diphenylpyraline, phenindamine, azatadine, tripelennamine, dexchlorpheniramine, dexbrompheniramine, methdilazine, trimprazine doxylamine, pheniramine, pyrilamine, chiorcyclizine, thonzylamine, and pharmaceutically acceptable salts thereof, and combinations of any of the foregoing. In some aspects, the antihistamine is a derivative of one of the foregoing compounds.

In a further aspect, a disclosed drug delivery composition comprises an antibiotic selected from cefazolin, cephradine, cefaclor, cephapirin, ceftizoxime, cefoperazone, cefotetan, cefutoxime, cefotaxime, cefadroxil, ceftazidime, cephalexin, cephalothin cefamandole, cefoxitin, cefonicid, ceforanide, ceftriaxone, cefadroxil, cephradine, cefuroxime, cyclosporine, ampicillin, amoxicillin, cyclacillin, ampicillin, penicillin G, penicillin V potassium, piperacillin, oxacillin, bacampicillin, cloxacillin, ticarcillin, azlocillin, carbenicillin, methicillin, nafcillin, erythromycin, tetracycline, doxycycline, minocycline, aztreonam, chloramphenicol, ciprofloxacin hydrochloride, clindamycin, metronidazole, gentamicin, lincomycin, tobramycin, vancomycin, polymyxin B sulfate, colistimethate, colistin, azithromycin, augmentin, sulfamethoxazole, trimethoprim, gatifloxacin, ofloxacin, and pharmaceutically acceptable salts thereof, and combinations of any of the foregoing. In some aspects, the antibiotic is a derivative of one of the foregoing compounds.

In a further aspect, a disclosed drug delivery composition comprises an antiviral selected from interferon gamma, zidovudine, amantadine hydrochloride, ribavirin, acyclovir, valciclovir, dideoxycytidine, phosphonoformic acid, ganciclovir, and pharmaceutically acceptable salts thereof, and combinations of any of the foregoing. In some aspects, the antiviral is a derivative of one of the foregoing compounds.

In a further aspect, a disclosed drug delivery composition comprises a beta blocker selected from acebutolol, atenolol, labetalol, metoprolol, propranolol, timolol, and pharmaceutically acceptable salts thereof, and combinations of any of the foregoing. In some aspects, the beta blocket is a derivative of one of the foregoing compounds.

In a further aspect, a disclosed drug delivery composition comprises a steroid, including a corticosteroid, selected from cortisone, prednisolone, flurometholone, dexamethasone, medrysone, loteprednol, fluazacort, hydrocortisone, prednisone, betamethasone, prednisone, methylprednisolone, riameinolone hexacatonide, paramethasone acetate, diflorasone, fluocinonide, fluocinolone, triamcinolone, and pharmaceutically acceptable salts thereof, and combinations of any of the foregoing. In some aspects, the steroid is a derivative of one of the foregoing compounds.

In a further aspect, a disclosed drug delivery composition comprises an antineoplastic agent selected from adriamycin, cyclophosphamide, actinomycin, bleomycin, duanorubicin, doxorubicin, epirubicin, mitomycin, methotrexate, fluorouracil, carboplatin, carmustine (BCNU), methyl-CCNU, cisplatin, etoposide, interferons, camptothecin and derivatives thereof, phenesterine, taxol, taxotere, vinblastine, vincristine, tamoxifen, etoposide, piposulfan, cyclophosphamide, flutamide, and pharmaceutically acceptable salts thereof, and combinations of any of the foregoing. In some aspects, the antineoplastic agent is a derivative of one of the foregoing compounds.

In a further aspect, a disclosed drug delivery composition comprises an immunosuppressive agent selected from voclosporin, cyclosporine, azathioprine, tacrolimus, and pharmaceutically acceptable salts thereof, and combinations of any of the foregoing. In some aspects, the immunosuppressive agent is a derivative of one of the foregoing compounds.

In a further aspect, a disclosed drug delivery composition comprises an antioxidant selected from ascorbate, alpha-tocopherol, mannitol, reduced glutathione, various carotenoids, cysteine, uric acid, taurine, tyrosine, superoxide dismutase, lutein, zeaxanthin, cryotpxanthin, astazanthin, lycopene, N-acetyl-cysteine, carnosine, gamma-glutamyl-cysteine, quercitin, lactoferrin, dihydrolipoic acid, citrate, *Ginkgo Biloba* extract, tea catechins, bilberry extract, vitamins E or esters of vitamin E, retinyl palmitate, and pharmaceutically acceptable salts thereof, and combinations of any of the foregoing. In some aspects, the antioxidant is a derivative of one of the foregoing compounds.

In a further aspect, a disclosed drug delivery composition can comprise other ophthalmological agents. Examples of such other ophthalmological agents include, but are not limited, to carotenoids, such as lycopene, lutein, zeaxanthin, phytoene, phytofluene, carnosic acid; carotenoid derivatives such as carnosol, 6,7-dehydrocarnosic acid, 7-ketocarnosic acid; a zinc source like zinc oxide or a zinc salt like its chloride, acetate, gluconate, carbonate, sulphate, borate, nitrate or silicate salt; copper oxide; vitamin A; vitamin C; vitamin E; β-carotene; and combinations of any of the foregoing.

The disclosed drug delivery composition can comprise a single therapeutic agent or a combination of one or more therapeutic agents. "Combination" means for the purposes of the invention not only a dosage form which contains all the active agents (so-called fixed combinations), and combination packs containing the active agents separate from one another, but also active agents which are administered simultaneously or sequentially, as long as they are employed for the prophylaxis or treatment of the same disease.

In various aspects, a disclosed drug delivery composition comprises a signal transduction inhibitors targeting receptor kinases of the domain families of e.g. VEGFR, PDGFR, FGFR and their respective ligands or other pathway inhibitors like VEGF-Trap (aflibercept), pegaptanib, ranibizumab, sunitinib, ceridanib, pazopanib, bevasiranib, KH-902, mecamylamine, PF-04523655, E-10030, ACU-4429, volociximab, sirolismus, fenretinide, disulfiram, sonepcizumab and/or tandospirone. These agents include, without limitation, antibodies such as Avastin (bevacizumab). These agents also include, by no way of limitation, small-molecule inhibitors such as STI-571/Gleevec (Zvelebil, Curr. Opin. Oncol., Endocr. Metab. Invest. Drugs 2000, 2(1), 74-82), PTK-787 (Wood et al., Cancer Res. 2000, 60(8), 2178-2189), ZD-6474 (Hennequin et al., 92nd AACR Meeting, New Orleans, Mar. 24-28, 2001, abstract 3152), AG-13736 (Herbst et al., Clin. Cancer Res. 2003, 9, 16 (suppl 1), abstract C253), KRN-951 (Taguchi et al., 95th AACR Meeting, Orlando, Fla., 2004, abstract 2575), CP-547,632 (Beebe et al., Cancer Res. 2003, 63, 7301-7309), CP-673,451 (Roberts et al., Proceedings of the American Association of Cancer Research 2004, 45, abstract 3989), CHIR-258 (Lee et al., Proceedings of the American Association of Cancer Research 2004, 45, abstract 2130), MLN-518 (Shen et al., Blood 2003, 102, 11, abstract 476), and AZD-2171 (Hennequin et al., Proceedings of the American Association of Cancer Research 2004, 45, abstract 4539), PKC412, nepafenac.

In various aspects, a therapeutic agent that can be formulated with a disclosed drug delivery composition is a therapeutic agent disclosed in U.S. Pat. Nos. 4,474,451; 4,327,725; and 8,642,067, each of which is incorporated by reference in its entirety.

E. Methods of Treatment

In various aspects, the present disclosure pertains to methods of treating or preventing a clinical condition. In some aspects, the clinical condition is a disease or disorder of the eye. In a further aspect, the disclosed methods pertain to treatment of an ophthalmological disorder.

Examples of ophthalmological disorders according to the invention include but are not limited to age-related macular degeneration (AMD), choroidal neovascularization (CNV), choroidal neovascular membrane (CNVM), cystoid macula edema (CME), epi-retinal membrane (ERM) and macular hole, myopia-associated choroidal neovascularisation, vascular streaks, retinal detachment, diabetic retinopathy, diabetic macular edema (DME), atrophic changes of the retinal pigment epithelium (RPE), hypertrophic changes of the retinal pigment epithelium (RPE), retinal vein occlusion, choroidal retinal vein occlusion, macular edema, macular edema due to retinal vein occlusion, retinitis pigmentosa, Stargardt's disease, glaucoma, inflammatory conditions of the eye such as e.g. uveitis, scleritis or endophthalmitis, cataract, refractory anomalies such as e.g. myopia, hyperopia or astigmatism and ceratoconus and retinopathy of prematurity. In addition, examples include but are not limited to angiogenesis in the front of the eye like corneal angiogenesis following e.g. keratitis, corneal transplantation or keratoplasty, corneal angiogenesis due to hypoxia (extensive contact lens wearing), pterygium conjunctivae, subretinal edema and intraretinal edema. Examples of age-related macular degeneration (AMD) include but are not limited to dry or nonexudative AMD, or wet or exudative or neovascular AMD. In a further aspect, the ophthalmological disorder is glaucoma. Alternatively, the ophthalmological disorder is retinal ischemia, including either central retinal ischemia or peripheral retinal ischemia.

The eye comprises several structurally and functionally distinct vascular beds, which supply ocular components critical to the maintenance of vision. These include the retinal and choroidal vasculatures, which supply the inner and outer portions of the retina, respectively, and the limbal vasculature located at the periphery of the cornea. Injuries and diseases that impair the normal structure or function of these vascular beds are among the leading causes of visual impairment and blindness. For example, diabetic retinopathy is the most common disease affecting the retinal vasculature, and is the leading cause of vision loss among the working age population in the United States. Vascularization of the cornea secondary to injury or disease is yet another category of ocular vascular disease that can lead to severe impairment of vision.

"Macular degeneration" is a medical term that applies to any of several disease syndromes which involve a gradual loss or impairment of eyesight due to cell and tissue degeneration of the yellow macular region in the center of the retina. Macular degeneration is often characterized as one of two types, non-exudative (dry form) or exudative (wet form). Although both types are bilateral and progressive, each type may reflect different pathological processes. The wet form of age-related macular degeneration (AMD) is the most common form of choroidal neovascularization and a leading cause of blindness in the elderly. AMD affects millions of Americans over the age of 60, and is the leading cause of new blindness among the elderly. It is characterized and usually diagnosed by the presence of elevated levels of two types of cellular debris within the retina, called drusen and lipofuscin.

In a further aspect, the disclosed method pertains to treatment of an ophthalmological disorder selected from the group comprising age-related macular degeneration (AMD), including wet AMD, choroidal neovascularization (CNV), choroidal neovascular membrane (CNVM), cystoid macula edema (CME), epi-retinal membrane (ERM) and macular hole, myopia-associated choroidal neovascularisation, vascular streaks, retinal detachment, diabetic retinopathy, diabetic macular edema (DME), atrophic changes of the retinal pigment epithelium (RPE), hypertrophic changes of the retinal pigment epithelium (RPE), retinal vein occlusion, choroidal retinal vein occlusion, macular edema, macular edema due to retinal vein occlusion, retinitis pigmentosa, Stargardt's disease, glaucoma, inflammatory conditions, cataract, refractory anomalies, ceratoconus, retinopathy of prematurity, angiogenesis in the front of the eye, corneal angiogenesis following keratitis, corneal transplantation or keratoplasty, corneal angiogenesis due to hypoxia (extensive contact lens wearing), pterygium conjunctivae, subretinal edema and intraretinal edema comprising administering a disclosed drug delivery composition comprising a disclosed therapeutic agent. In some aspects, a disclosed method pertains to administering a disclosed drug delivery composition comprising a disclosed therapeutic agent to a subject that has been diagnosed with an opthamlogic disorder. In a further aspect, a disclosed method pertains to administering a disclosed drug delivery composition comprising a disclosed therapeutic agent to a subject that has been diagnosed with one or more of: (i) macular degeneration, (ii) diabetes-related retinopathy, and (iii) pathological vascularization of the cornea secondary to injury or disease.

In a further aspect, the disclosed method pertains to treatment of a posterior eye disease. Examples of posterior eye diseases include but are not limited to age-related macular degeneration (AMD), choroidal neovascularization (CNV), choroidal neovascular membrane (CNVM), cystoid macula edema (CME), epi-retinal membrane (ERM) and macular hole, myopia-associated choroidal neovascularisation, vascular streaks, retinal detachment, diabetic retinopathy, diabetic macular edema (DME), atrophic changes of the retinal pigment epithelium (RPE), hypertrophic changes of the retinal pigment epithelium (RPE), retinal vein occlusion, choroidal retinal vein occlusion, macular edema, macular edema due to retinal vein occlusion, retinitis pigmentosa, Stargardt's disease and retinopathy of prematurity.

In an aspect, the disclosed method comprises an intravitreal injection of a disclosed drug delivery composition comprising a disclosed therapeutic agent. In a further aspect, the disclosed method comprises injection of a disclosed drug delivery composition comprising a disclosed therapeutic agent via a non-intravitreal route, e.g., the method can comprise one or more of subconjunctiva injection, subretinal injection, sub-tenon injection, retrobulbar injection, and suprachoroidal injection of a disclosed drug delivery composition comprising a disclosed therapeutic agent.

In an aspect, the disclosed method comprises injection of a disclosed drug delivery composition comprising a disclosed therapeutic agent near the lower fornix, thereby providing a fornix implant for continuous or nearly continuous delivery of a therapeutic agent via tears of the eye.

In a further aspect, the disclosed method comprises injection of a disclosed drug delivery composition comprising a disclosed therapeutic agent into the canaliculi through the puncta, thereby providing a punctum plug.

In an aspect, the disclosed method comprises a subcutaneous or intramuscular injection another region of the body, e.g., subcutaneous injection in a thigh muscle.

Before proceeding to the Examples, it is to be understood that this disclosure is not limited to particular aspects described, and as such may, of course, vary. Other systems, methods, features, and advantages of foam compositions and components thereof will be or become apparent to one with skill in the art upon examination of the following drawings and detailed description. It is intended that all such additional systems, methods, features, and advantages be included within this description, be within the scope of the present disclosure, and be protected by the accompanying claims. It is also to be understood that the terminology used herein is for the purpose of describing particular aspects only, and is not intended to be limiting. The skilled artisan will recognize many variants and adaptations of the aspects described herein. These variants and adaptations are intended to be included in the teachings of this disclosure and to be encompassed by the claims herein.

F. Examples

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Materials.

Soybean oil (Spectrum Organic Products, LLC, Lake Success, N.Y.) was used as the oil phase for the exemplary oleogel formulations described herein below. The polymer utilized as an exemplary solid component was ethyl cellulose (Sigma-Aldrich Corporation, St. Louis, Mo.). For the exemplary emulsion based gels described herein below, surfactants sorbitan monooleate (Sigma-Aldrich) with an HLB of 4.4 and polysorbate 80 (Sigma-Aldrich) with an HLB of 15.0 were used as surfactants. Phosphate-buffered saline 1× (Fisher Scientific International, Inc., Hampton, N.H.) was used as the aqueous phase in the water in oil emulsions examples described herein below, as well as the release medium for drug release studies. Octanoic acid (Sigma-Aldrich) was acquired for gel formulations that included an oil and octanoic acid mixture. Drugs used in experiments include dexamethasone (Carbosynth US LLC, San Diego, Calif.), vancomycin hydrochloride (Carbosynth US LLC, San Diego, Calif.), metformin hydrochloride (Sigma-Aldrich), dexamethasone sodium phosphate (Carbosynth Limited), dexamethasone acetate (Sigma-Aldrich), cyclosporin (Sigma-Aldrich), triamcinolone (Carbosynth Limited), and timolol maleate (Ven Petrochem & Pharma (India) Pvt. Ltd., Mumbai, India).

2. Preparation of Example Drug Delivery Compositions: Soybean Oil/Ethyl Cellulose Oleogel.

Soybean oil and ethyl cellulose oleogels were prepared for incorporation of mainly hydrophobic drugs. During preparation, the oil was added to a vial at room temperature. Ethyl cellulose powder was added to achieve a mass percent of 10%. This mixture was stirred until the powder evenly dispersed. The vial was then heated to the ethyl cellulose melting temperature (about 160° C.) for 10 minutes, or until all of the ethyl cellulose melted. The melting step was complete when the color of the oil became darker and ethyl cellulose particles were no longer visible. For control experiments with no drug, this mixture with oil and melted ethyl cellulose was set aside to gel at room temperature. To achieve drug loaded gels, the vials were immediately moved to a hot plate set to 90° C. This set temperature was required to keep the mixture in liquid form without decomposing the ethyl cellulose component. While continuing to stir the mixture, drug was slowly added to achieve the desired final mass percent. After the drug was well-mixed, the formulation was poured into a syringe, and cooled at room temperature to form an oleogel. In some instances, the drug delivery composition further comprised octanoic acid. That is, the oleogel was first formed using a mixture of soybean oil and octanoic acid. In some instances, more than one drug was added to a single mixture. If a drug was incorporated into the oleogel, the drug was added to the liquid phase of this gel as described further in specific examples herein below.

3. Preparation of Example Drug Delivery Compositions: Emulsion-Based Oleogels.

Emulsion-based oleogels were prepared for incorporation of mainly hydrophilic drugs. For emulsion based oleogels, a water-in-oil ("W/O") emulsion must first be created. The water component comprised PBS comprising dissolved drug. Oil and sorbitan monooleate were added to a vial at a 3:1 ratio. Tween 80 and the water component were then added to the vial. By mass percent, the soybean oil sorbitan monooleate mixture was 76%, Tween 80 was 21%, and the water component was 3%. When all of the components were added, they were gently stirred on a hot plate at 45° C. The emulsion was allowed to stir and stabilize for at least 12 hours. After this period, each sample was translucent due to the system stabilizing into an emulsion. The clarity of the emulsion suggested that it was a reverse microemulsion. Once the microemulsion was formed, ethyl cellulose was added to achieve a mass percent of 10%. This mixture was heated to 160° C. to melt the ethyl cellulose, and allowed to cool to room temperature in a syringe until a gel formed.

Drugs were incorporated into the gelled emulsion in two different ways. In the first approach, hydrophilic drugs were dissolved into the water phase, and the solution was used to prepare the emulsion phase. In the second approach, the drug was added to the formulation after the emulsification. The drug was added to the liquid w/o microemulsion and ethyl cellulose mixture and allowed to cool to room temperature. For all emulsion trials, control experiments were conducted without adding any drugs. The first and the second approaches were mainly designed for the hydrophilic and hydrophobic drugs, respectively. Experiments were however conducted using both hydrophobic and hydrophilic drugs with both types of formulations to explore the dynamics of transport in both types of gels. Several drugs were explored including dexamethasone, timolol maleate, dexamethasone phosphate, cyclosporin and dexamethasone acetate. Table 1 summarizes the studies including the type of formulation (oleogel or gelled w/o emulsion), drug and the method of incorporation (added to water phase or the formulation after emulsification).

4. Test Drug-Delivery Compositions.

Table 1 below summarizes exemplary drug delivery compositions that were assessed in the studies described herein below. The drug delivery compositions in Table 1 were prepared as described above.

TABLE 1

| Type of Formulation | ID* | Drug Used | Drug Loading (wt %) | Method of Incorporation |
|---|---|---|---|---|
| Soybean oil/ethyl cellulose Oleogel | A | Dexamethasone | 28% | Oil Phase |
| | B | Dexamethasone Acetate | 28% | Oil Phase |
| | C | Dexamethasone Phosphate | 28% | Oil Phase |
| | D | Cyclosporin A | 28% | Oil Phase |
| | E | Timolol Maleate | 15% | Oil Phase |
| | F | Triamcinolone | 28% | Oil Phase |
| | G | Dexamethasone | 28% | Oil mixed with Octanoic Acid |
| | H | Dexamethasone Acetate | 28% | Oil mixed with Octanoic Acid |
| Emulsion-based Oleogel | I | Timolol Maleate | 1% | Water Phase |
| | J | Timolol Maleate | 8% | Formulation After Emulsification |
| | K | Dexamethasone | 28% | Formulation After Emulsification |
| | L | Metformin Hydrochloride | 0.15% | Water Phase |
| Soybean oil/ethyl cellulose Oleogel | M | Vancomycin | 25% | Oil Phase |
| | N | Metformin Hydrochloride | 10% | Oil Phase |
| | O | Vancomycin and (Timolol Maleate) | 10% (10%) | Oil Phase |
| | P | Dexamethasone and (Timolol Maleate) | 28% (10%) | Oil Phase |

*ID is the formulation reference or identifier used in the various studies described herein.

5. Drug Release Studies.

A drug delivery composition was prepared as described herein, and then loaded into a 3 mL syringe fitted with 22 gauge needle. Drug delivery compositions of required mass were injected into a 10 or 20 mL vial filled with 1×PBS. Samples were taken from vials at the indicated times and then analyzed using a ThermoSpectronic GENESYS UV spectrometer to determine the drug concentration. The spectra were obtained over a range of wavelengths to ensure that the measured spectra reflected the spectra of the drug being measured. In each experiment, three sets of measurements were carried out.

6. Solubility Determinations.

A significant parameter for the behavior of the disclosed drug delivery compositions is drug solubility in an aqueous environment and in hydrophobic environment, such as the soybean oil used in the examples described herein. Without wishing to be bound by a particular theory, it is possible that diffusion of the drug in the external medium (PBS) is a rate limiting step. Accordingly, solubility of the drug in this phase is crucial for modeling calculations of drug release. Solubility in the oil phase was estimated by preparing drug delivery compositions with different concentrations of drug, and observing the samples under a microscope. The presence of visible drug particles in the drug delivery composition indicated that the concentration was above solubility limit. Table 2 below shows the drugs used in experiments and their respective solubilities in water and soybean oil.

TABLE 2

| Name of Drug | Solubility Limit in PBS (25° C.) | Solubility Limit in Oil Phase of Drug Delivery Composition† |
|---|---|---|
| Dexamethasone | 89 µg/mL | 1%-3% |
| Dexamethasone Acetate | 16.4 µg/mL | ~1% |
| Dexamethasone Phosphate | * | <0.1% |
| Timolol Maleate | * | 0.1%-1% |
| Cyclosporin A | 29 µg/mL | ~30% |
| Triamcinolone | 80 mg/L | <0.1% |
| Metformin Hydrochloride | * | n.d. |
| Vancomycin Hydrochloride | * | n.d. |

* Indicates that the solubility of the indicated drug was so high that it was assumed to be infinite for the purposes of the studies described herein.
†% is apparent weight percent (wt %) as defined herein in the definitions section.

7. Imaging Analysis of Representative Drug Delivery Compositions.

The exemplary drug delivery compositions described above, see Table 1, were prepared and then ejected via a needle into phosphate-buffered saline using the methods described above. The images in FIGS. 1A-11C were obtained immediately after ejection into phosphate-buffered saline and various times thereafter as indicated herein.

FIGS. 1A-1C show a representative disclosed drug delivery composition comprising the test formulation described in Table 1, test formulation A. FIG. 1A shows the drug delivery composition shortly after expunging into phosphate-buffered saline. FIGS. 1B and 1C show the same drug delivery composition at 79 days and 124 days, respectively, following initial expunging into phosphate-buffered saline.

Figures 2A, 2B, 2C:
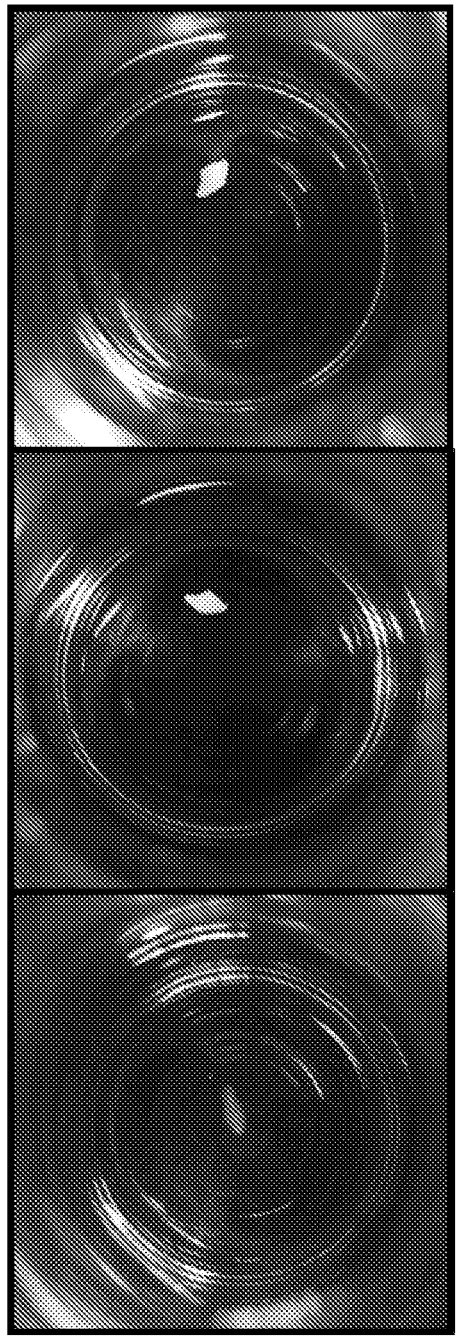
FIGS. 2A-2C show a representative disclosed drug delivery composition comprising the test formulation described in Table 1, test formulation B. The disclosed drug delivery composition in FIGS. 2A-2C was expunged through a 22 gauge needle into phosphate-buffered saline.

FIGS. 2A-2C show a representative disclosed drug delivery composition comprising the test formulation described in Table 1, test formulation B. FIG. 2A shows the drug delivery composition shortly after expunging into phosphate-buffered saline. FIGS. 2B and 2C show the same drug delivery composition at 51 days and 96 days, respectively, following initial expunging into phosphate-buffered saline.

FIGS. 3A-3C show a representative disclosed drug delivery composition comprising the test formulation described in Table 1, test formulation C. FIG. 3A shows the drug delivery composition shortly after expunging into phosphate-buffered saline. FIGS. 3B and 3C show the same drug delivery composition at 52 days and 97 days, respectively, following initial expunging into phosphate-buffered saline.

FIGS. 4A-4C show a representative disclosed drug delivery composition comprising the test formulation described in Table 1, test formulation D. FIG. 4A shows the drug delivery composition shortly after expunging into phosphate-buffered saline. FIGS. 4B and 4C show the same drug delivery composition at 34 days and 79 days, respectively, following initial expunging into phosphate-buffered saline.

FIGS. 5A-5C show a representative disclosed drug delivery composition comprising the test formulation described in Table 1, test formulation E. FIG. 5A shows the drug delivery composition shortly after expunging into phosphate-buffered saline. FIGS. 5B and 5C show the same drug delivery composition at 67 days and 112 days, respectively, following initial expunging into phosphate-buffered saline.

FIGS. 6A-6B show a representative disclosed drug delivery composition comprising the test formulation described in Table 1, test formulation F. FIG. 6A shows the drug delivery composition shortly after expunging into phosphate-buffered saline. FIG. 6B shows the same drug delivery composition at 18 days following initial expunging into phosphate-buffered saline.

FIGS. 7A-7C show a representative disclosed drug delivery composition comprising the test formulation described in Table 1, test formulation G. FIG. 7A shows the drug delivery composition shortly after expunging into phosphate-buffered saline. FIGS. 7B and 7C show the same drug delivery composition at 23 days and 68 days, respectively, following initial expunging into phosphate-buffered saline.

FIGS. 8A-8C show a representative disclosed drug delivery composition comprising the test formulation described in Table 1, test formulation H. FIG. 8A shows the drug delivery composition shortly after expunging into phosphate-buffered saline. FIGS. 8B and 8C show the same drug delivery composition at 17 days and 62 days, respectively, following initial expunging into phosphate-buffered saline.

FIGS. 9A-9C show a representative disclosed drug delivery composition comprising the test formulation described in Table 1, test formulation I. FIG. 9A shows the drug delivery composition shortly after expunging into phosphate-buffered saline. FIGS. 9B and 9C show the same drug delivery composition at 99 days and 144 days, respectively, following initial expunging into phosphate-buffered saline.

FIGS. 10A-10C show a representative disclosed drug delivery composition comprising the test formulation described in Table 1, test formulation J. FIG. 10A shows the drug delivery composition shortly after expunging into phosphate-buffered saline. FIGS. 10B and 10C show the same drug delivery composition at 45 days and 90 days, respectively, following initial expunging into phosphate-buffered saline.

Figures 11A, 11B, 11C:
FIGS. 11A-11C show a representative disclosed drug delivery composition comprising the test formulation described in Table 1, test formulation K. The disclosed drug delivery composition in FIGS. 11A-11C was expunged through a 22 gauge needle into phosphate-buffered saline.
Figures 12A, 12B, 12C:
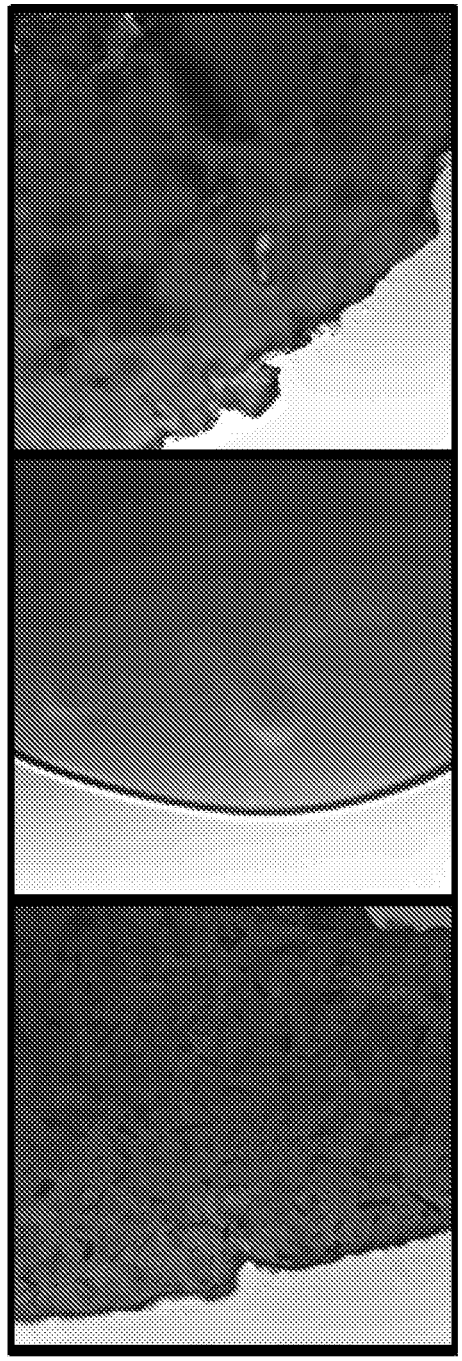

FIGS. 11A-11C show a representative disclosed drug delivery composition comprising the test formulation described in Table 1, test formulation K. FIG. 11A shows the drug delivery composition shortly after expunging into phosphate-buffered saline. FIGS. 11B and 11C show the same drug delivery composition at 37 days and 82 days, respectively, following initial expunging into phosphate-buffered saline.

The drug delivery composition comprising timolol in the water phase of the emulsion was ejected through a 14 gauge needle (see FIGS. 9A-9C), whereas all other compositions were ejected through a 22 gauge needle (see FIGS. 1A-8C and 10A-11C). The data show that the drug delivery compositions maintain an essentially cylindrical geometry when initially ejected, due, in part, to the high viscosity of the drug delivery composition. In some instances, the geometry of the ejected drug delivery composition in phosphate-buffered saline gradually changes to an approximately spherical geometry. In general, the gradual change to an approximately spherical geometry appears to for drug delivery compositions wherein the drug readily dissolves in the oil phase. Without wishing to be bound by a particular theory, it is possible that in these cases the drug acts as an inhibitor to gelation, and therefore the structural integrity of the gel is gradually lost over time. As well as becoming spherical, timolol maleate added to the oil after the formulation of an emulsion and cyclosporin A completely began to decompose and break apart into the release medium, phosphate-buffered saline.

Further images of the drug delivery compositions described above (and shown in FIGS. 1A-11C) were obtained at 2× magnification (see FIGS. 12A-12K). FIGS. 12A-K show images from disclosed drug delivery composition comprising the test formulation described in Table 1, test formulations A-K, respectively. These photomicrographic images show the interface between a glass microscope slide (left side of the images shown in FIGS. 12A-12K) and the drug delivery composition (right side of the images shown in FIGS. 12A-12K) for reference.

Briefly, the images show, in part, the effect of drug solubility on gelation of the drug delivery composition comprising the drug. For example, a drug delivery composition with soybean oil—ethyl cellulose drug comprises a drug, such as dexamethasone, at loading level that is significantly higher than the solubility limit of the drug (see FIG. 12A; Table 2), particulate material, likely comprising the drug, is apparent. In contrast, dexamethasone acetate has a much higher solubility (see Table 2), and the drug delivery composition comprising this drug appears to be relatively clear (see FIG. 12B). The dexamethasone acetate is a white powder that turns yellow in color when heated during the process of gelling giving a slight color to the gel. It was noted that the dexamethasone acetate-loaded drug delivery composition appeared to be the least viscous formulation tested based on the ease of pushing out the device. This is also apparent in the observed thin layer at the edge of the drug delivery composition where the gel appears to be changing phase to form the oil phase (see FIG. 12B). Without wishing to be bound by a particular theory, it is possible that the drug acts an inhibitor of the gelation. Such a theory is consistent with the the shape of the ejected drug delivery composition which slowly changes shape from a cylindrical geometry to a spherical geometry. The potential inhibitory effect of the drug on gelation may be caused by the high solubility of the drug in the drug delivery composition. Without wishing to be bound by a particular theory, when a high level drug dissolves into the oil, it effectively reduces the weight fraction of the gelator.

Dexamethasone sodium phosphate (FIG. 12C) also dissolves in the oil phase to form a solution resulting in a clear appearance in the microscopic image. Dark material seen in the image may be the result of drug particles that degraded during the heating step preparing the drug delivery composition loaded with drug. Additionally, the microscopic images contain a few bubbles that were trapped while placing a cover-slip on the gel placed on the slide. Without wishing to be bound by a particular theory, this observation is consistent with the drug reducing the interfacial tension of the oil interface. This apparent effect also results in a rough boundary of the gel as seen in the image.

Cyclosporin A (FIG. 12D) dissolved into the soybean oil resulted in a clear single-phase oleogel drug delivery composition.

The oleogel drug delivery composition comprising timolol maleate shows visible particles under microscope, (FIG. 12E), which may be due to the low solubility of the drug.

Triamcinolone (FIG. 12F) was loaded in the oleogel drug delivery composition at a concentration significantly higher than the solubility limit, the result of which are likely the visible particles in the microscopic image. The particles shown in the image appear to be different sizes due to the agglomeration of particles during gel formation, and also possibly due to the non-uniformity in size of the drug particles in the material used to prepare the composition.

The image of a device in which timolol was added to the water phase of a W/O emulsion (FIG. 12I) does not show discernable features. Without wishing to be bound by a particular theory, it is possible that the emulsion formed before gelling had become a microemulsion. Accordingly, it is possible that the water drops are far too small to be visible in the microscope. These drug delivery compositions are translucent with a slight yellow coloring due to soybean oil and surfactants used.

Timolol maleate and dexamethasone emulsion formulations in which drug particles were added during the gel formation step are also shown (see FIGS. 12J and 12K, respectively). Both emulsion formulations required more force to push the device through the needle tip. The timolol maleate gel was gold in color, and contained a high concentration of undissolved particles of timolol maleate. The dexamethasone loaded gelled reverse emulsion was white, contained particles and had a creamy texture (FIG. 12K). As with dexamethasone sodium phosphate, observing the dexamethasone emulsion formulation under microscope was hindered by bubble formation when placing a microscope slide. Without wishing to be bound by a particular theory, this observation is consistent with the combination of drug and surfactant reducing the interfacial tension of the oil interface. This effect may also underlay the observed rough boundary of the gel seen in the image.

The relative size of the exemplary drug delivery compositions ejected from a needle is shown in FIG. 13, which shows a representative oleogel drug delivery composition comprising dexamethasone which has been ejected onto a human thumb. The overall size of the drug delivery composition is determined, at least in part, by the needle gauge and the desired mass of the ejected drug delivery composition. The oleogel drug delivery compositions tend to be yellowish-white in color due to the yellow color of soybean oil (as a resulting of the heating step). In these oleogel drug delivery compositions, there are visible white particles, mostly likely particulate, undissolved dexamethasone. The physical structure of oleogel drug delivery composition comprising dexamethasone is grainy and particles are easily visible within the oleogel.

Figure 14A:
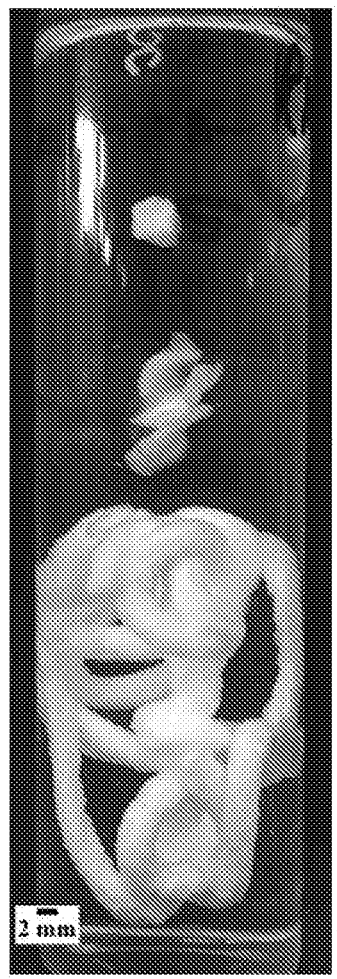
FIG. 14A-14B show representative images of representative disclosed drug delivery compositions that have been expunged through a hypodermic needle.
Figure 14B:
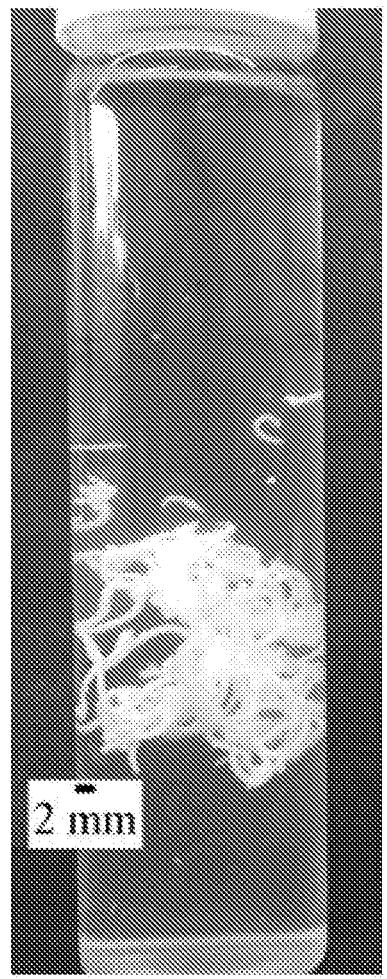

The present exemplary and disclosed oleogel drug delivery compositions have additional interesting properties that may make them useful generally as drug delivery formulations for non-retinal or ocular drug delivery. The stability of the disclosed drug delivery compositions is shown, in part, in FIGS. 14A and 14B. These figures show a large volume of oleogel drug delivery composition (without a drug material) ejected into deionized water using a 14 gauge needle (FIG. 14A) or a 25 gauge needle (FIG. 14B). The images were obtained after the gels had been in the deionized water for several months. It is important to note that as relatively large volumes (relative to the volume that would be used for an retinal or ocular injection) of a oleogel drug delivery composition are ejected through a needle, that the oleogel drug delivery composition forms a network structure that twists and turns back upon itself. In contrast, when the volumes ejected are typical of those that would be used in a retinal or ocular injection, the ejected oleogel drug delivery composition has an essentially cylindrical geometry.

8. Drug Release Profiles

The rate of drug release from the exemplary oleogels drug delivery compositions ejected into a release medium, phosphate-buffered saline (PBS), was measured by removing samples periodically and determining the drug concentration using UV-Vis spectroscopy. The volume of the surrounding PBSid (3-15 mL) was significantly larger than the volume of the oleogel drug delivery composition (0.0009-0.0038 mL). Accordingly, release medium can be considered to be a sink even for the hydrophobic drugs. The dynamic concentrations were used to calculate the fraction of the drug that was released. These data are shown in FIGS. 15-26, and further described herein below. The error bars shown in the figures are the standard deviation of three independent experiments.

a. Release of Timolol Maleate from Gelled Water-in-Oil Emulsion

Figure 15:
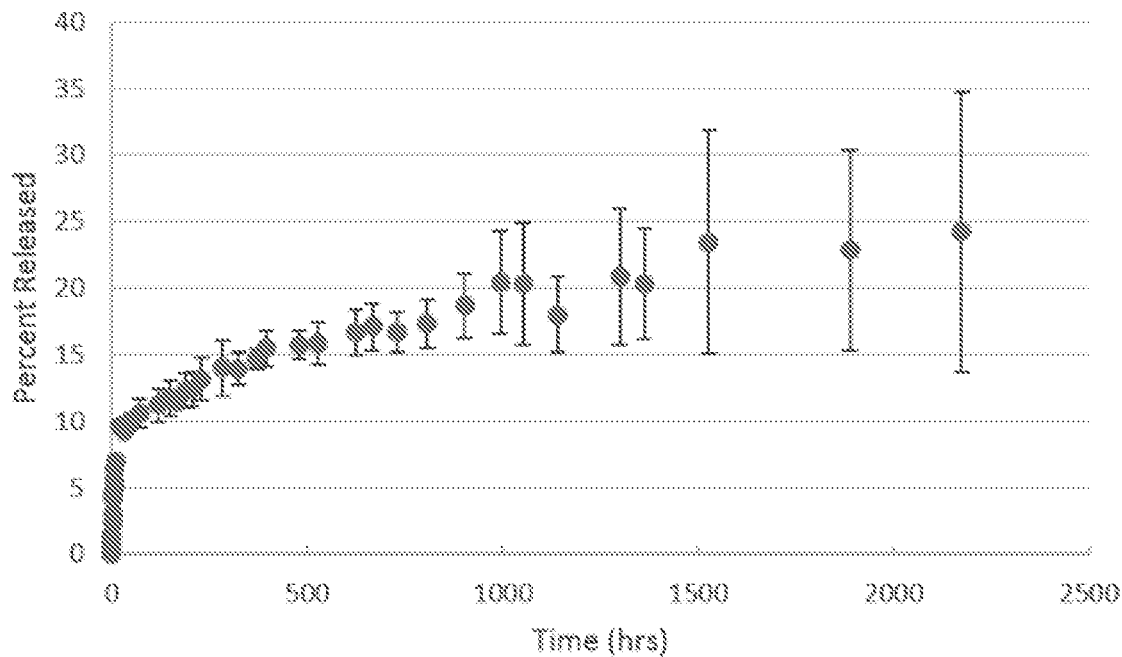
FIG. 15 shows a representative drug release profile for a representative disclosed drug delivery composition comprising 1 wt % timolol maleate over a period of about 2170 hours. The data show that there is a rapid drug release in the initial 10 hours, followed by a slow gradual drug release over a period of several weeks.
Figure 16:
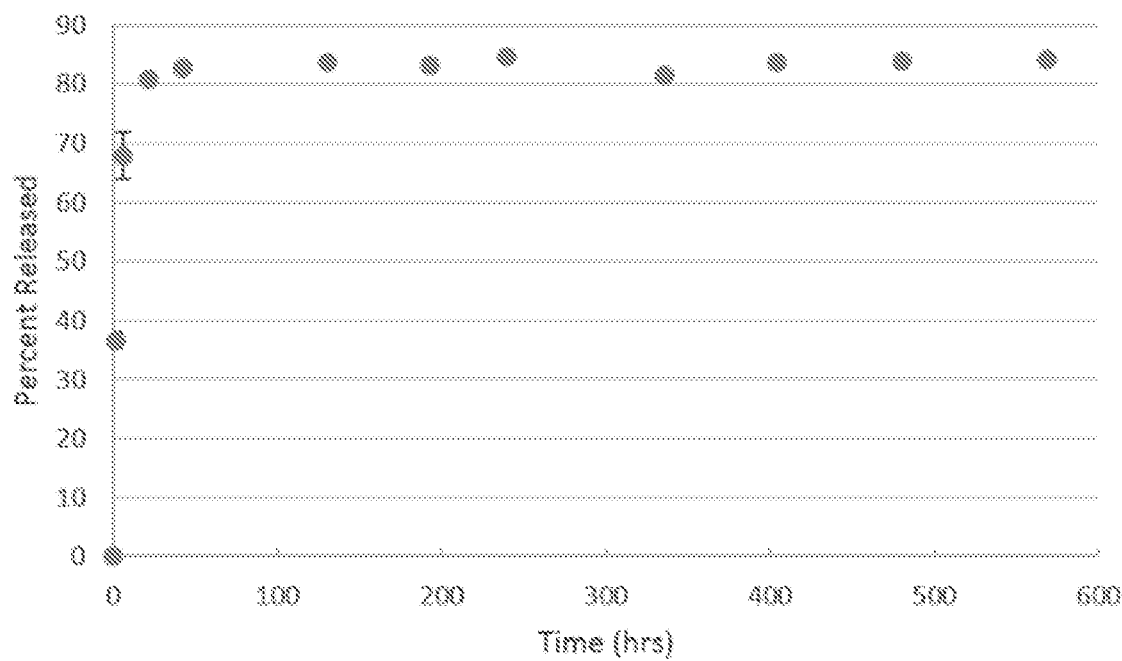
FIG. 16 shows a representative drug release profile for a representative disclosed drug delivery composition comprising 28 wt % dexamethasone sodium phosphate over a period of about 570 hours. The data show that there is a rapid drug release in the initial 20 hours resulting in the release of about 80% of the drug load, followed by a slow gradual drug release over a period of several weeks resulting in the release of additional drug such that a total of 85% of the initial drug load was released.
Figure 17:
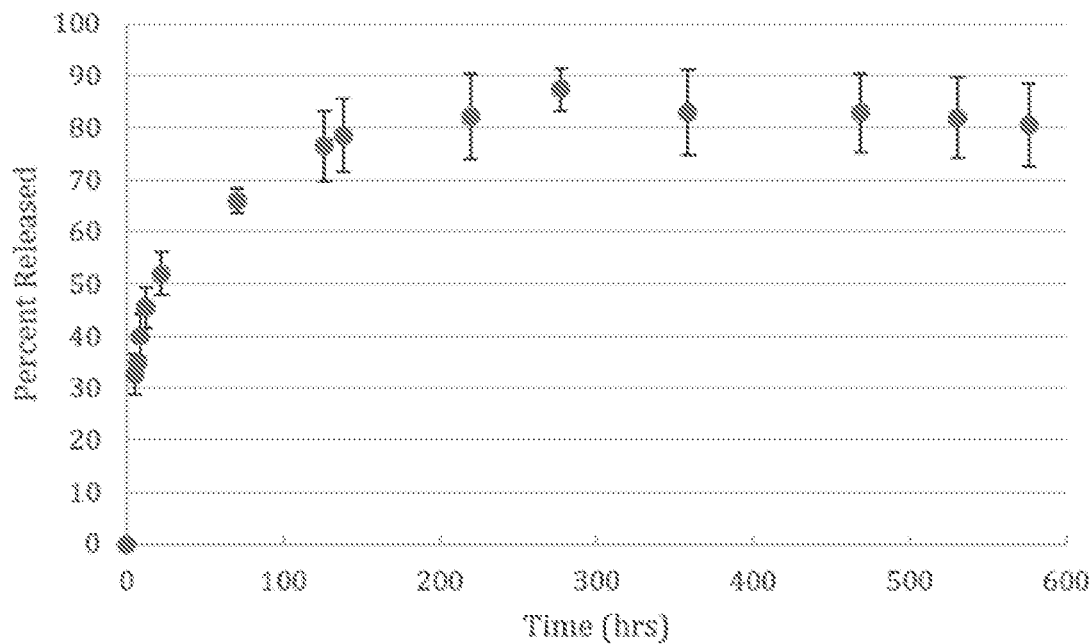
FIG. 17 shows a representative drug release profile for a representative disclosed drug delivery composition comprising 15 wt % dexamethasone sodium phosphate over a period of about 570 hours. The data show an initial rapid release of drug in the initial 30 hours resulting in about 50% release of the initial drug load, followed by attenuated gradual release of drug over the next 100 hours resulting in a cumulative release of about 80% of the initial drug load.
Figure 18:
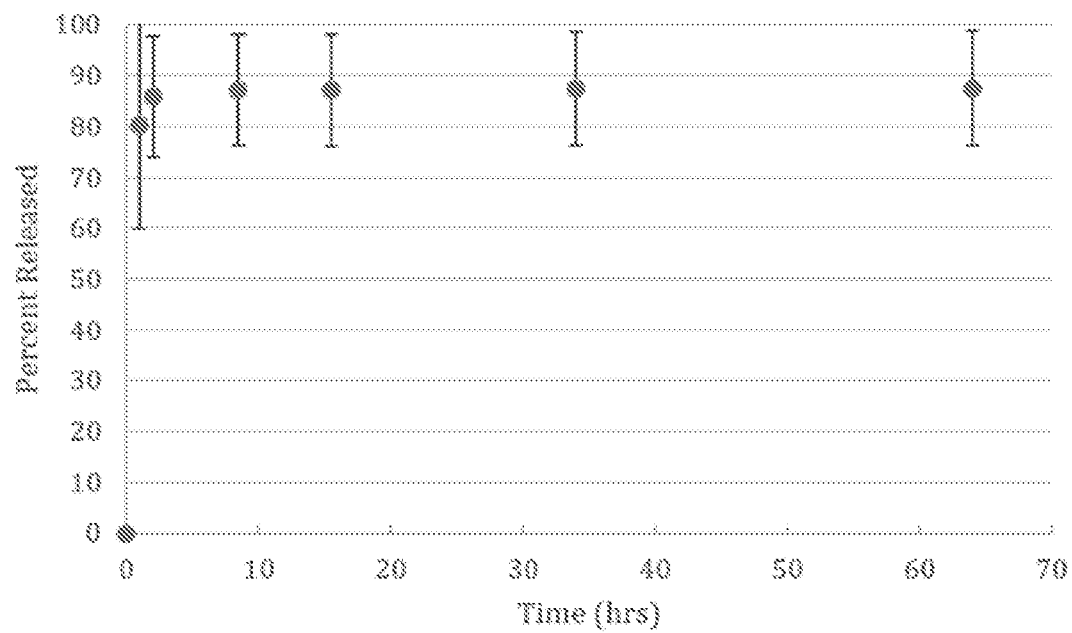
FIG. 18 shows a representative drug release profile for a representative disclosed drug delivery composition comprising 8 wt % dexamethasone sodium phosphate over a period of about 65 hours. The data show a very rapid release of drug in the initial 1-2 hours resulting in about 85% release of the initial drug load.
Figure 19:
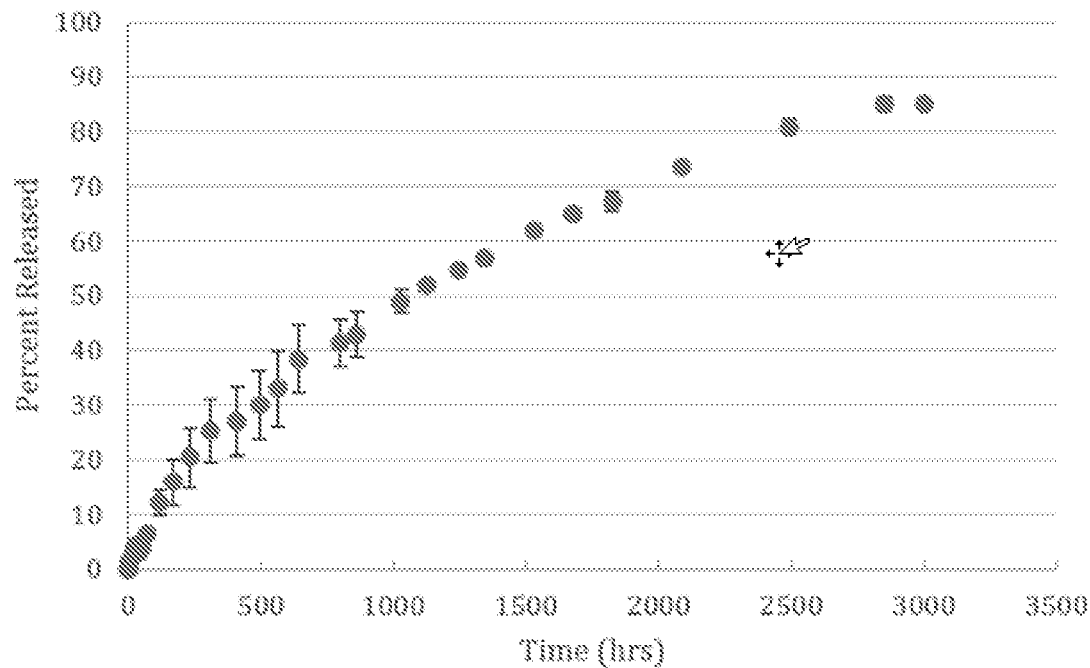
FIG. 19 shows a representative drug release profile for a representative disclosed drug delivery composition comprising 28 wt % dexamethasone over a period of about 3,000 hours. The data show a release duration of several months, with a cumulative release of about 85% of the initial drug load achieved at about 3,000 hours.
Figure 20:
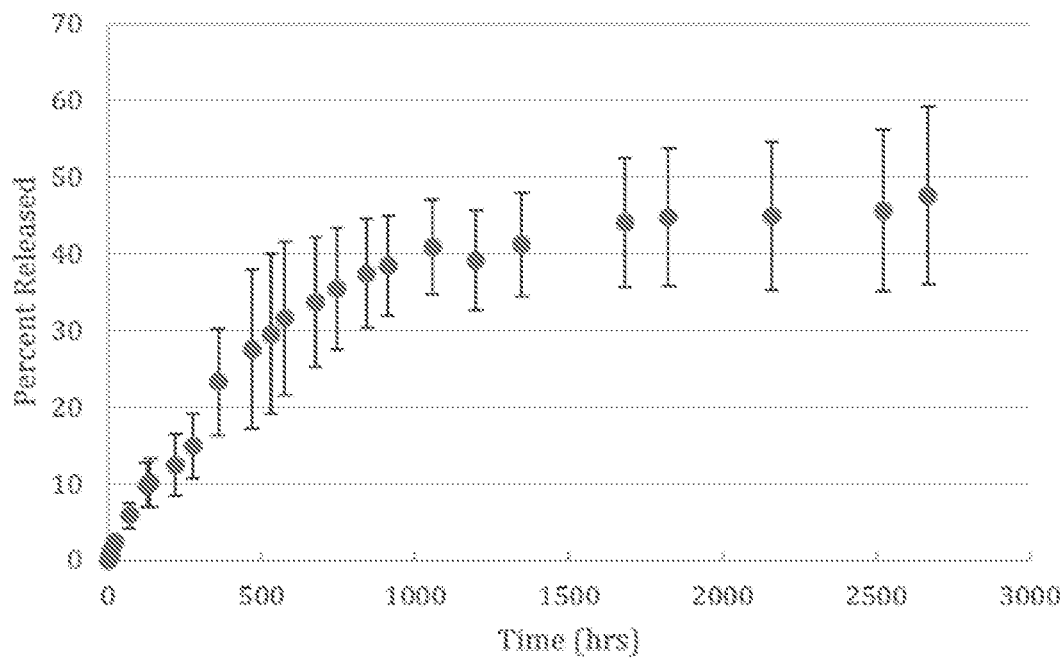
FIG. 20 shows a representative drug release profile for a representative disclosed drug delivery composition comprising 40 wt % dexamethasone over a period of about 3,000 hours. The data show a release duration of several months, with a cumulative release of about 48% of the initial drug load achieved at about 2,660 hours.
Figure 21:
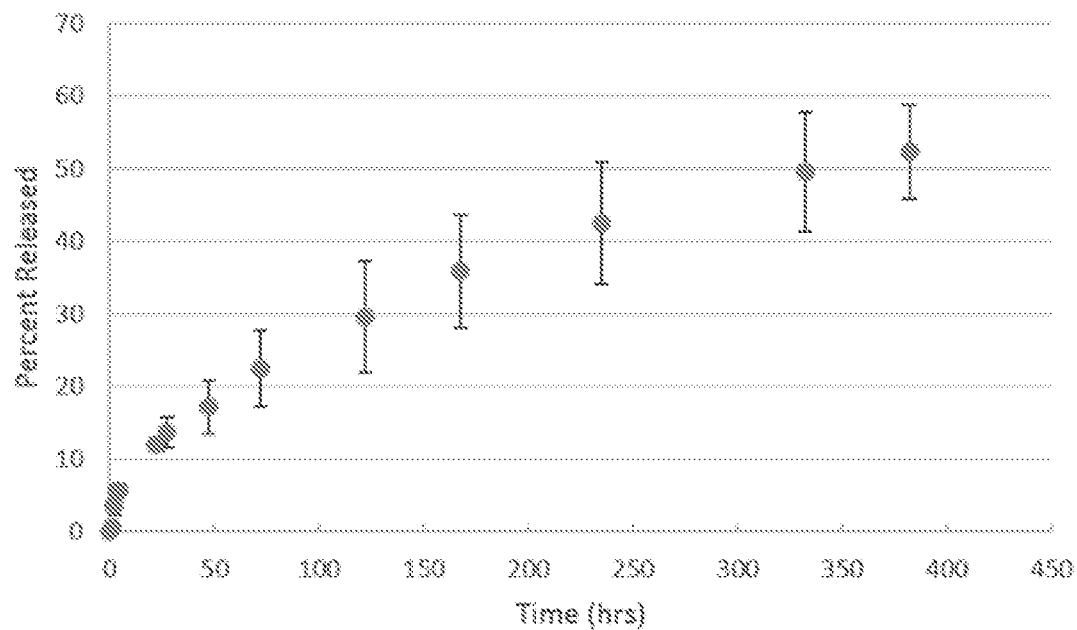
FIG. 21 shows a representative drug release profile for a representative disclosed drug delivery composition comprising 28 wt % dexamethasone over a period of about 3,000 hours. The data show a release duration of about 400 hours, with a cumulative release of about 50% of the initial drug load achieved at about 400 hours.
Figure 22:
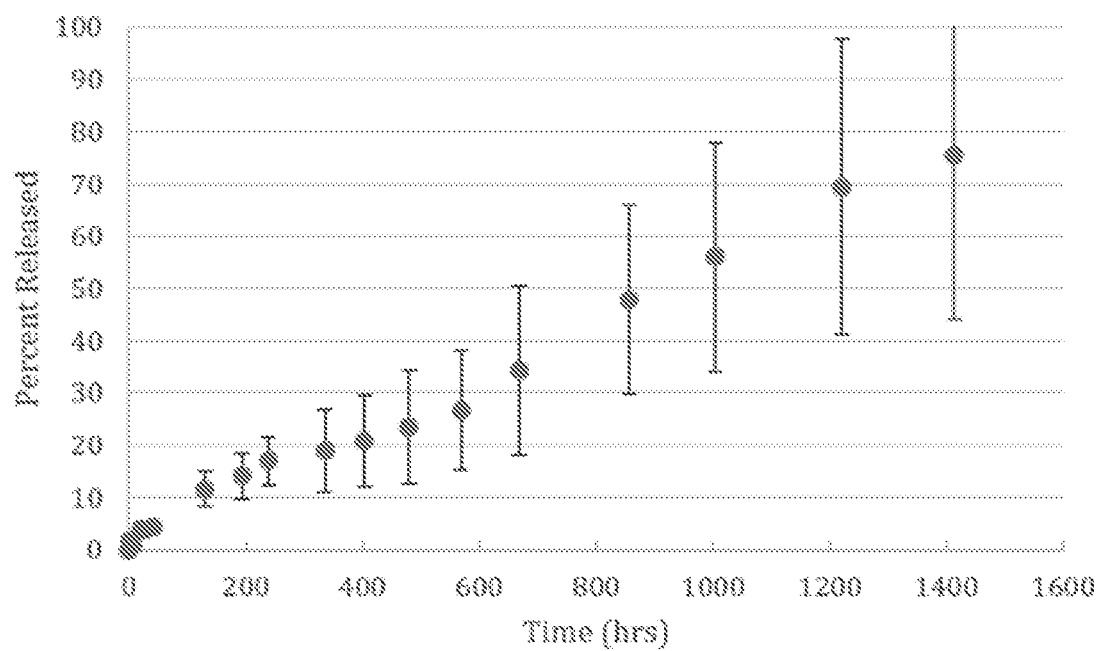
FIG. 22 shows a representative drug release profile for a representative disclosed drug delivery composition comprising 28 wt % dexamethasone acetate over a period of about 1,440 hours. The data show an extended release that is approximately linear over a period of 1,440 hours, with a cumulative release of about 76% achieved at about 1,440 hours.
Figure 23:
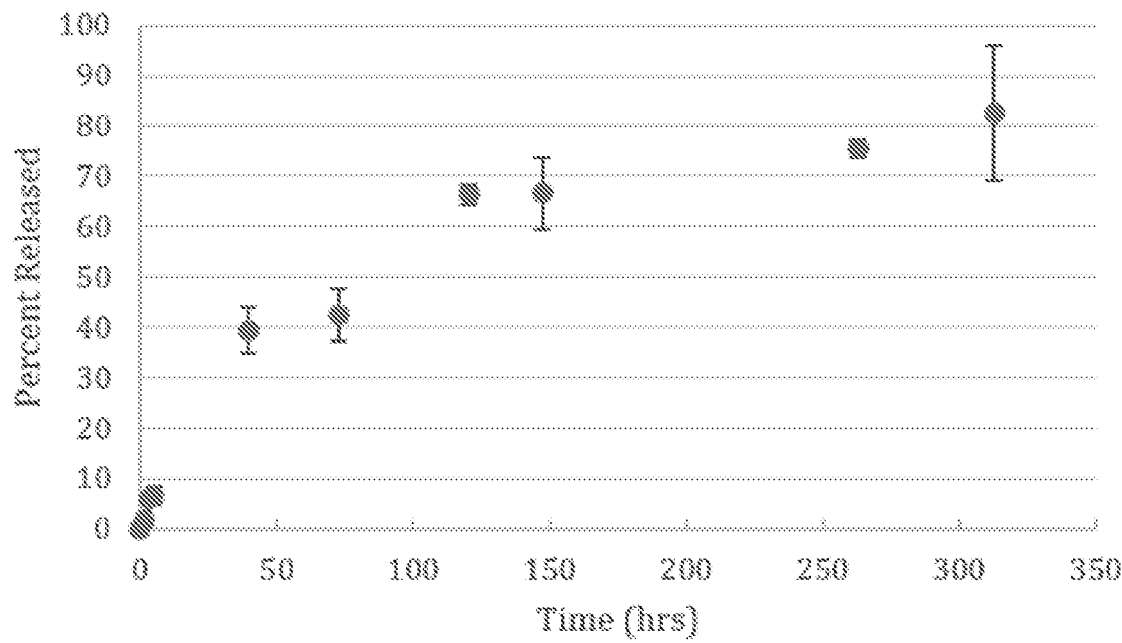
FIG. 23 shows a representative drug release profile for a representative disclosed drug delivery composition comprising 28 wt % cyclosporin A over a period of about 325 hours. The data show a cumulative release of about 82% of the initial drug load achieved at about 325 hours.
Figure 24:
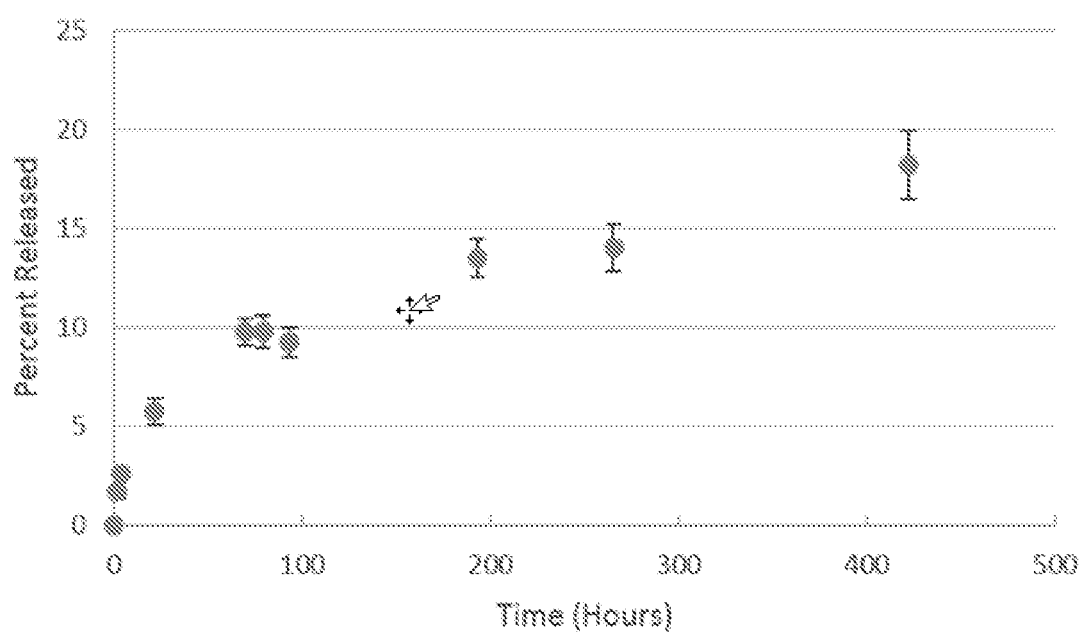
FIG. 24 shows a representative drug release profile for a representative disclosed drug delivery composition comprising 28 wt % triamcinolone over a period of about 430 hours. The data show a cumulative release of about 18% of the initial drug load achieved at about 430 hours.
Figure 25:
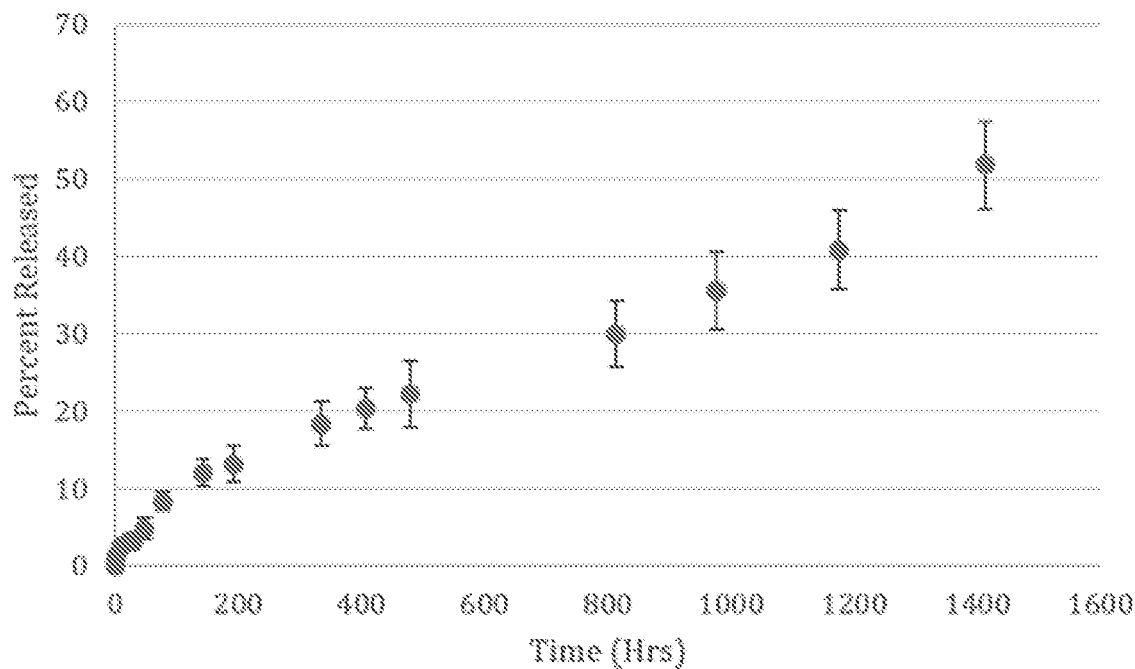
FIG. 25 shows a representative drug release profile for a representative disclosed drug delivery composition comprising 28 wt % dexamethasone over a period of about 1,400 hours. The data show an extended release of drug over the time period examined, with a cumulative release of about 51% of the initial drug load achieved at about 1,410 hours.
Figure 26:
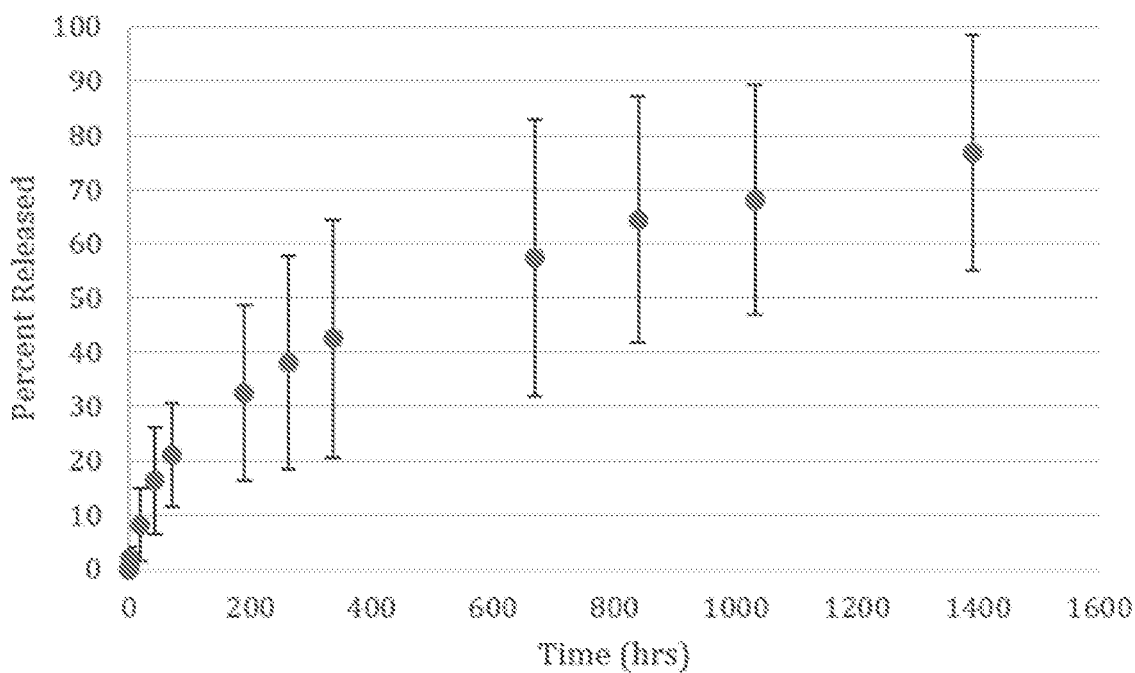
FIG. 26 shows a representative drug release profile for a representative disclosed drug delivery composition comprising 28 wt % dexamethasone acetate over a period of about 1,400 hours. The data show an extended biphase release of drug over the time period examined, with a cumulative release of about 78% of the initial drug load achieved at about 1,390 hours.

Timolol maleate was added to the water phase of a water in oil (W/O) microemulsion, and then the emulsion was gelled (Formulation I, Table 1). The timolol maleate concentration in the aqueous phase was 33% and the microemulsion contained 3% aqueous phase, resulting in an overall drug loading of 0.95% by mass and a total drug loading of 300 μg in the ejected drug delivery composition (which was ejected using a 14 gauge needle). FIG. 15 shows that about 10% of the loaded drug was released in an initial burst lasting about 10 hours, followed by slow release with a cumulative release of about 24% of the loaded drug was released after 2170 hours. Since timolol maleate is hydrophilic, 100% release of the loaded drug was predicted. Accordingly, based upon the drug release profile shown in FIG. 15, it is anticipated that this drug delivery composition should release drug for about 9-18 months. The extended release of the drug is likely due to the low solubility of the drug in the oil phase, and larger radius of the device. Moreover, a very large fraction of the drug is ionized at the pH of the aqueous phase. The ionized drug does not partition into the oil phase and so the concentration of the drug in the oil phase that is in equilibrium with the PBS is very low. The drug containing water drops therefore act as drug depots releasing the drug slowly to the oil as the drug diffuses from the oil into the surrounding aqueous phase. The transport therefore can be described by the Higuchi model that was initially derived for transport from ointments containing drug particles (Higuchi, T. *Journal of Pharmaceutical Sciences*. (1961) 50:874-875; Xu, Xiaoming, et al. *International Journal of Pharmaceutics*. (2015) 494:31-39; Siepmann, J. and Peppas, N. *International Journal of Pharmaceutics*. (2011) 418:6-12). Similar models have been used to describe drug transport from hydrogels containing drug particles or surfactant aggregates that have a high affinity for the drug (Gupta, C. and Chauhan, A. *Journal of Colloid and Interface Science*. (2010) 347:31-42).

b. Release of Dexamethasone Sodium Phosphate from an Oleogel Drug Delivery Composition with Drug Added Directly to the Oil Phase The release profile of dexamethasone sodium phosphate directly added to the oil phase during preparation is shown in FIG. 16 (corresponding to Formulation C, Table 1). The drug loading in this formulation was 28%, and the volumes of the oleogel drug release composition ejected into release medium was 0.0024 mL (the volume of the release medium was 10 mL). The drug powder was added to the gel as it was cooling to minimize the drug exposure to the high temperature. The release profile in FIG. 16 shows that almost the entire drug payload was released in a short duration of about 20 hours. The short release duration of dexamethasone phosphate can be attributed to the high solubility of the non-ionized drug in the oil phase, as evident from the microscopic images, which do not show any particles. The drug is considered hydrophobic, but when dissolved in water, resulting in high aqueous solubility. In the oil phase though, the drug is not ionized and is highly soluble therein. Without wishing to be bound by a particular theory, the drug dissolves in the oil phase of the oleogel drug delivery composition, and diffuses through the gelled oil phase in the non-ionized form, and upon diffusion into the aqueous phase, it ionizes and dissolves therein. Further, without wishing to be bound by a particular theory, the rate of the drug release is likely controlled by diffusion through the oil phase, but the total release duration is not long. The drug transport can be described by the unsteady diffusion equation and the release time scales as the square of the radius divided by the drug diffusivity in the gel.

c. Release of Timolol from an Oleogel Drug Delivery Composition with Drug Added Directly to the Oil Phase Incorporation of timolol maleate in the aqueous phase of the microemulsions resulted in the long release duration but the overall drug loading in the device was only 0.95%. By contrast, the drug loading that can be achieved by direct addition of the drug into the oil phase could be as high as 20-30%. So, devices were prepared by adding timolol maleate powder to the oil phase (corresponding to Formulation E, Table 1). FIG. 17 shows release data for a study in which timolol maleate was added directly to oil as it was cooling in order to prepare an oleogel drug delivery composition comprising 15 wt % timolol. The volume of the ejected oleogel drug delivery composition comprising timolol was 0.0031 mL, and this volume was ejected into release medium with a volume of 6 mL. The drug release was slower compared to dexamethasone phosphate but much faster compared to the timolol release when it was loaded into the microemulsion. The slower release compared to dexamethasone phosphate is likely due to a lower solubility of timolol maleate in the oil, as evident from the presence of particles in the microscopic images. The much faster release compared to the microemulsions suggests that the solubility limit of timolol maleate in the oil is much higher than the concentration of the non-ionized drug in the oil phase when the drug was dissolved in the aqueous phase of the microemulsions. The transport therefore can be described by the Higuchi model initially derived for transport from ointments containing drug particles (Higuchi, T. *Journal of Pharmaceutical Sciences*. (1961) 50:874-875; Xu, Xiaoming, et al. *International Journal of Pharmaceutics*. (2015) 494:31-39; Siepmann, J. and Peppas, N. *International Journal of Pharmaceutics*. (2011) 418:6-12).

d. Release of Timolol from an Oleogel Drug Delivery Composition in which Drug was Added to the Oil Phase of a Water-in-Oil Emulsion Timolol was added to a gelled microemulsion as a possible approach to modulate the release of timolol while retaining the high drug loading. In this study, timolol maleate was added to the oil phase of a W/O microemulsion to create an 8 wt % loading formulation (corresponding to Formulation J, Table 1). The volume of the ejected oleogel drug delivery composition comprising timolol was 0.0038 mL, and this volume was ejected into release medium with a volume of 5 mL. The release profile in FIG. 18 shows that this approach led to a very rapid drug release, even faster compared to when the drug was added to just the oleogel without the aqueous microemulsion phase. Without wishing to be bound by a particular theory, the fast release may be due to an increase in the solubility of the drug in the oil due to the surfactant that was included in this formulation. Based on the imaging, timolol maleate did not completely dissolve, but a higher fraction dissolved compared to the case when the drug was directly added to the oil. The release duration is comparable to that for dexamethasone phosphate, which dissolved completely in the oil, suggesting the diffusivity of timolol may be higher than that for dexamethasone acetate.

e. Release of Dexamethasone from an Oleogel Drug Delivery Composition Comprising Solid Drug Particles A dexamethasone oleogel was prepared by first melting a soybean oil and ethyl cellulose oleogel, then adding the drug to achieve a 28 wt % by mass composition (this formulation corresponds to Formulation A, Table 1). The majority of the drug remained undissolved resulting in oleogel drug delivery composition that comprised dispersed drug particles. This device was loaded with 700 µg of drug. The volume of the ejected oleogel drug delivery composition comprising dexamethasone was 0.0023 mL, and this volume was ejected into release medium with a volume of 10 mL. The same method was used to achieve an oleogel of 40 wt % by mass dexamethasone. For this oleogel drug delivery composition, the volume of the ejected oleogel drug delivery composition comprising dexamethasone was 0.0009 mL, and this volume was ejected into release medium with a volume of 6 mL. The release profiles from devices with 28% and 40% loadings are shown in FIGS. 19 and 20, respectively. The release durations for both loadings are at least a few months. Specifically, the 28 wt % dexamethasone oleogel drug delivery composition released 85% of the initial drug load after about 3000 hours, and the 40 wt % dexamethasone oleogel drug delivery composition released 47.6% of the initial drug load after 2660 hours. The long release duration suggests a low solubility of dexamethasone in the oil phase, which is supported by the microscopic images showing a high fraction of particles. The drug particles act as depots that dissolve as the drug concentration decreases below the solubility limit due to diffusion into the surrounding medium. The release can thus be described by Higuchi model for drug particles dispersed in an ointment, which suggests that the release duration should depend on the ratio of the drug loading and the solubility limit. The release duration from the gel loaded initially with 40 wt % dexamethasone oleogel drug delivery composition should be longer by about 30% compared to the gel loaded with 28 wt % dexamethasone oleogel drug delivery composition.

f. Release of Dexamethasone from an Oleogel Drug Delivery Composition with Drug Added to the Oil Phase of a Water-in-Oil Emulsion FIG. 21 shows the release profile from a device that was formed after adding 28% dexamethasone to a reverse emulsion, followed by gelation (corresponding to Formulation K, Table 1). The volume of the ejected gelled emulsion drug delivery composition comprising dexamethasone was 0.0024 mL, and this volume was ejected into release medium with a volume of 10 mL. The results show an extended release, but at rates that are higher compared to those from the drug delivery compositions in which the drug was added to the oil phase without the microemulsion. Without wishing to be bound by a particular theory, the faster release of dexamethasone from the gelled microemulsion drug delivery composition compared the release of dexamethasone from the oleogel drug delivery composition without the aqueous phase can be due to an increase in solubility of the drug in the oil phase due to the surfactant.

g. Release of Dexamethasone Acetate from an Oleogel Comprising Solid Drug Particles The release profile of another dexamethasone derivative, dexamethasone acetate, was assessed to determine whether the release duration could be further increased by using a different form of dexamethasone. The oleogel drug delivery composition used in this study corresponds to Formulation B, Table 1. The volume of the ejected gelled emulsion drug delivery composition comprising dexamethasone was 0.0024 mL, and this volume was ejected into release medium with a volume of 10 mL. The hydrophobic dexamethasone acetate also exhibited an extended release lasting at least a few months. FIG. 22 shows that about 75.5% of the initial drug load was released in about 1400 hours, which is faster compared to unmodified dexamethasone. The extended release was unexpected, in part, due to the observation from photomicrographs that dexamethasone acetate appeared to be dissolved in the oil phase. Accordingly, without wishing to be bound by a particular theory, if the rate of transport was limited by the oleogel drug delivery composition, the higher solubility of the drug would be predicted result in a faster release duration, possibly comparable to that for dexamethasone phosphate. Without wishing to be bound by a particular theory, the extended release duration could be due to the drug release in this example being controlled by diffusion into the surrounding aqueous phase. This hypothesis is consistent with approximately linear release profile compared to the decreasing release rates with time for the other examples described herein.

h. Release of Cyclosporin a from an Oleogel Drug Delivery Composition with Drug Added Directly to the Oil Phase FIG. 23 shows the drug release profile from an oleogel drug delivery composition comprising cyclosporin A. The volume of the ejected gelled emulsion drug delivery composition comprising dexamethasone was 0.0014 mL, and this volume was ejected into release medium with a volume of 15 mL. After about 310 hours, 82% of the initial drug load drug was released. Without wishing to be bound by a particular theory, the release of cyclosporin A may be controlled by diffusion into the aqueous phase. That is, even though cyclosporin A is hydrophobic, its solubility is higher than that of dexamethasone acetate and this may explain the higher rate of release from the oil phase of the oleogel. Without wishing to be bound by a particular theory, the decrease in the rate of release after about 150 hours could be associated with the rate controlling step shifting from diffusion into the aqueous phase to diffusion in the gel because as the boundary layer in the gel thickens.

i. Release of Triamcinolone from an Oleogel Drug Delivery Composition Comprising Solid Drug Particles The formulation used in this study, corresponding to formulation F (Table 1) was prepared in the same manner as that described above for the preparation of formulation A (Table 1). Briefly, an oleogel drug delivery composition was prepared comprising 610 µg of triamcinolone (28 wt % drug loading based on the total weight of the drug, soybean oil and ethyl cellulose). The volume of the ejected gelled emulsion drug delivery composition comprising dexamethasone was 0.0022 mL, and this volume was ejected into release medium with a volume of 10 mL. The data in FIG. 24 shows that after 430 hours, the oleogel drug delivery composition comprising triamcinolone released about 18.1% of the initial drug load. Compared to the drug delivery composition comprising dexamethasone (28 wt %), the percent released was lower at a similar time point. The release pattern in FIG. 24 shows an initial burst, followed by a slower, steady release out to 430 hours following the initial burst.

j. Release of Dexamethasone from an Oleogel Drug Delivery Composition Comprising Drug Added Directly to an Oil and Octanoic Acid Mixture The formulation used in this study corresponds to formulation G (Table 1) with dexamethasone, and it was prepared in a similar manner to that described for the preparation of formulation A (Table 1). The oleogel drug delivery composition comprised 28 wt % dexamethasone (wt % based on the total mass of dexamethasone, soybean oil, and ethyl cellulose used in the composition). This study differed from the study described above for formulation A because the oleogel drug delivery composition was formed by first forming a mixture of soybean oil and octanoic acid, followed by addition of solid dexamethasone to the liquid phase of this gel. Prior to the addition of dexamethasone, octanoic acid comprised 20% of the gel by mass, with soybean oil and ethyl cellulose comprising 70 wt % and 10 wt %, respectively. From the photomicrograph images, it appeared that the majority of the drug remained undissolved resulting in oleogel drug delivery composition comprising drug particles dispersed therein. The prepared oleogel drug delivery composition assessed in this study had initial drug load of 700 µg. The volume of the ejected gelled emulsion drug delivery composition comprising dexamethasone was 0.0023 mL, and this volume was ejected into release medium with a volume of 10 mL. The release profile from the foregoing formulation is shown in FIG. 25. The data show that about 51% of the initial drug load after about 1410 hours. Similar to the data obtained with formulation A (Table 1) described herein above, an extended release profile was observed. Without wishing to be bound by a particular theory, the extended release duration could be due to low solubility of dexamethasone in the oil phase. The drug release kinetics could be described by Higuchi model, which suggests that the release duration could depend on the ratio of the drug loading and the solubility limit.

k. Release of Dexamethasone Acetate from an Oleogel Drug Delivery Composition with Drug Added Directly to an Oil and Octanoic Acid Mixture The formulation used in this study corresponds to formulation G (Table 1) with dexamethasone acetate, and it was prepared in a similar manner to that described for the preparation of formulation F (Table 1). The oleogel drug delivery composition comprised 28 wt % dexamethasone acetate (wt % based on the total mass of dexamethasone, soybean oil, and ethyl cellulose used in the composition). This study differed from the study described above for formulation A because the oleogel drug delivery composition was formed by first forming a mixture of soybean oil and octanoic acid, followed by addition of solid dexamethasone to the liquid phase of this gel. Prior to the addition of dexamethasone, octanoic acid comprised 20% of the gel by mass, with soybean oil and ethyl cellulose comprising 70 wt/0 and 10 wt %, respectively. The prepared oleogel drug delivery composition assessed in this study had initial drug load of 700 µg. The volume of the ejected gelled emulsion drug delivery composition comprising dexamethasone was 0.0023 mL, and this volume was ejected into release medium with a volume of 10 mL. The release profile from the foregoing formulation is shown in FIG. 26. The data show that about 23% of the initial drug load was released after about 330 hours. In contrast to dexamethasone acetate in formulation F, the release profile does not appear to be linear. Without wishing to be bound by a particular theory, the release kinetics are not rate limited by diffusion into the surrounding aqueous phase. However, this theory may be incorrect due to high error in drug release data. It should be noted, that the drug delivery composition described herein and immediately above were less structurally ridged compared to other examples described herein, and thereby potentially leading to greater sampling errors.

l. Release of Metformin Hydrochloride from Gelled Water-in-Oil Emulsion

Figure 36:
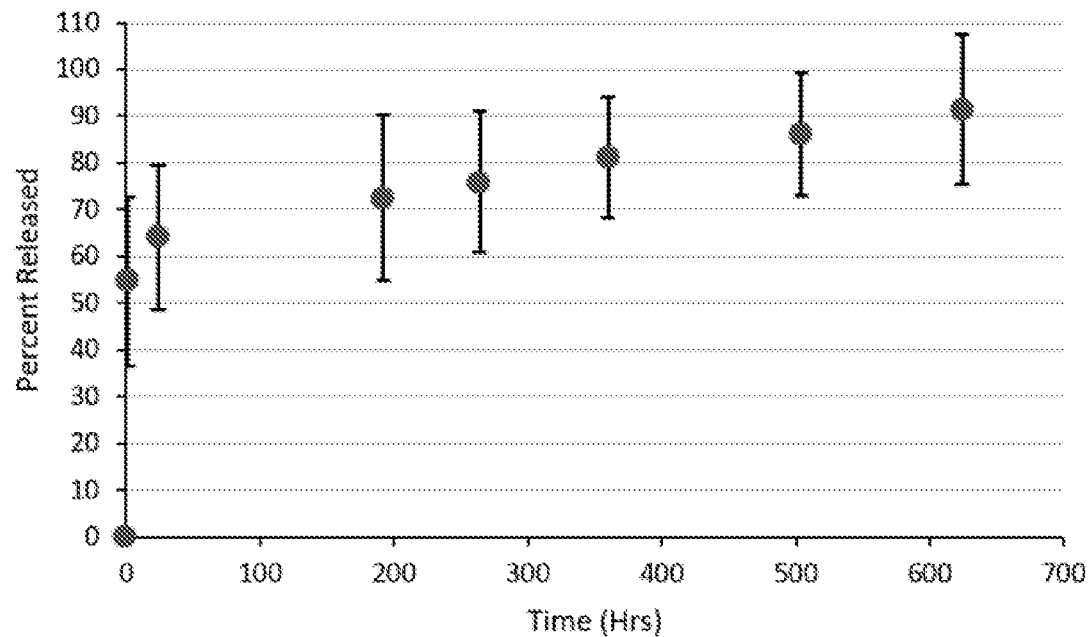
FIG. 36 shows a representative drug release profile for a representative disclosed drug delivery composition comprising 25 wt % vancomycin over a period of about 630 hours. The data show an extended release of drug over the time period examined, with a cumulative release of about 91% of the initial drug load achieved at about 630 hours.
Figure 37:
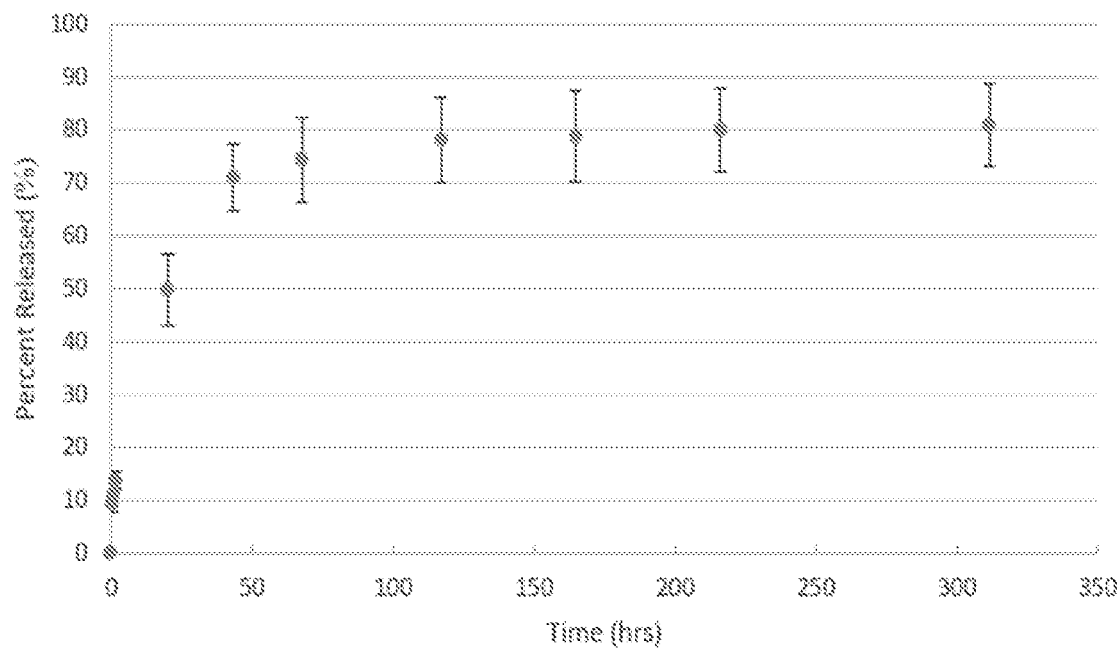
FIG. 37 shows a representative drug release profile for a representative disclosed drug delivery composition comprising 10 wt % metformin hydrochloride over a period of about 315 hours. The data show an extended release of drug over the time period examined, with a cumulative release of about 81% of the initial drug load achieved at about 315 hours.
Figure 38:
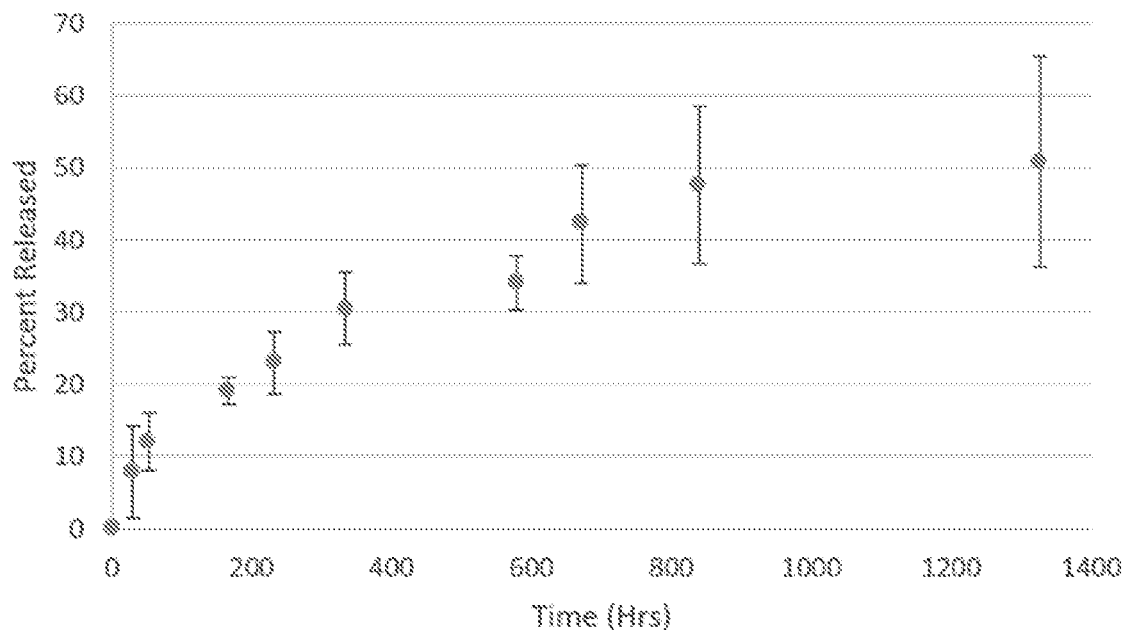
FIG. 38 shows a representative drug release profile for a representative disclosed drug delivery composition comprising 0.15 wt % metformin over a period of about 1330 hours. The data show an extended release of drug over the time period examined, with a cumulative release of about 50% of the initial drug load achieved at about 1330 hours.
Figure 39:
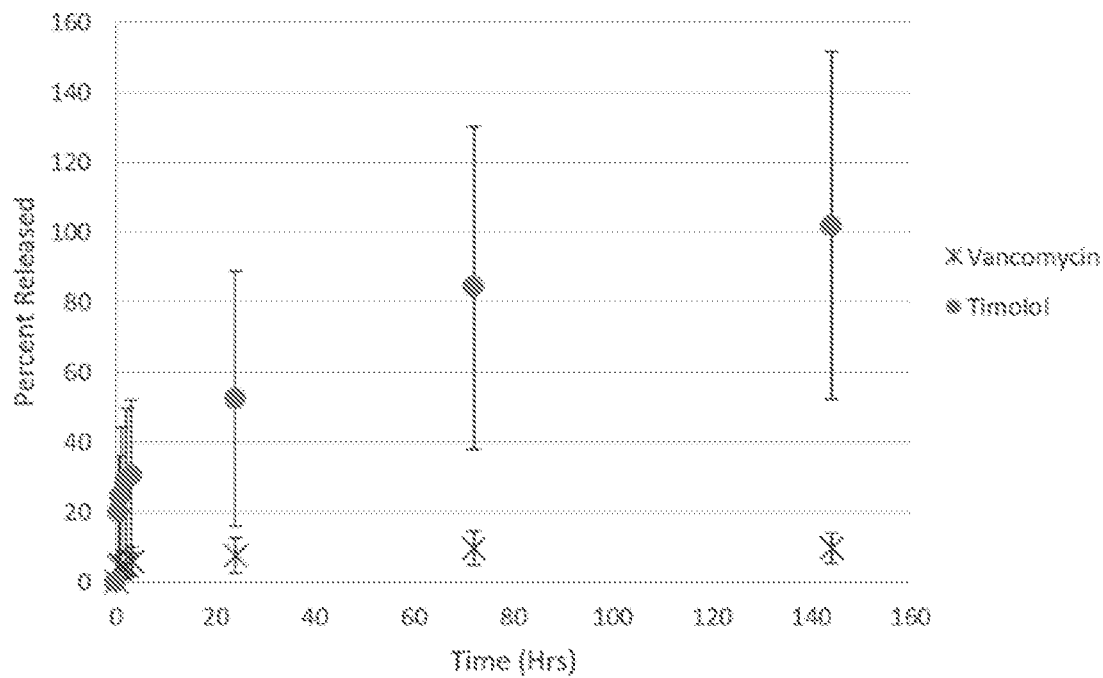
FIG. 39 shows a representative drug release profile for a representative disclosed dual drug delivery composition comprising 10 wt % vancomycin as well as 10% timolol maleate over a period of about 144 hours. The data show an extended release of drug over the time period examined, with a cumulative release of about 10% of the initial drug load of vancomycin and about 100% of the initial drug load of timolol maleate achieved at about 144 hours.
Figure 40:
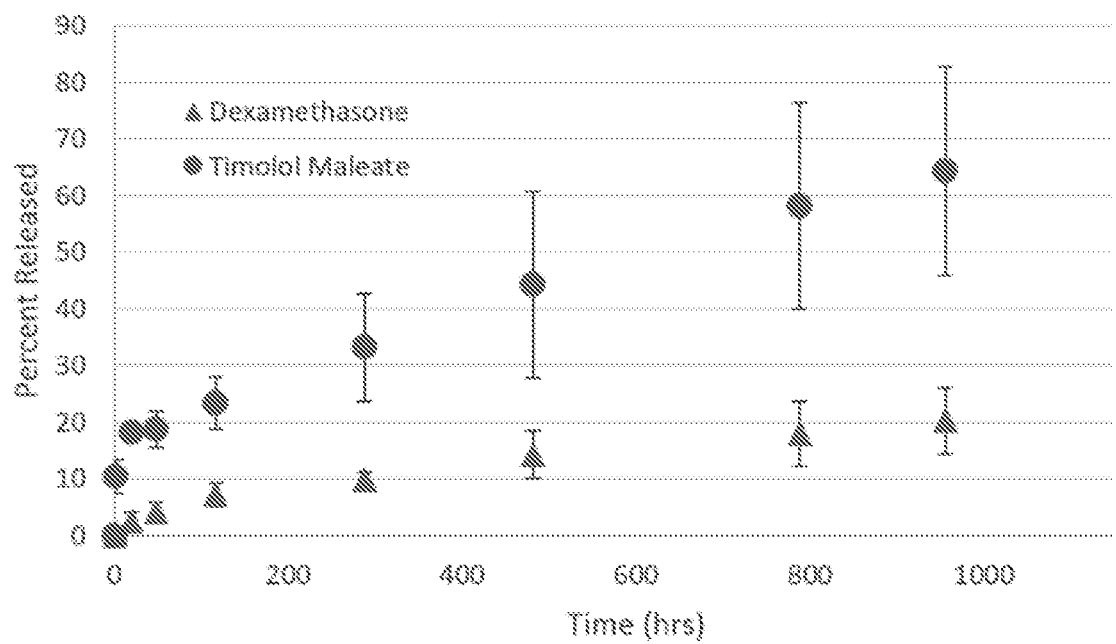
FIG. 40 shows a representative drug release profile for a representative disclosed dual drug delivery composition comprising 28 wt % dexamethasone as well as 10% timolol maleate over a period of about 960 hours. The data show an extended release of drug over the time period examined, with a cumulative release of about 20% of the initial drug load of dexamethasone and about 64% of the initial drug load of timolol maleate achieved at about 960 hours.

Metformin hydrochloride was added to the water phase of a water in oil (W/O) microemulsion, and then the emulsion was gelled (Formulation L, Table 1). The timolol maleate concentration in the aqueous phase was 0.5% and the microemulsion contained 3% aqueous phase, resulting in an overall drug loading of 0.15% by mass and a total drug loading of 56 µg in the ejected drug delivery composition. FIG. 38 shows a cumulative release of about 50% of the loaded drug was after 1330 hours. Since metformin hydrochloride is hydrophilic, 100% release of the loaded drug was predicted. The extended release of the drug is likely due to the low solubility of the drug in the oil phase. Moreover, a very large fraction of the drug is ionized at the pH of the aqueous phase. The ionized drug does not partition into the oil phase and so the concentration of the drug in the oil phase that is in equilibrium with the PBS is very low. The drug containing water drops therefore act as drug depots releasing the drug slowly to the oil as the drug diffuses from the oil into the surrounding aqueous phase. The transport therefore can be described by the Higuchi model that was initially derived for transport from ointments containing drug particles (Higuchi, T. *Journal of Pharmaceutical Sciences.* (1961) 50:874-875; Xu, Xiaoming, et al. *International Journal of Pharmaceutics.* (2015) 494:31-39; Siepmann, J. and Peppas, N. *International Journal of Pharmaceutics.* (2011) 418:6-12). Similar models have been used to describe drug transport from hydrogels containing drug particles or surfactant aggregates that have a high affinity for the drug (Gupta, C. and Chauhan, A. *Journal of Colloid and Interface Science.* (2010) 347:31-42).

m. Release of Vancomycin Hydrochloride from an Oleogel Drug Delivery Composition Comprising Solid Drug Particles Devices were prepared by adding vancomycin hydrochloride powder to the oil phase (corresponding to Formulation M, Table 1). FIG. 36 shows release data for a study in which vancomycin hydrochloride was added directly to oil as it was cooling in order to prepare an oleogel drug delivery composition comprising 25 wt % vancomycin hydrochloride. The volume of the ejected oleogel drug delivery composition comprising timolol was 0.0030 mL, and this volume was ejected into release medium with a volume of 10 mL. The data show an extended release of drug over the time period examined, with a cumulative release of about 91% of the initial drug load achieved at about 630 hours.

n. Release of Metformin Hydrochloride from an Oleogel Drug Delivery Composition Comprising Solid Drug Particles Incorporation of metformin hydrochloride in the aqueous phase of the microemulsions resulted in the long release duration but the overall drug loading in the device was only 0.15%. By contrast, the drug loading that can be achieved by direct addition of the drug into the oil phase could be as high as 20-30%. So, devices were prepared by adding timolol maleate powder to the oil phase (corresponding to Formulation N, Table 1). FIG. 37 shows release data for a study in which metformin hydrochloride was added directly to oil as it was cooling in order to prepare an oleogel drug delivery composition comprising 5 wt % metformin hydrochloride. The volume of the ejected oleogel drug delivery composition comprising metformin was 0.0040 mL, and this volume was ejected into release medium with a volume of 10 mL. The data show an extended release of drug over the time period examined, with a cumulative release of about 81% of the initial drug load achieved at about 315 hours. The drug release was slower compared to dexamethasone phosphate but much faster compared to the metformin hydrochloride release when it was loaded into the microemulsion. The slower release compared to dexamethasone phosphate is likely due to a lower solubility of metformin hydrochloride in the oil, as evident from the presence of particles in the gel. The much faster release compared to the microemulsions suggests that the solubility limit of metformin hydrochloride in the oil is much higher than the concentration of the non-ionized drug in the oil phase when the drug was dissolved in the aqueous phase of the microemulsions. The transport therefore can be described by the Higuchi model initially derived for transport from ointments containing drug particles (Higuchi, T. Journal of Pharmaceutical Sciences. (1961) 50:874-875; Xu, Xiaoming, et al. International Journal of Pharmaceutics. (2015) 494:31-39; Siepmann, J. and Peppas, N. International Journal of Pharmaceutics. (2011) 418:6-12).

o. Release of Vancomycin Hydrochloride and Timolol Maleate from an Oleogel Drug Delivery Composition Comprising Solid Particles from Both Drugs In some instances, there may be a need to administer oleogels in which multiple drugs have been loaded into one mixture. An oleogel comprised of both vancomycin hydrochloride and timolol maleate was prepared by first melting a soybean oil and ethyl cellulose oleogel, then adding drug particles of vancomycin hydrochloride and timolol maleate to the mixture to achieve a composition of 10 wt % vancomycin hydrochloride and 10 wt % timolol maleate in the final formulation (this formulation corresponds to Formulation O, Table 1). The majority of the drugs remained undissolved resulting in oleogel drug delivery composition that comprised of dispersed particles from each drug. The volume of the ejected oleogel drug delivery composition comprising of vancomycin hydrochloride and timolol maleate was 0.0030 mL, and this volume was ejected into release medium with a volume of 10 mL. FIG. 39 shows a representative drug release profile for a representative disclosed dual drug delivery composition comprising 10 wt % vancomycin as well as 10% timolol maleate over a period of about 144 hours. The data show an extended release of drug over the time period examined, with a cumulative release of about 10% of the initial drug load of vancomycin and about 100% of the initial drug load of timolol maleate achieved at about 144 hours.

p. Release of Dexamethasone and Timolol Maleate from an Oleogel Drug Delivery Composition Comprising Solid Particles from Both Drugs The formulation used in this study corresponds to formulation P (Table 1) with dexamethasone and timolol maleate, and it was prepared in a similar manner to that described for the preparation of formulation O (Table 1). Dexamethasone and timolol maleate in powder form was added to a soybean oil and ethyl cellulose mixture to achieve a final composition of 28 wt % dexamethasone and 10 wt % timolol maleate. The volume of the ejected oleogel drug delivery composition comprising of dexamethasone and timolol maleate was 0.0030 mL, and this volume was ejected into release medium with a volume of 10 mL. FIG. 40 shows a representative drug release profile for the dual drug delivery composition comprising 28 wt % dexamethasone as well as 10 wt % timolol maleate over a period of about 960 hours. The data show an extended release of drug over the time period examined, with a cumulative release of about 20% of the initial drug load of dexamethasone and about 64% of the initial drug load of timolol maleate achieved at about 960 hours.

9. Comparison of Dexamethasone Release from Different Drug Delivery Compositions.

Figure 27:
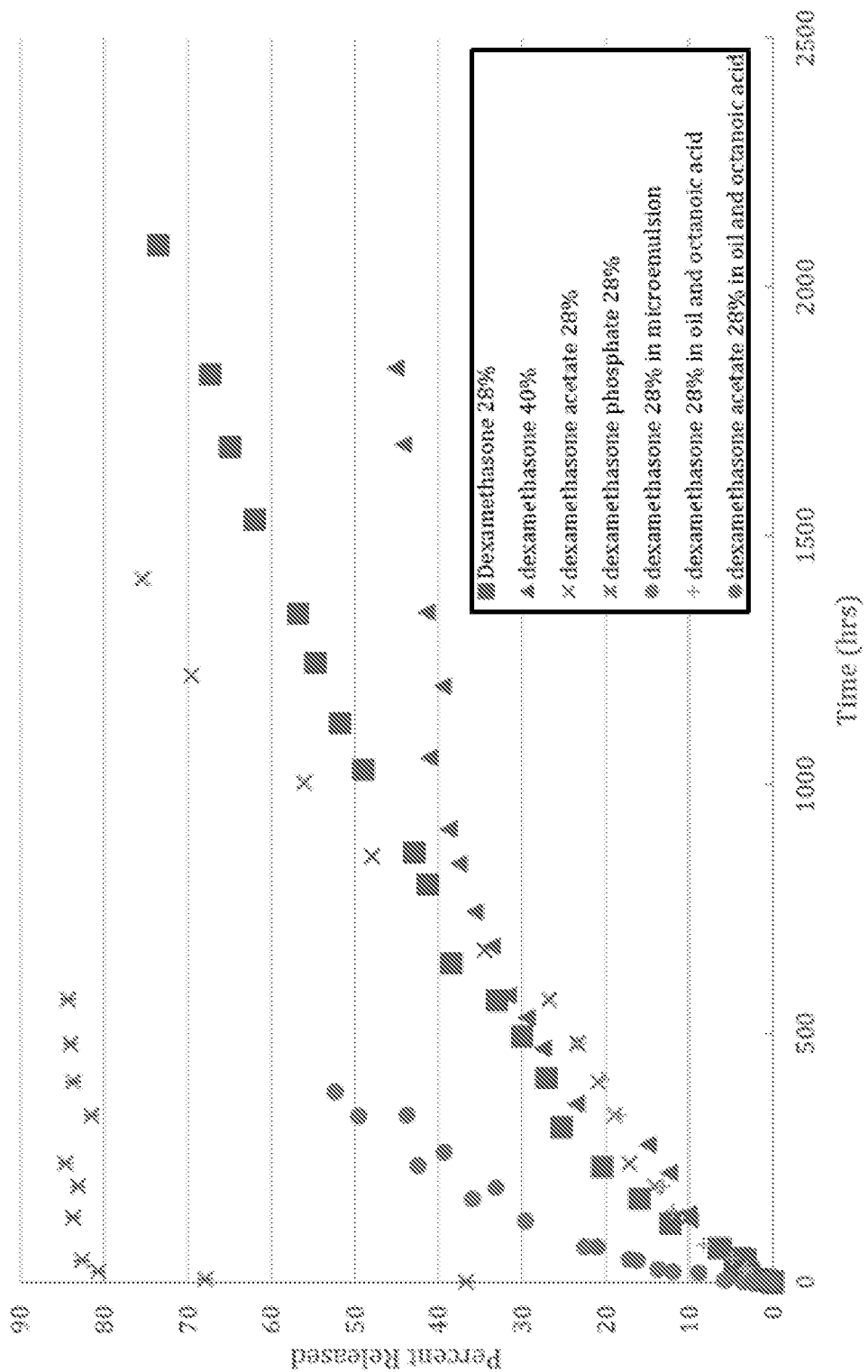
FIG. 27 shows representative drug release profiles for representative drug delivery compositions comprising 28 wt % dexamethasone, or analogues thereof. A key describing the different formulations and form of dexamethasone is shown in the inset of the figure. The data show that the release characteristics can be specifically modulated by the composition and form of the disclosed drug delivery composition.

In the foregoing examples, several drug delivery compositions were assessed comprising as a drug, dexamethasone. In order to easily compare the results, the release data from various studies are shown in FIG. 27 for all formulations that contain dexamethasone or a derivative thereof. The data show that the longest release duration was obtained for a drug delivery composition wherein dexamethasone was added to the oil without the micro emulsion phase. These examples show that disclosed drug delivery compositions are able to provide release durations over several months for compositions comprising either timolol or dexamethasone.

10. Testing of a Drug Delivery Composition in an Ex Vivo Model of the Human Eye.

A representative disclosed drug delivery composition was assessed in an ex vivo model of the human in order to characterize potential behavior of the composition following administration to a patient. Briefly, a drug delivery composition comprising dexamethasone was injected into a rabbit eye (Pel-Freez Biologicals, Rogers, Ark.) using a syringe and needle. FIGS. 28A-28C show representative images for three stages of a disclosed injection technique. The images show that the drug delivery composition remained in the vitreous after the needle was removed, sinking towards the bottom of the eye due to its density. Due to the hole created by the large sized needle, a few drops of vitreous fluid was observed to be lost via drainage. The injection site hole was sealed using cyanoacrylate glue gel. The results of this preliminary injection procedure suggest that the disclosed drug delivery composition can be a viable method for intravitreal injection

11. Prototype Drug Delivery Device Comprising a Plurality of Exit Openings.

Figure 30A:
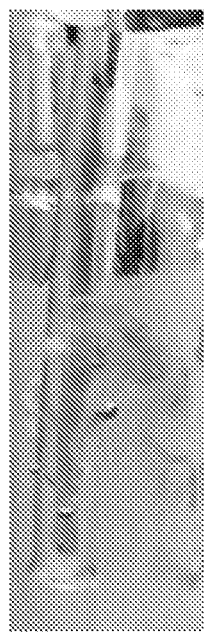
FIGS. 30A-30B show representative images of a drug delivery composition that was ejected into phosphate-buffered saline using a model of the needle shown in FIG. 29. Briefly, a plastic tube was fabricated with a plurality of exit openings arranged with a diagonal cross-sectional aspect.
Figure 30B:
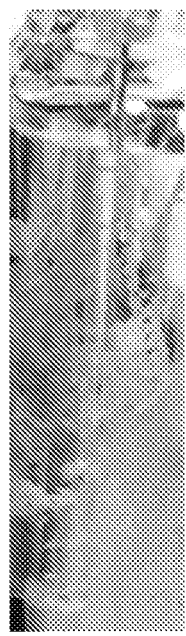

As described herein above, an injection device is disclosed that would allow injection of a disclosed drug delivery composition with minimal motion in the vitreous after injection. Briefly, an injection needle comprising a plurality of exit openings can provide an injected drug delivery composition comprising a network of gelled drug delivery composition instead of a single injection mass with a cylindrical geometry. A smaller radius and a long length will significantly reduce the potential for motion after injection into the vitreous. A prototype of the device shown in FIGS. 29A-29C was created using plastic polymer tubing. Holes were drilled into tubing, which was attached to a needle tip. The gel was pushed through the needle tip into the tubing, where it escaped into the surrounding aqueous medium (phosphate-buffered saline) via the plurality of holes in the polymer tubing. The results are shown in FIGS. 30A and 30B. In this example, the oleogel drug delivery composition was prepared for the purposes of demonstrating the function of the prototype device, and thus, the oleogel drug delivery composition was not loaded with drug.

12. Stability of an Oleogel Drug Delivery Composition in an Ex Vivo Model of Human Eye.

Briefly, frozen rabbit eyes (Pel-Freez Biologicals) were removed from a freezer and allowed to thaw at room temperature for 1 hour. A 19 gauge needle was bored through the side of the rabbit eye, such that the tip was centralized in the vitreous. The oleogel drug delivery composition was injected through the needle tip into the vitreous. When the injection was complete, the needle was removed from the eye, and the device dislodged from the needle aperture due to friction forces from within the eye. To prevent leakage, the hole created by the needle was sealed using a cyanoacrylate glue. The oleogel drug delivery composition was prepared similarly to the 28 wt % dexamethasone formulation shown in Table 1, except the drug level was at 10 wt % and further comprised Solvent Green 5 (Fastcolours, LLP, Huddersfield, United Kingdom). The Solvent Green 5 was present in amount of approximately less than or equal to about 0.05 wt % (about 500 µg Solvent Green 5 per 1 g of oleogel.

Figures 35A, 35B, 35C:
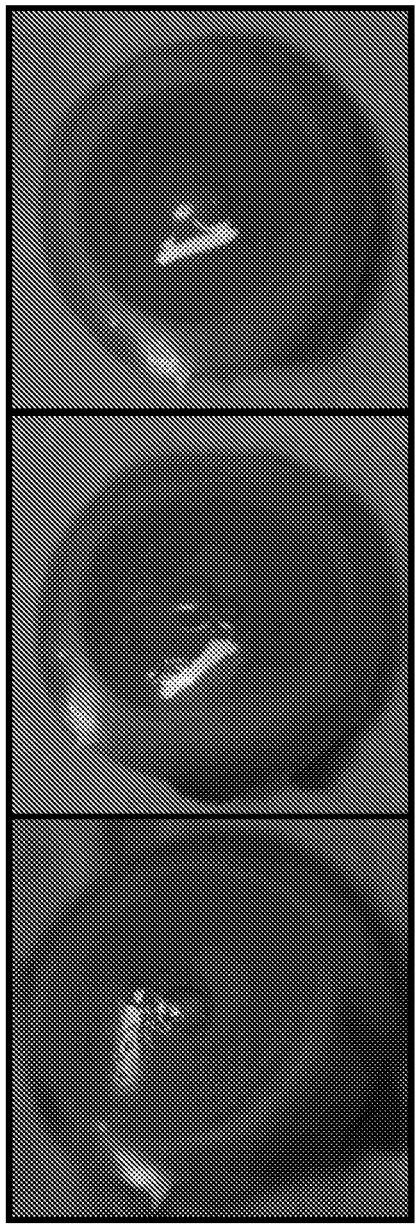
FIGS. 35A-35D show representative images for a representative drug delivery composition within an ex vivo animal model of the human eye. Briefly, a representative drug delivery composition was formulated comprising a fluorescent dye, and then injected into the model eye.
Figures 35D, 35E:
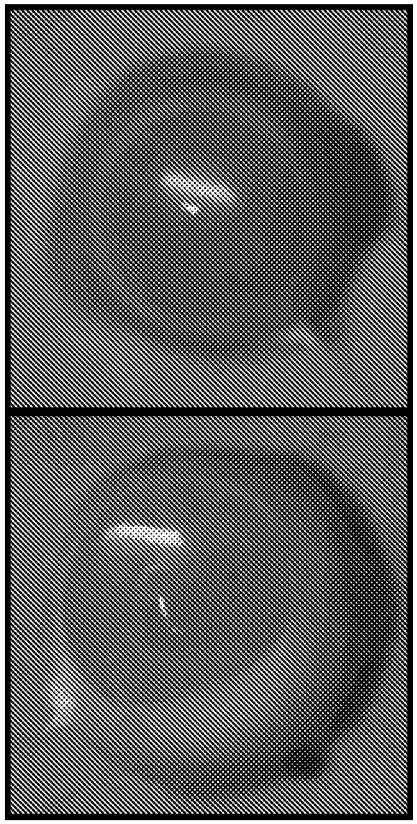
FIG. 35E shows the same drug delivery composition comprising the fluorescent dye at seven days following injection. The image shows that the drug delivery composition comprising the fluorescent dye remains clearly visible and apparently intact. The composition appears to have moved within the vitreous due to handling of the model eye during the study period.

Images at various time points following injection are shown in FIGS. 35A-35E. Pictures of fluorescent oleogel device injected into the vitreous of a rabbit eye. (A) A rod like device is injected into the eye. FIG. 35A shows the drug delivery composition comprising the fluorescent dye immediately after injection. The image shows that the drug delivery composition following injection into the vitreous has a physical structure of a rod or cylinder. The fluorescent spot near the lateral side of the model eye is the injection site showing residual amounts of the drug delivery composition comprising the fluorescent dye adhering near the injection entry site. FIG. 35B shows the same drug delivery composition comprising the fluorescent dye at two days following injection. The image shows that the drug delivery composition comprising the fluorescent dye remains clearly visible and apparently intact near the front of the eye. FIG. 35C shows the same drug delivery composition comprising the fluorescent dye at four days following injection. The image shows that the model eye tissue is beginning to degrade, thus coloring the model eye lens. However, the drug delivery composition comprising the fluorescent dye remains clearly visible and apparently intact. FIG. 35D shows the same drug delivery composition comprising the fluorescent dye at five days following injection. The image shows that the drug delivery composition comprising the fluorescent dye remains clearly visible and apparently intact near the front of the eye at five days post-injection into the vitreous. FIG. 35E shows the same drug delivery composition comprising the fluorescent dye at seven days following injection. The image shows that the drug delivery composition comprising the fluorescent dye remains clearly visible and apparently intact. The composition appears to have moved within the vitreous due to handling of the model eye during the study period.

The results of show that an exemplary disclosed drug delivery composition does not sink to the back of the eye due to the viscous nature of the vitreous. The results further show injected drug delivery composition has a geometry similar to the ejected drug delivery compositions used in the drug release experiments described above. Thus, the injection procedure into an ex vivo model of the human eye did not affect the shape of the device. Due to limitations with the shelf life of a rabbit eye after they have been thawed, cells begin to degrade and can no longer provide accurate photographs of devices after a week.

13. Kinetic Modeling of Drug Release from Exemplary Drug Delivery Compositions.

As discussed above, photomicrographs showed that in some formulations, drug particles are apparent in the oleogel drug delivery compositions. In modeling the kinetic behavior of such composition, they can be modeled as cylinders with undissolved drug particles trapped by the gel. For example, a similar geometry was observed for conjunctival inserts of cyclosporin A (Gupta, C. and Chauhan, A. *Journal of Colloid and Interface Science*. (2010) 347:31-42). The mechanism for each trial can be attributed to a combination to two mass transfer resistances, one is diffusion in the surrounding bulk fluid, and the other is diffusion within the gel. The magnitude of the resistance in each phase is related to the boundary layer thickness in that phase. In all release experiments, the first few hours are categorized by a burst in drug release. Because the boundary layer thickness in the fluid is independent of time, yet boundary layer thickness in the gel is initially zero and increases with time, we hypothesize that short-time behavior can be attributed to resistance in the fluid phase. The mechanism of release begins with drug dissolved within the oil phase. The dissolved drug diffuses into PBS to lower the concentration of drug in the gel below the solubility limit. As oil phase drug dissolves into the PBS, large drug particles suspended in the gel begin to dissolve into the oil phase of the gel. These instantaneous phenomena cause a depletion zone near the surface of the gel, which is an area within the device that contains drug at solubility limit, but no remaining particles.

Figure 34:
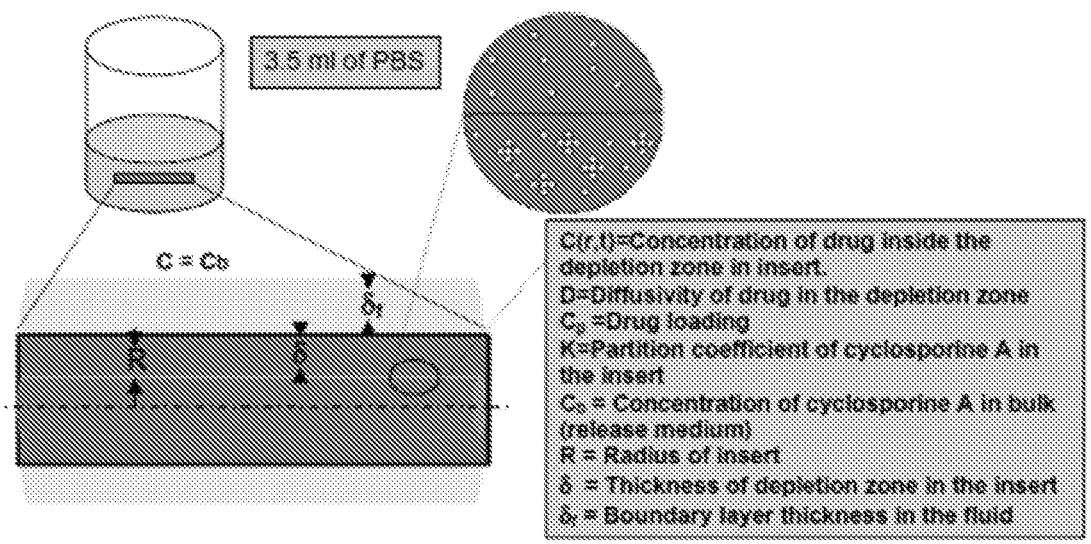
FIG. 34 shows a representative model for kinetics of delivery of a therapeutic agent from a disclosed drug delivery composition. The inset associated with figure defines the variables used in the mathematical model, which is described in greater detail herein below.

FIG. 34 shows schematically such a depletion area within a cylindrical gel device. It can be assumed that the concentration profile within the depletion zone follows the pseudo-steady state hypothesis because the total drug loading is sufficiently above the solubility limit to induce undissolved drug particles. In FIG. 34, a model disclosed oleogel drug delivery composition is loaded with drug well above the solubility limit in the oil, such that particles of undissolved drug exist within the gel. At time t=0, drug exists uniformly around the gel. When placed in PBS, dissolved drug near the surface of the device begins to diffuse into surrounding PBS, which causes a chain reaction of particles at the surface to dissolve into the oil phase, creating a depletion zone, 5 (Gupta, C. and Chauhan, A. *Journal of Colloid and Interface Science*. (2010) 347:31-42).

The depletion zone, of thickness $\delta$, is located at a distance $(R-\delta)$ from $r=0$, where R is the total radius of the oleogel device. For the present kinetic model, it is hypothesized that the radial diffusive flux of dissolved drug particles causes the depletion zone thickness to increase by $\Delta\delta$, which can be modeled as:

$$-D\frac{\partial C}{\partial r}2\pi rL = C_p 2\pi(R-\delta)L\frac{\Delta\delta}{\Delta t} \quad \delta < r < R \quad (1)$$

where $C=C(r,t)$ is the concentration at time t and distance r inside the depletion layer $\delta<r<R$, D is the effective diffusivity of drug within the gel, and $C_p$ is the initial concentration of drug in the gel. Equation (1) can be simplified to:

$$r\frac{\partial C}{\partial r} = -\frac{(R-\delta)}{D}\frac{d\delta}{dt}C_p \quad \delta < r < R \quad (2)$$

which has the following boundary conditions:

$$\text{at } r = (R-\delta), C = KC^* \text{ at} \quad (3)$$

$$r = R, C = KC_f \text{ at} \quad (4)$$

$$r = R, -D\frac{\partial C}{\partial r} = \frac{D_{fluid}(C_f - C_b)}{\delta_f} \quad (5)$$

where K is the partition coefficient of the gel, the ratio between equilibrium concentration of drug in gel and drug in the PBS. C* is the solubility limit of drug in PBS, D and $D_{fluid}$ are effective diffusivity of drug in the oleogel and in PBS, respectively. $C_f$ is the drug concentration at any time t in the fluid at the interface between gel and PBS, (r=R), and $\delta_f$ is the boundary layer thickness of the mass-transfer boundary layer in PBS. $C_b$ is the concentration of drug in the bulk phase, which is zero in our experiments due to assumed sink conditions. Equilibrium conditions (3) exist between the concentration in the dissolved oil phase of the gel at solubility limit C* and the total drug concentration in the gel, KC*. At the interface the device and the PBS (r=R), drug concentration in the gel C is in equilibrium with the fluid concentration, $C_f$. Fluid concentration $C_f$ at (r=R) decreases to the bulk concentration $C_b$ at r=R+$\delta_f$, where $\delta_f$ is the mass-transfer boundary layer thickness in PBS. The diffusive flux in the mass-transfer boundary layer in fluid is $$\frac{D_{fluid}(C_f - C_b)}{\delta_f}.$$

This expression assumes $\delta_f$ is much smaller the radius of the device and doesn't account for curvature of the gel. Diffusive fluxes inside the gel and outside the gel at (r=R) must be equal, which gives the boundary condition (5). Using these equations, concentration of drug in the bulk PBS can be found as a function of time; that is:

$$V_b \frac{dC_b}{dt} = 2\pi(R-\delta)LC_p\frac{d\delta}{dt} \quad (6)$$

where $V_b$ is the volume of PBS used in the experiment. The concentration $C_b$ increases with time.

In other disclosed oleogel drug delivery compositions, a drug can completely dissolve into the oil phase of the composition, and therefore no particles are not present. For these compositions, drug release follows a simple cylindrical diffusion model. It can be assumed that the diffusion is unidirectional because the length of the device is much longer than the radius. This gives a diffusion equation of:

$$D\frac{\partial^2 C}{\partial r^2} + \frac{D}{r}\frac{\partial C}{\partial r} = \frac{\partial C}{\partial t} \quad (7)$$

where C(r, t) is the total drug concentration in the oleogel at position r and time t. Concentration profiles can be found by using the boundary conditions often given by uptake experiments:

$$C = KC_0^* \text{ at } r = R \quad (8)$$

$$D\frac{\partial C}{\partial r} = 0 \text{ at } r = 0 \quad (9)$$

$$C = 0 \text{ at } t = 0 \quad (10)$$

where K is the partition coefficient of the dissolved drug in the gel, $C_0^*$ is concentration of drug added to gel, and R is the radius of the device. Equation (7) can be solved analytically to give:

$$C(r,t) = KC_0^* - \sum_{n=1}^{\infty} \frac{2KC_0^*}{\lambda_n J_1(\lambda_n)} J_0\left(\frac{\lambda_n r}{R}\right) e^{-\frac{\lambda_n^2 D}{R^2}t} \quad (11)$$

where $J_0$ and $J_1$ are Bessel functions of zero and first order respectively, and $\lambda_n$ are the zeros of $J_0$. Using the boundary conditions and initial conditions for drug release:

$$C = 0 \text{ at } r = R \quad (12)$$

$$D\frac{\partial C}{\partial r} = 0 \text{ at } r = 0 \quad (13)$$

$$C = C_1(r) \text{ at } t = 0 \quad (14)$$

which are based on the cylindrical symmetry of the device and assumed perfect sink conditions, equations (7) and (13) can be solved analytically to solve for the concentration profile:

$$C = \sum_{n=1}^{\infty} \frac{2KC_0^*}{\lambda_n J_1(\lambda_n)} \left(1 - e^{-\frac{\lambda_n^2 D}{R^2}t}\right) J_0\left(\frac{\lambda_n r}{R}\right) e^{-\frac{\lambda_n^2 D}{R^2}t} \quad (15)$$

of the device during release experiments. The total drug released into the medium M(t) can be related to the flux at the interface between gel and medium using:

$$\frac{dM}{dt} = -D\left(\frac{\partial C}{\partial r}\right)_{r=R} 2\pi RL \quad (16)$$

Combining equations (15) and (16) leads to and integrating with respect to t yields M(t):

$$M = 4KC_0^* V_{device} \sum_{n=1}^{\infty} \frac{\left(1 - e^{-\frac{\lambda_n^2 D}{R^2}t}\right)\left(1 - e^{-\frac{\lambda_n^2 D}{R^2}t}\right)}{\lambda_n^2} \quad (17)$$

where $V_{device}$ is the volume of the oleogel and D is the diffusivity. K and D are unknown and so therefore are used as a fitting parameter to fit experimental data of release.

The foregoing models can be used during optimization and design of specific disclosed oleogel drug delivery compositions.

It will be apparent to those skilled in the art that various modifications and variations can be made in the present disclosure without departing from the scope or spirit of the disclosure. Other embodiments of the disclosure will be apparent to those skilled in the art from consideration of the specification and practice of the disclosure disclosed herein. It is intended that the specification and examples be considered as exemplary only, with a true scope and spirit of the disclosure being indicated by the following claims.

What is claimed is:

1. A composition consisting of an oleogel and a therapeutic agent, wherein the oleogel consists of one or more oils, and a gelator, and optionally includes octanoic acid, and wherein the therapeutic agent is selected from one or more of cyclosporine A, dexamethasone, metformin, timolol, triamcinolone, vancomycin, and pharmaceutically acceptable salts thereof.

2. The composition according to claim 1, wherein the therapeutic agent is timolol, or a pharmaceutically acceptable salt thereof; and wherein the therapeutic agent is present in an amount from about 5 wt % to about 50 wt % based on the weight of the one or more oils, the gelator, and the therapeutic agent.

3. The composition according to claim 1, wherein the oil phase comprises a soybean oil.

4. The composition according to claim 1, wherein the gelator comprises an ethyl cellulose.

5. The composition according to claim 4, wherein the ethyl cellulose is present in an amount from about 5 wt % to about 20 wt % based on the weight of the one or more oils and of the gelator.

6. The composition according to claim 1, wherein the octanoic acid is present in an amount from about 10 wt % to about 30 wt % based on the weight of the one or more oils, the gelator, and the octanoic acid.

* * * * *